(12) United States Patent
Novak et al.

(10) Patent No.: US 12,036,238 B2
(45) Date of Patent: Jul. 16, 2024

(54) METHOD OF TREATING PARKINSON'S AND OTHER NEURODEGENERATIVE DISEASES

(71) Applicant: Vector Vitale IP LLC, North Miami Beach, FL (US)

(72) Inventors: Peter Novak, Sunny Isles Beach, FL (US); Max Temnik, Miami, FL (US); Oleksandr Balakin, Dnepropetrovsk (UA)

(73) Assignee: Vector Vitale IP LLC, North Miami Beach, FL (US)

( * ) Notice: Subject to any disclaimer, the term of this patent is extended or adjusted under 35 U.S.C. 154(b) by 0 days.

(21) Appl. No.: 18/238,817

(22) Filed: Aug. 28, 2023

(65) Prior Publication Data

US 2024/0173350 A1 May 30, 2024

Related U.S. Application Data

(63) Continuation of application No. 17/768,190, filed as application No. PCT/US2019/055770 on Oct. 11, 2019, now Pat. No. 11,779,597.

(51) Int. Cl.
*A61K 33/30* (2006.01)
*A61K 33/00* (2006.01)
*A61K 47/54* (2017.01)
*A61P 25/16* (2006.01)

(52) U.S. Cl.
CPC ............. *A61K 33/30* (2013.01); *A61K 33/00* (2013.01); *A61K 47/541* (2017.08); *A61P 25/16* (2018.01)

(58) Field of Classification Search
CPC ...... A61K 33/30; A61K 33/00; A61K 47/541; A61P 25/16
See application file for complete search history.

(56) References Cited

U.S. PATENT DOCUMENTS

| | | |
|---|---|---|
| 9,861,659 B2 | 1/2018 | Novak et al. |
| 10,183,041 B2 | 1/2019 | Novak et al. |
| 10,226,484 B2 | 3/2019 | Novak et al. |
| 10,799,530 B1 | 10/2020 | Novak et al. |
| 10,933,091 B1 | 3/2021 | Novak et al. |

FOREIGN PATENT DOCUMENTS

| | | |
|---|---|---|
| EP | 0472053 A2 | 2/1992 |
| JP | 5039256 B2 | 10/2012 |
| WO | 2015185602 A1 | 12/2015 |

OTHER PUBLICATIONS

International Application No. PCT/US2019/055770, International Search Report and Written Opinion mailed Jul. 10, 2020, 13 pages.
Adlard et al., "Metals and Alzheimer's Disease: How Far Have We Come in the Clinic?", Journal of Alzhemer's Disease, vol. 62, No. 3, Mar. 13, 2018, pp. 1369-1379.
Roberts et al., "Rubidium and Potassium Levels are Altered in Alzheimer's Disease Brain and Blood but not in Cerebrospinal Fluid," ACTA Neurologica Communications, vol. 4, No. 1, Nov. 14, 2016, pp. 1-8.
Casacchia et al., "Cloruro di Rubidio di Parkinson—[Rubidium Chloride in Parkinson's Disease: Preliminary Results]" ACTA Neurologica, Chirurgia,, Naples, IT, vol. 30, No. 6, Jan. 1975, pp. 615-618.
Japanese Application No. 2022-522035, Office Action mailed Jul. 5, 2023, 3 pages.

*Primary Examiner* — Ali Soroush
(74) *Attorney, Agent, or Firm* — Liang & Hennessey LLP; Stanley D. Liang

(57) ABSTRACT

Compositions that comprise salts, compounds and complexes of $^{64}$Zn-enriched zinc, such as $^{64}$Zn-enriched zinc aspartate, and further optionally include $^{85}$Rb-enriched rubidium salt compounds of general formula 1, below, wherein each of $R_1$ through $R_{14}$ is independently selected from H, OH, F, Cl, Br, I, $C_1$-$C_6$ alkyl, $C_1$-$C_6$ alkoxy, and $NO_2$, such as the compound of Formula 1 in which $R_3$ is $CH_3$ and all other R groups are H for use to treat a neurodegenerative disease (NDD), such as Parkinson's disease (PD). Methods that entail administering such compositions to treat an NDD, such as PD, optionally in combination with any other treatment for an NDD such as for PD.

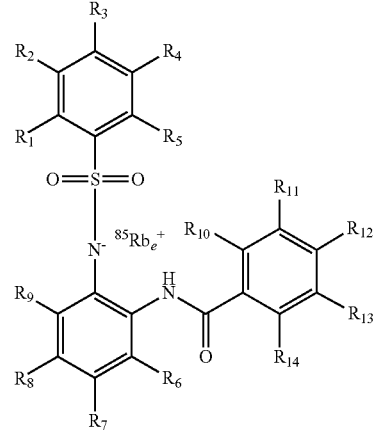

Formula 1

18 Claims, 57 Drawing Sheets

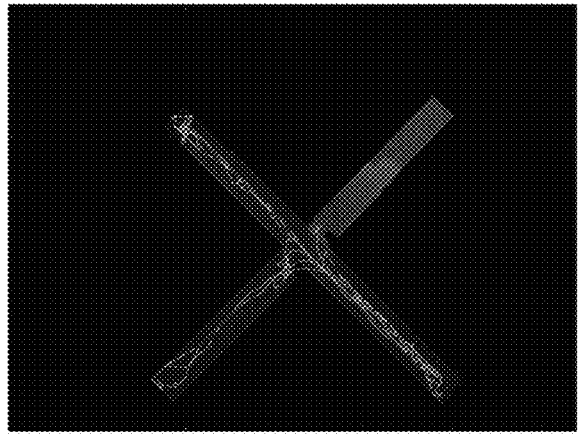
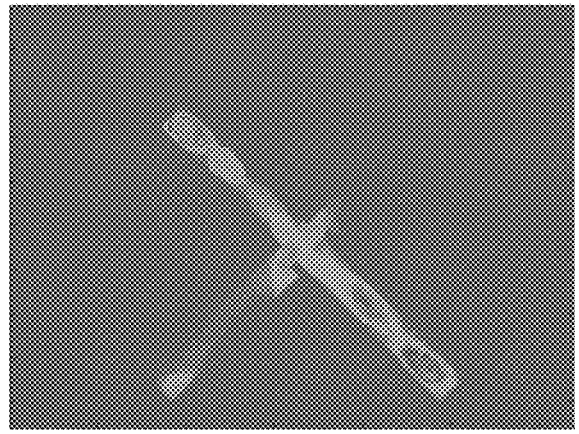
FIG. 51A  FIG. 51B
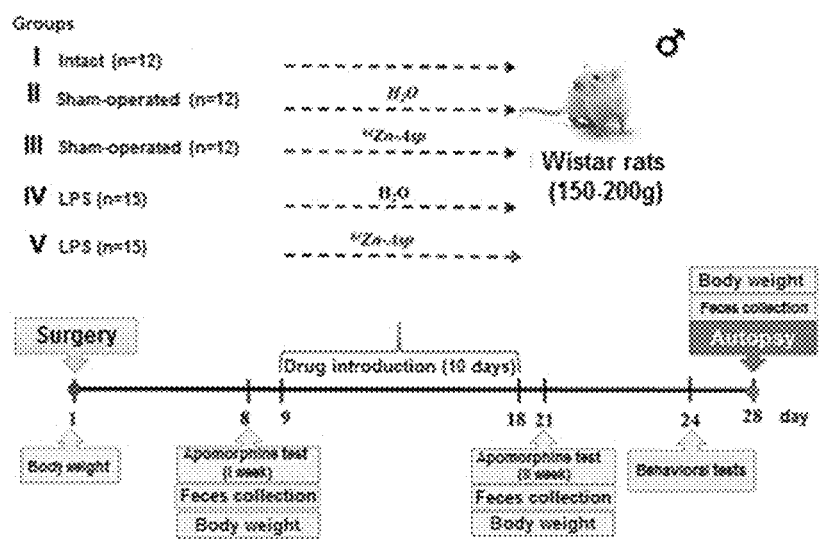
FIG. 52

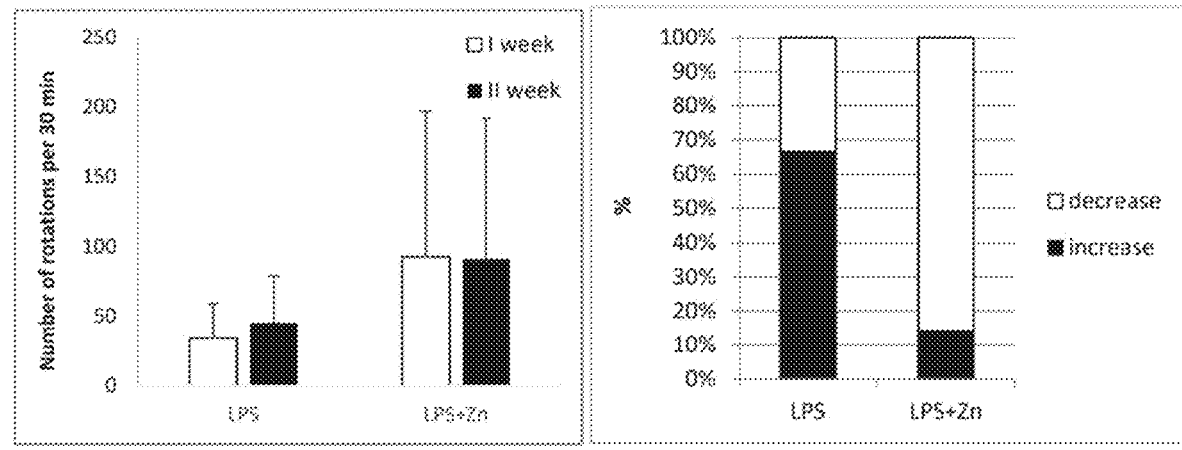
FIG. 53A          FIG. 53B
Group I – intact rats (n=3)
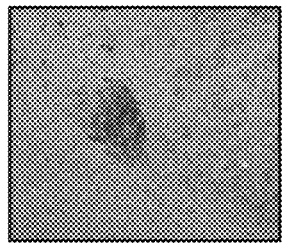 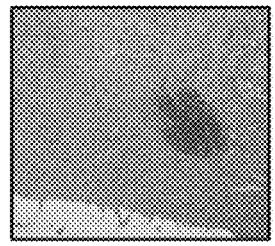 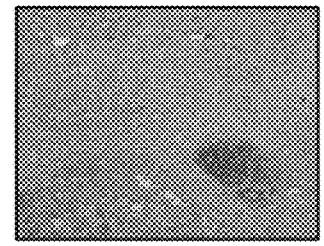
Animal 1         Animal 2         Animal 3
FIG. 54A         FIG. 54B         FIG. 54C
Group II – sham-operated rats +H$_2$O (n=3)
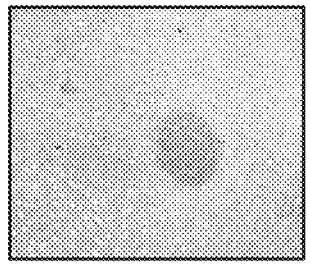 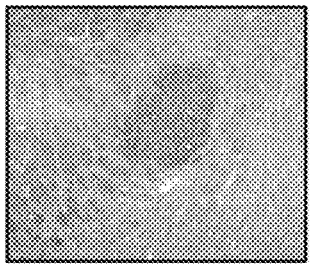 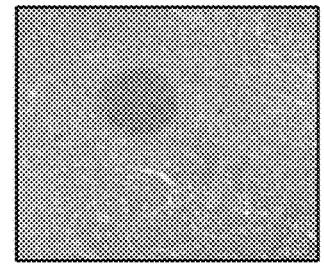
animal 1         animal 2         animal 3
FIG. 54D         FIG. 54E         FIG. 54F Group III – sham-operated rats + $^{64}$Zn-asp (n=3)
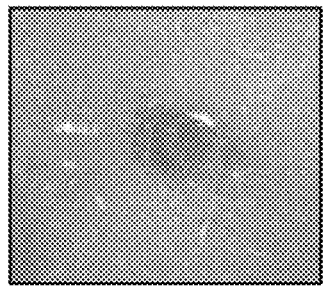 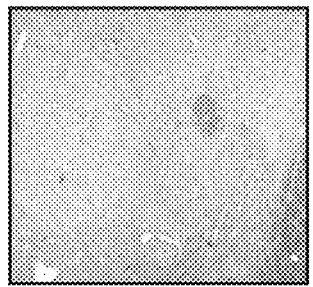 
animal 1  
FIG. 54G
animal 2  
FIG. 54H
animal 3  
FIG. 54I
Group V - LPS + $H_2O$ (n=3)
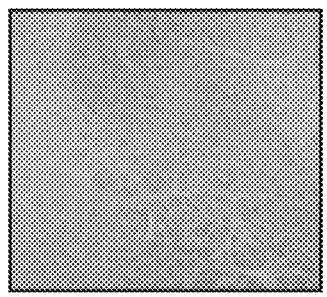 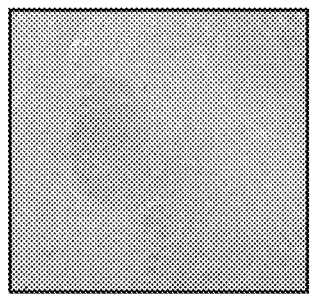 
animal 1  
FIG. 54J
animal 2  
FIG. 54K
animal 3  
FIG. 54L
Group VI - LPS + $^{64}$Zn-asp (n=3)
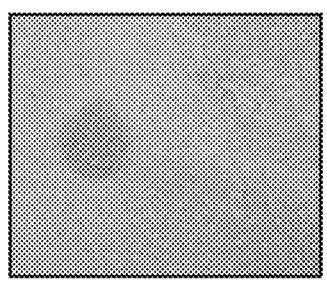 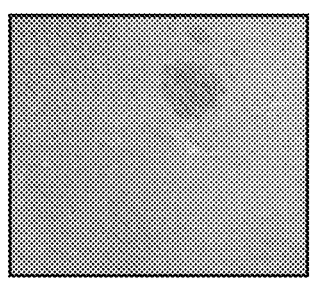 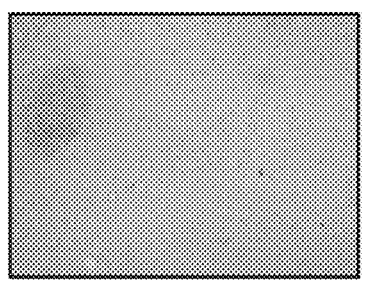
animal 1  
FIG. 54M
animal 2  
FIG. 54N
animal 3  
FIG. 54O

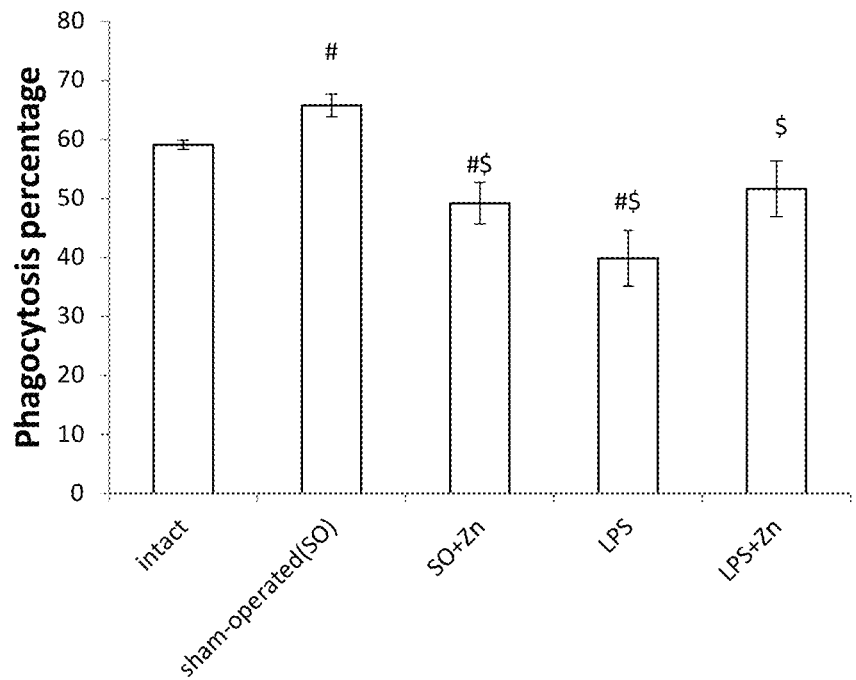
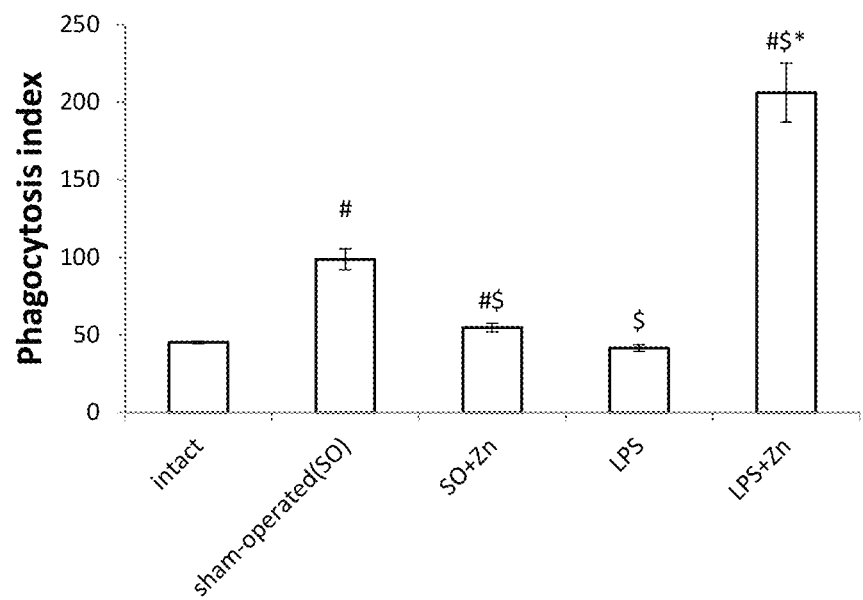

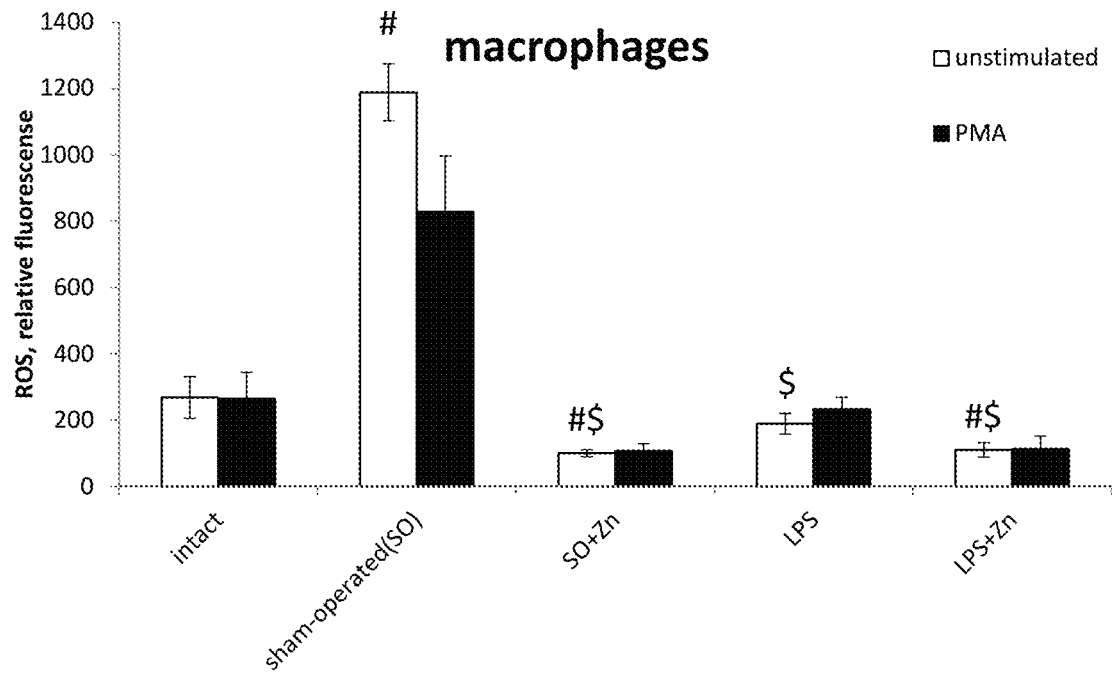
FIG. 72
FIG. 73A
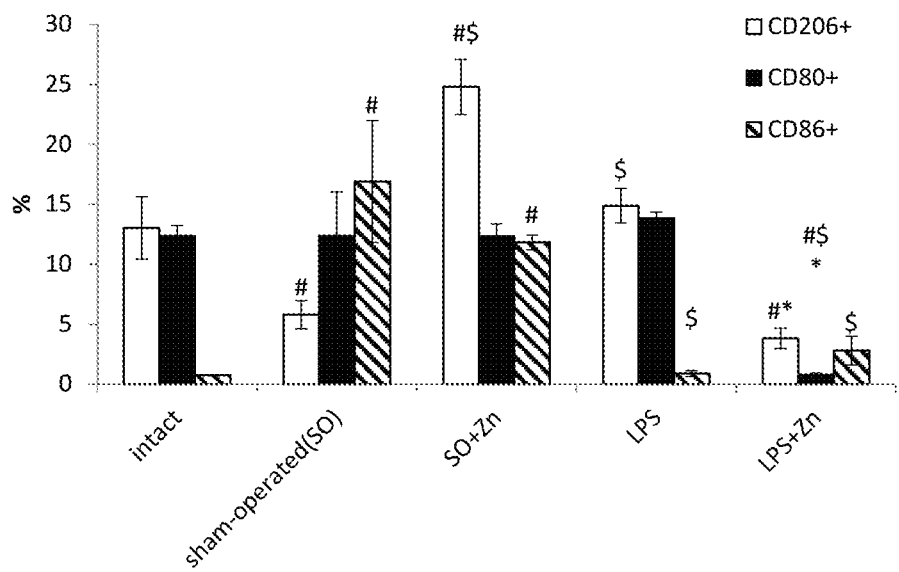

METHOD OF TREATING PARKINSON'S AND OTHER NEURODEGENERATIVE DISEASES

TECHNICAL FIELD

This disclosure relates to the field of medicine and pharmacology, and more specifically, to methods, compounds and compositions to treat neurodegenerative disorders (NDD), and in particular, Parkinson's disease (PD).

BACKGROUND

Neurodegenerative disorders (NDD), including Parkinson's disease (PD), are pathological conditions induced by an inflammatory process. A cure has not been found and effective medicines are needed.

SUMMARY

In one aspect, this disclosure provides compositions that comprise $^{64}$Zn-enriched zinc complexes, salts and compounds and/or certain $^{85}$Rb-enriched rubidium compounds to treat neurodegenerative disorders (NDD), in particular, Parkinson's disease (PD). This disclosure provides compounds, separately or in combination with each other, salts and complexes that comprise $^{64}$Zn-enriched zinc, such as $^{64}$Zn-enriched zinc aspartate, and an $^{85}$Rb-enriched rubidium organic salt (structure shown below). The disclosed composition comprises one or more of the isotope-enriched compounds, optionally in combination with other active ingredients useful to treat NDD. The disclosed composition can be used individually and in combination with other anti-NDD therapies. The disclosed compounds have low toxicity to a patient.

In certain embodiments, this disclosure provides a composition that comprises a compound of Formula 1 to treat neurodegenerative disorders (NDD), in particular, Parkinson's disease (PD).

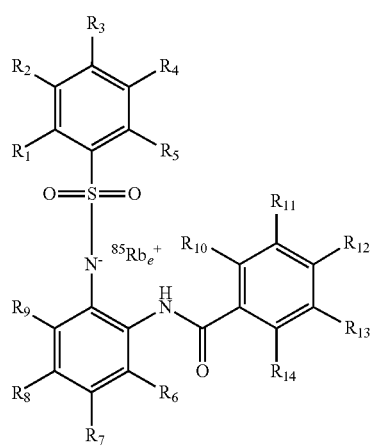

Formula 1

A compound of Formula 1 is a rubidium salt, wherein the rubidium is enriched for $^{85}$Rb and wherein each of $R_1$ through $R_{14}$ is independently selected from H, OH, F, Cl, Br, I, $C_1$-$C_6$ alkyl, $C_1$-$C_6$ alkoxy, and $NO_2$.

In certain embodiments, $R_1$, $R_2$, $R_4$, $R_5$, $R_6$, $R_8$, $R_{10}$, $R_{11}$, and $R_{13}$ of Formula 1 are all H, and
a) $R_3$ is $CH_3$ and $R_7$, $R_9$, $R_{12}$, and $R_{14}$ are all H (Compound 1),
b) $R_3$, $R_7$, $R_9$, $R_{12}$, and $R_{14}$ are all H (Compound 2),
c) $R_3$ is $CH_3$, $R_{14}$ is Cl, and $R_7$, $R_9$, and $R_{12}$ are all H (Compound 3),
d) $R_3$ is $CH_3$, $R_{14}$ is OH and $R_7$, $R_9$, and $R_{12}$ are all H (Compound 4),
e) $R_{14}$ is OH and $R_3$, $R_7$, $R_9$, and $R_{12}$ are all H (Compound 5),
f) $R_3$ is OH and $R_7$, $R_9$, $R_{12}$, and $R_{14}$ are all H (Compound 6),
g) $R_{14}$ is $NO_2$ and $R_3$, $R_7$, $R_9$, and $R_{12}$ are all H (Compound 7),
h) $R_{12}$ is Br, $R_{14}$ is $NO_2$ and $R_3$, $R_7$, and $R_9$ are all H (Compound 8),
i) $R_3$ and $R_9$ are both $OCH_3$, $R_{12}$ is Br, $R_{14}$ is $NO_2$ and $R_7$ is H (Compound 9), or
j) $R_3$ and $R_9$ are both $OCH_3$, $R_{14}$ is $NO_2$ and $R_7$ and $R_{12}$ are both H (Compound 10).

In any of the above compounds of Formula 1, in some embodiments, the rubidium is at least 75% $^{85}$Rb, at least 85% $^{85}$Rb, or at least 95% $^{85}$Rb, and in some embodiments is at least 99% $^{85}$Rb, such as 99.8% $^{85}$Rb. "Rb that is N % $^{85}$Rb" refers to Rb of which N % of the Rb atoms are the isotope $^{85}$Rb.

In certain embodiments, $R_1$, $R_2$, $R_4$, $R_5$, $R_6$, $R_8$, $R_{10}$, $R_{11}$, and $R_{13}$ of Formula 1 are all H and the remaining R groups are as defined above. In other embodiments, $R_1$, $R_2$, $R_4$, $R_5$, $R_6$, $R_8$, $R_{10}$, $R_{11}$, and $R_{13}$ of Formula 1 are all H, $R_3$ is selected from H, $CH_3$, $OCH_3$, and $NO_2$, $R_7$ and $R_9$ are each independently selected from H and $OCH_3$, and $R_{12}$ and $R_{14}$ are each independently selected from H, Br, I, and $NO_2$. In another embodiment, $R_1$, $R_2$, $R_4$, $R_5$, $R_6$, $R_8$, $R_{10}$, $R_{11}$ and $R_{13}$ of Formula 1 are all H, $R_3$ is selected from H, $CH_3$, OH, $OCH_3$ and $NO_2$, $R_7$ and $R_9$ are each independently selected from H and $OCH_3$, $R_{12}$ is selected from H, Br, I and $NO_2$, and $R_{14}$ is selected from H, OH, Cl, Br, I and $NO_2$.

The type of compositions include any known in the art, including but not limited to liquid compositions formulated for intravenous or other parenteral administration, compositions formulated for topical administration, and compositions formulated for oral administration, such as, for example, tablets, pills, capsules, lozenges, granules. In certain embodiments, the compositions comprise between 0.4 millimoles and 30 millimoles of a disclosed compound, such as between 1 millimole and 10 millimoles, or such as 1, 2, 5, 10, 20, 25, or 30 millimoles. The disclosed compositions may further comprise one or more excipients appropriate to the formulation. Intravenous formulations may comprise at least one of: an appropriate solvent, such as water; a salt or ions such as sodium chloride, potassium chloride, potassium ion, sodium ion, chloride ion; a sugar such as glucose and sucrose; a buffer; other excipients, such as DMSO. Topical formulations may include but are not limited to ointments, creams, lotions, salves and comprise at least one of: an appropriate vehicle; a penetration enhancer, such as DMSO and related analogues; and an emulsifier. Tablets may comprise at least one excipient such as, for example: a filler (e.g. starches, lactose, sucrose, glucose); a binder (e.g. carboxymethylcellulose, gelatin, polyvinylpyrrolidone, sucrose); a disintegrating agent (e.g. calcium carbonate, alginic acid, sodium carbonate); a wetting agent (e.g. cetyl alcohol, and glycerol monostearate, sodium lauryl sulfate); a buffering agent; a lubricant (e.g. talc, calcium stearate, magnesium stearate, solid polyethylene glycols, sodium lauryl sulfate); and a coating.

In certain embodiments, the composition comprises $^{64}Zn_e$-asp; in further embodiments, the composition further comprises 10% rubidium salt containing Rb-85.

In another aspect, this disclosure provides methods comprising administering a therapeutically effective amount of a disclose composition to a subject in need thereof, to treat NDD, particularly PD.

In another aspect, this disclosure provides a method of treating a patient in need thereof comprising administering a therapeutically effective amount of a disclose composition to said patient. In certain embodiments, the condition treated is a neurodegenerative disease, such as Parkinson's disease. In an embodiment, a method is disclosed of treating or slowing the progress of a neurodegenerative disease, such as Parkinson's disease, comprising administering: a therapeutically effective amount of a composition comprising a $^{85}Rb$-enriched rubidium compound of Formula 1 and/or a $^{64}Zn_e$-containing salt, complex or compound, with or without a conventional form of NDD or PD therapy. In certain embodiments, the method comprises administering: a therapeutically effective amount of a composition that comprises a $^{64}Zn_e$-containing compound, salt, or complex; a therapeutically effective amount of a composition that comprises an $^{85}Rb$-enriched rubidium compound of Formula 1; and a composition that comprises both a $^{64}Zn_e$-containing compound, salt or complex and an $^{85}Rb$-enriched rubidium compound. In further embodiments, such a composition includes at least one excipient. In certain embodiments, the $^{64}Zn_e$-containing compound and $^{85}Rb$-enriched rubidium compound are present in certain ratios to each other, such as 90% $^{64}Zn_e$-containing compound and 10% $^{85}Rb$-enriched rubidium compound of Formula 1, such as 90% $^{64}Zn_e$-asp and 10% $^{85}Rb_e$-E2, where the percentage is with respect to masses of the elements. In other embodiments, the $^{64}Zn_e$-containing salt, complex or compound is $^{64}Zn_e$-aspartate. In some embodiments, the compound is a peptide that is up to 20 amino acids long.

According to a first aspect of the invention, there is provided a method of treating, preventing, or slowing the progression of a neurodegenerative disease comprising administering to a subject in need thereof a therapeutically effective amount a composition comprising: an $^{85}Rb_e$ compound of the following formula:

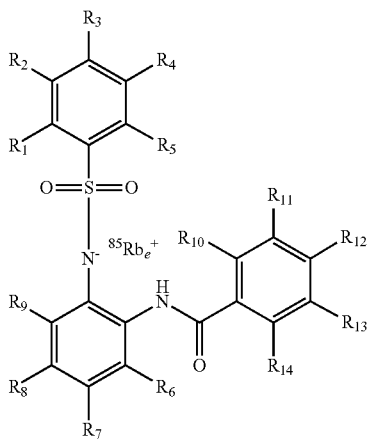

Formula 1 wherein each of $R_1$ through $R_{14}$ is independently selected from H, OH, F, Cl, Br, I, $C_1$-$C_6$ alkyl, $C_1$-$C_6$ alkoxy, and $NO_2$ and the $^{85}Rb_e$ is at least 75% $^{85}Rb$, and a salt, and/or a compound or complex of $^{64}Zn_e$.

In some embodiments of the method of the first aspect, the $^{85}Rb_e$ is at least 90% $^{85}Rb$ and/or the $^{64}Zn_e$ is at least 90% $^{64}Zn$.

In some embodiments of the method of the first aspect, $R_1$, $R_2$, $R_4$-$R_6$, $R_8$, $R_{10}$, $R_{11}$, and $R_{13}$ are all H.

In some embodiments of the method of the first aspect, $R_3$ is selected from H, $CH_3$, $OCH_3$, and $NO_2$, $R_7$ and $R_9$ are each independently selected from H and $OCH_3$, and $R_{12}$ and $R_{14}$ are each independently selected from H, Br, I, and $NO_2$.

In some embodiments of the method of the first aspect,
a) $R_3$ is $CH_3$ and $R_7$, $R_9$, $R_{12}$, and $R_{14}$ are all H,
b) $R_3$, $R_7$, $R_9$, $R_{12}$, and $R_{14}$ are all H,
c) $R_3$ is $CH_3$, $R_{14}$ is Cl, and $R_7$, $R_9$, and $R_{12}$ are all H,
d) $R_3$ is $CH_3$, $R_{14}$ is OH and $R_7$, $R_9$, and $R_{12}$ are all H,
e) $R_{14}$ is OH and $R_3$, $R_7$, $R_9$, and $R_{12}$ are all H,
f) $R_3$ is OH and $R_7$, $R_9$, $R_{12}$, and $R_{14}$ are all H,
g) $R_{14}$ is $NO_2$ and $R_3$, $R_7$, $R_9$, and $R_{12}$ are all H,
h) $R_{12}$ is Br, $R_{14}$ is $NO_2$ and $R_3$, $R_7$, and $R_9$ are all H,
i) $R_3$ and $R_9$ are both $OCH_3$, $R_{12}$ is Br, $R_{14}$ is $NO_2$ and $R_7$ is H, or
j) $R_3$ and $R_9$ are both $OCH_3$, $R_{14}$ is $NO_2$ and $R_7$ and $R_{12}$ are both H.

In some embodiments of the method of the first aspect the composition further comprises at least one excipient.

In some embodiments of the method of the first aspect, $R_3$ is $CH_3$ and $R_7$, $R_9$, $R_{12}$, and $R_{14}$ are all H.

In some embodiments of the method of the first aspect, the neurodegenerative disorder is Parkinson's disease.

In some embodiments of the method of the first aspect, the composition is administered intravenously to the subject.

In some embodiments of the method of the first aspect, the composition is administered intraperitoneally to the subject.

In some embodiments of the method of the first aspect, the composition is administered orally to the subject.

In some embodiments of the method of the first aspect, the method further comprises administering before, simultaneously with, or after the administration of said composition a formulation comprising one or more other therapeutic agent for treating a neurodegenerative disorder.

In some further embodiments of the method of the first aspect, wherein the neurodegenerative disorder is Parkinson's disease, the method further comprises administering before, simultaneously with, or after the administration of said composition a formulation comprising one or more other anti-Parkinson's disease agent.

In some embodiments of the method of the first aspect, the compound or complex of $^{64}Zn_e$ is part of a zinc finger peptide.

In some embodiments of the method of the first aspect, the subject is a human subject.

In some embodiments of the method of the first aspect, the $^{85}Rb_e$ compound is present in an amount equivalent to between 40 mg $^{85}Rb_e$ and 2400 mg $^{85}Rb_e$.

In some embodiments of the method of the first aspect, the compound or complex of $^{64}Zn_e$ is present in an amount equivalent to between doses of $^{64}Zn_e$ (by metal) ranges from 0.1 to 1.5 mg of pure $^{64}Zn_e$ per 1 kg of human body weight.

In some embodiments of the method of the first aspect, the compound or complex of $^{64}Zn_e$ (by metal) ranges from 1 to 15 mg of pure $^{64}Zn_e$ per 1 kg of human body weight.

BRIEF DESCRIPTION OF DRAWINGS

FIG. 1A—relative number of phagocytosing cells. FIG. 1B—phagocytic activity. Key: *—$p \leq 0.05$ versus the group of intact animals; #—$p \leq 0.05$ versus the group of sham-operated animals; ##—$p \leq 0.01$ versus the group of sham-operated animals; +—$p \leq 0.05$ versus the control group of animal models of Parkinsonism; ++—$p \leq 0.01$ versus the control group of animal models of Parkinsonism.

FIG. 8A—relative number of phagocytosing cells (expressed as percentage of cells emitting fluorescence), FIG. 8B—phagocytic activity. Key: *—$p \leq 0.05$ versus the group of intact animals; #—$p \leq 0.05$ versus the group of animal models of Parkinsonism.

FIG. 10A shows the relative number of phagocytosing cells (expressed as the percentage of cells emitting fluorescence). FIG. 10B shows phagocytic activity. Key: *—$p \leq 0.05$ versus the group of intact animals. Key: #—$p \leq 0.05$ versus the group of animal models of Parkinsonism.

FIG. 14A—relative number of phagocytosing cells, FIG. 14B—phagocytic activity. Key: *—$p \leq 0.05$ versus the group of intact animals; #—$p \leq 0.05$ versus the group of animal models of Parkinsonism.

FIG. 30A: decapitation; FIG. 30B: opening of the cranium; FIG. 30C: extracted brain tissue in the absence of hemorrhage.

FIG. 51A displays A trajectory map and FIG. 51B displays a map of cumulative time spent by an animal in a given location in the apparatus for 5 minutes.

FIG. 52 is a graphical representation of the scheme of the experiment in the study of therapeutic effects of 64Zn-asp on behavioral and motor functions and apomorphine-induced rotational behavior in experimental parkinsonism (Example 7).

FIG. 53A and FIG. 53B show results of apomorphine tests in LPS rat models of parkinsonism before and after administration of 64Zn-asp. FIG. 53A: mean number of rot./30 min in the 1st and 2nd apomorphine tests, M±SD; FIG. 53B: percentage ratio of rats with increased and decreased number of rotations per 30 min between the 1st and 2nd apomorphine tests.

FIG. 54A-FIG. 54O show immunohistochemical identification of neurons with tyrosine hydroxylase activity in the midbrain of LPS rat models of parkinsonism after administration of 64Zn-asp. TH-positive staining (brown). Oc. 40, ob. 10. FIG. 54A (animal 1), FIG. 54B (animal 2), FIG. 54C (animal 3), FIG. 54A-FIG. 54C: Group I—intact rats (n=3); FIG. 54D (animal 1), FIG. 54E (animal 2), FIG. 54F (animal 3), FIG. 54D-FIG. 54F: Group II—sham-operated rats+H2O (n=3); FIG. 54G (animal 1), FIG. 54H (animal 2), FIG. 54I (animal 3), FIG. 54G-FIG. 54I: Group III—sham-operated rats+64Zn-asp (n=3); FIG. 54J (animal 1), FIG. 54K (animal 2), FIG. 54L (animal 3), FIG. 54J-FIG. 54L: Group V—LPS+H2O (n=3); FIG. 54M (animal 1), FIG. 54N (animal 2), FIG. 54O (animal 3), FIG. 54M-FIG. 54O: Group VI—LPS+64Zn-asp (n=3).

FIG. 59A: total distance travelled by animals by groups; time spent in the outer perimeter; FIG. 59B: and inner perimeter; FIG. 59C and FIG. 59D; total number of rearings; FIG. 59E: total number of defecations.

(FIG. 60A) total distance travelled by animals; (FIG. 60B) time spent in the open arms; (FIG. 60C) time spent in the closed arms; (FIG. 60D) total number of entries.

Note: #$p \leq 0.05$ vs. intact animals, $ $p \leq 0.05$ vs. sham-operated animals, * $p \leq 0.05$ vs. animal models of Parkinson's disease.

FIG. 65A and FIG. 65B show the therapeutic effects of 64Zn-asp on phagocytic activity of microglia in LPS rat models of Parkinson's disease. FIG. 65A—relative number of phagocytic cells, FIG. 65B—phagocytic activity. #—$p \leq 0.05$ vs intact animals; $—$p \leq 0.05$ vs. sham-operated animals, *—$p \leq 0.05$ vs. control animal models of Parkinson's disease.

Figure 66:
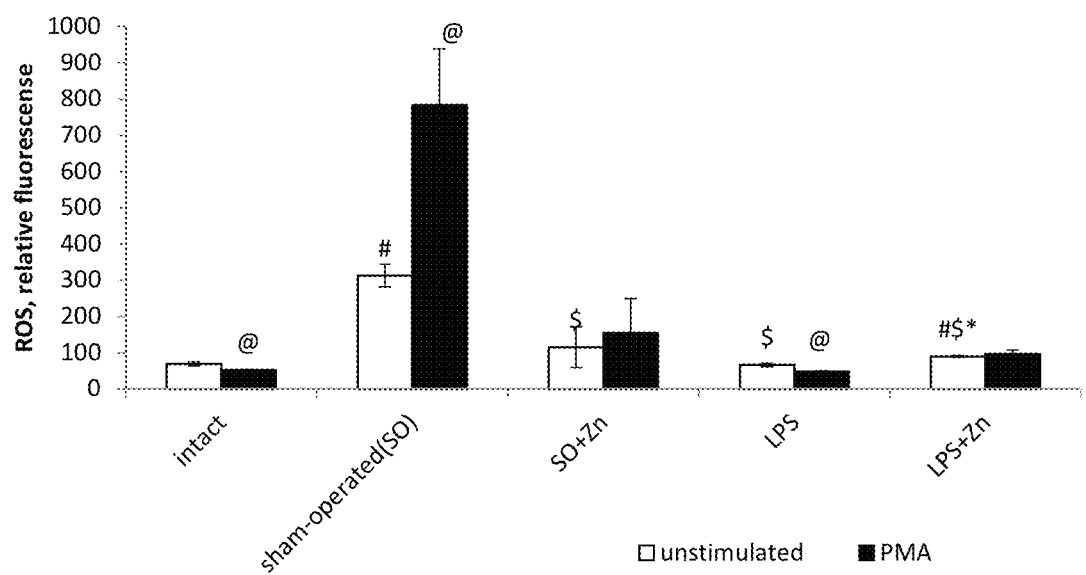

FIG. 66 shows the therapeutic effects of 64Zn-asp on oxidative metabolism of microglia in LPS rat models of Parkinson's disease. #—$p \leq 0.05$ vs intact animals; $ $p \leq 0.05$ vs. sham-operated animals, *$p \leq 0.05$ vs. control animal models of Parkinson's disease, @—$p \leq 0.05$ vs. unstimulated sample.

Figure 67A:
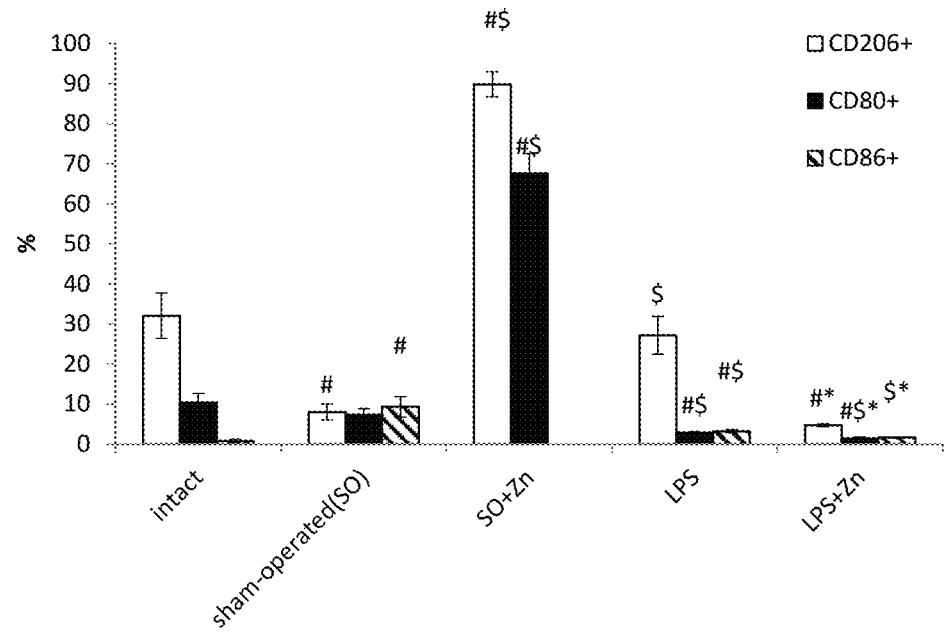
Figure 67B:
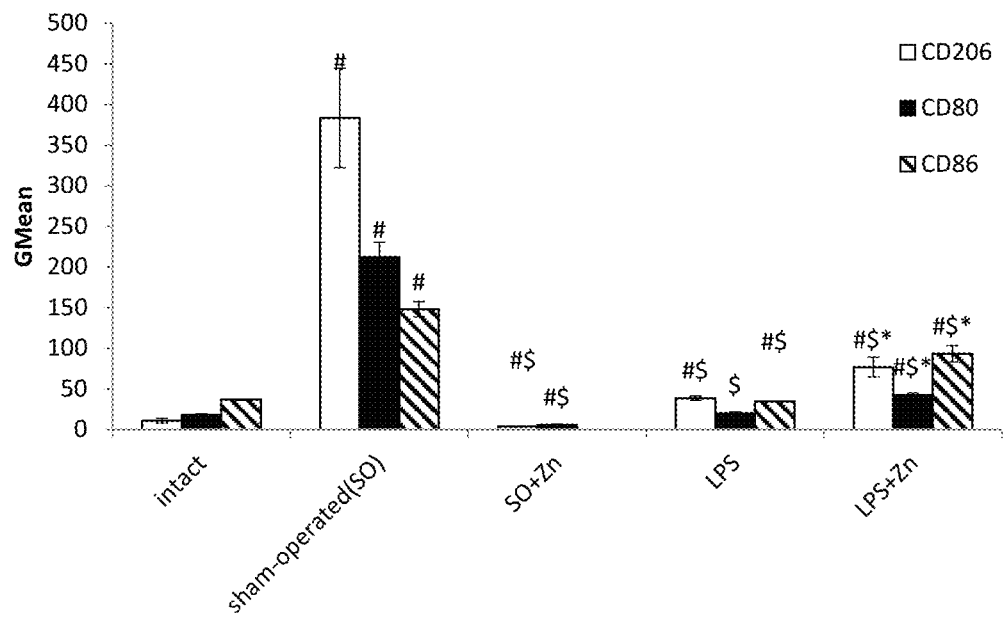

FIG. 67A and FIG. 67B show the expression of phenotypic markers in microglia population in LPS rat models of experimental parkinsonism treated with 64Zn-asp. FIG. 67A—the number of expressing cells in the population analyzed, FIG. 67B—the expression level. #—$p \leq 0.05$ vs. intact animals; $—$p \leq 0.05$ vs. sham-operated animals, *—$p \leq 0.05$ vs. control animal models of Parkinson's disease.

Figure 68A:
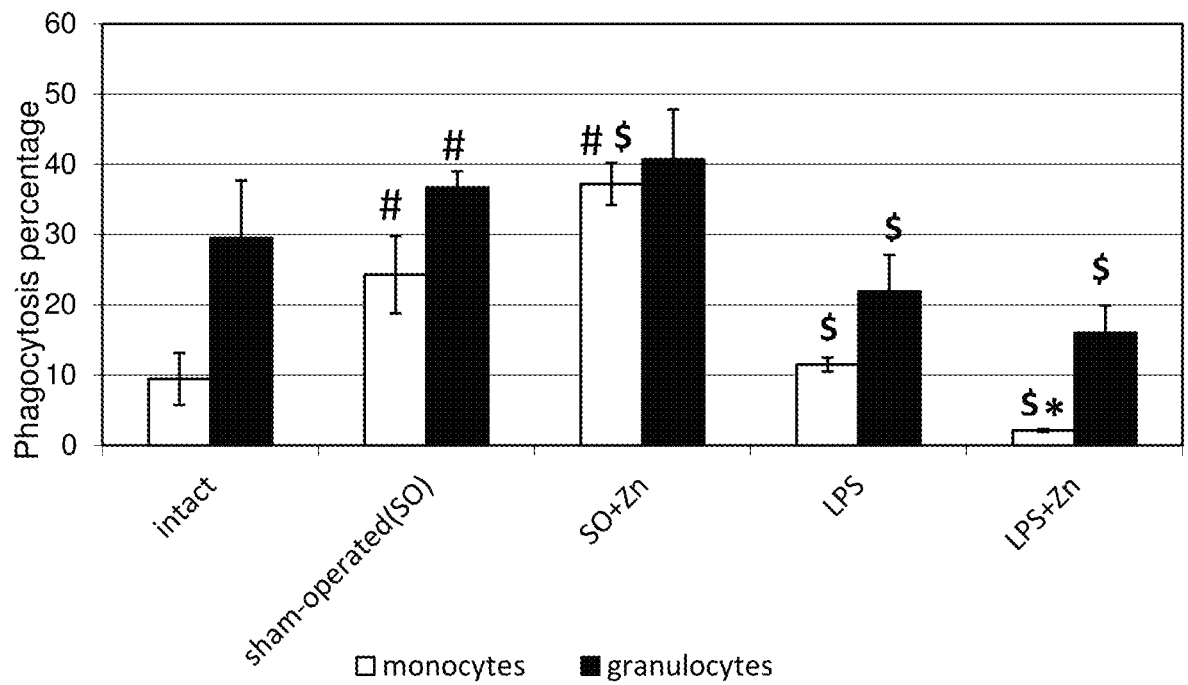
Figure 68B:
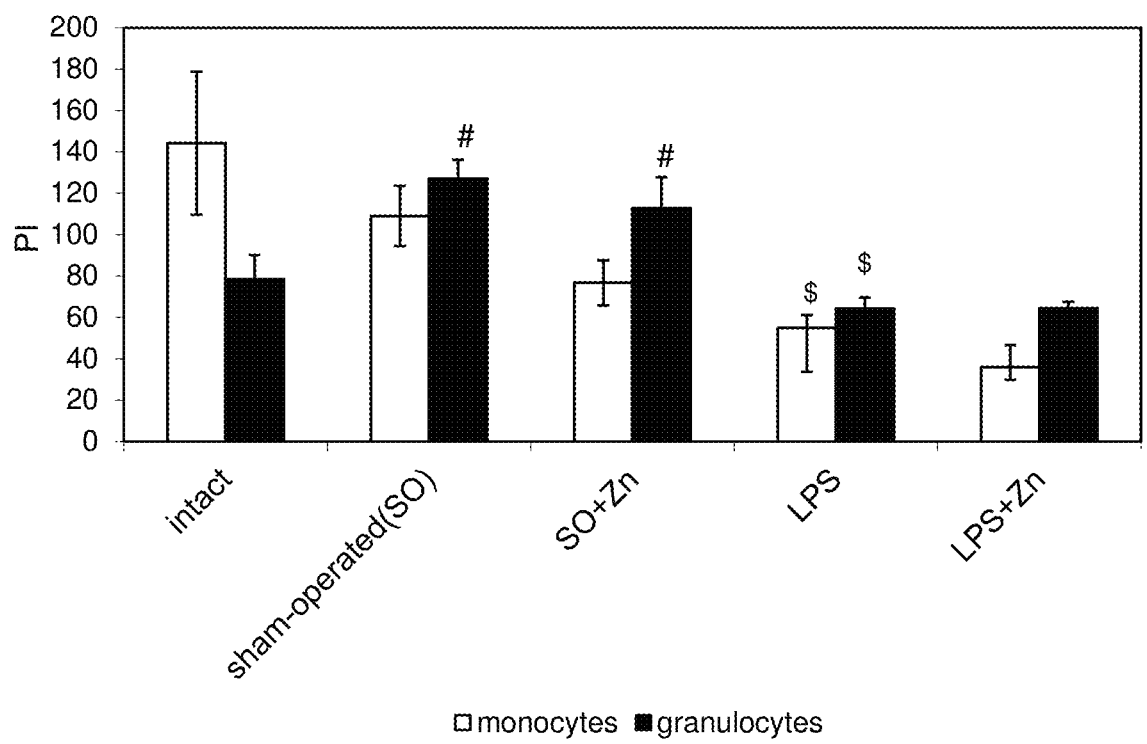

FIG. 68A and FIG. 68B show the therapeutic effects of 64Zn-asp on phagocytic activity of circulating monocytes and granulocytes in LPS rat models of Parkinson's disease.

FIG. 68A—relative number of phagocytic cells, FIG. 68B—phagocytic activity. #—$p \leq 0.05$ vs. intact animals; $—$p \leq 0.05$ vs. sham-operated animals, *—p K 0.05 vs. control animal models of Parkinson's disease.

Figure 69A:
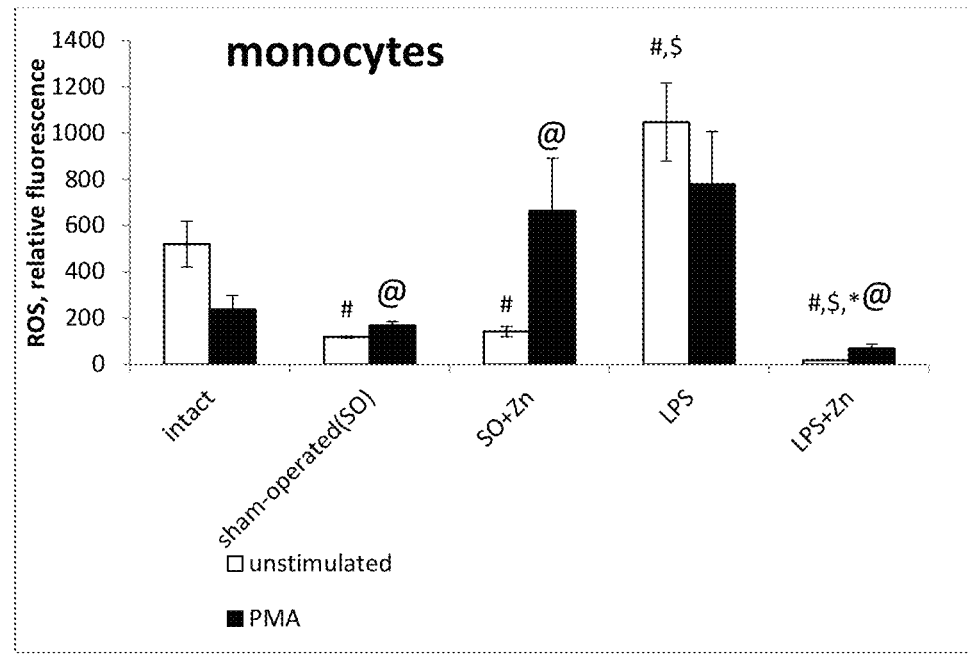
Figure 69B:
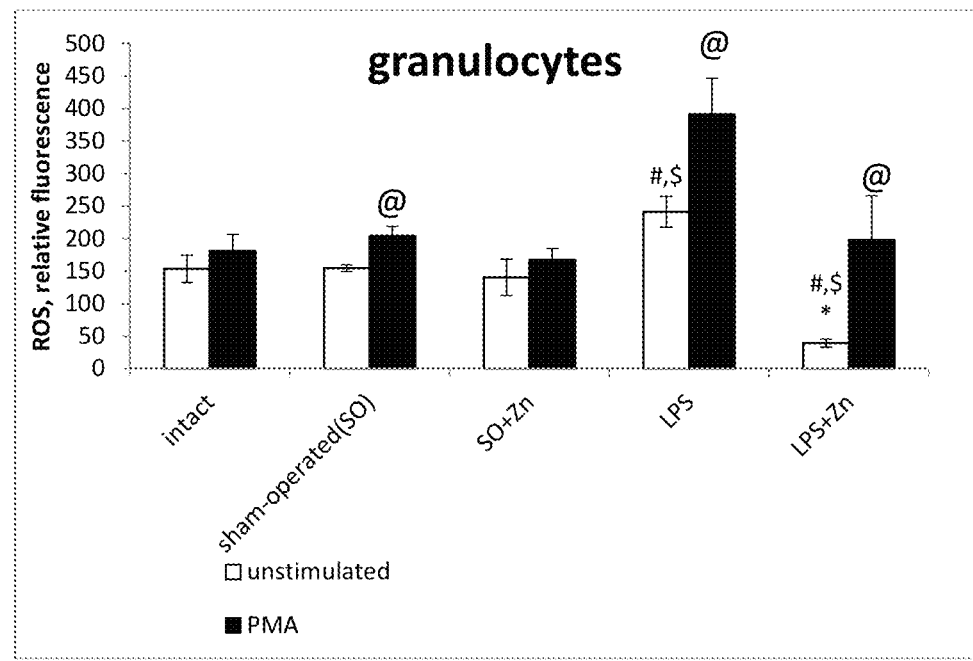
Figure 70A:
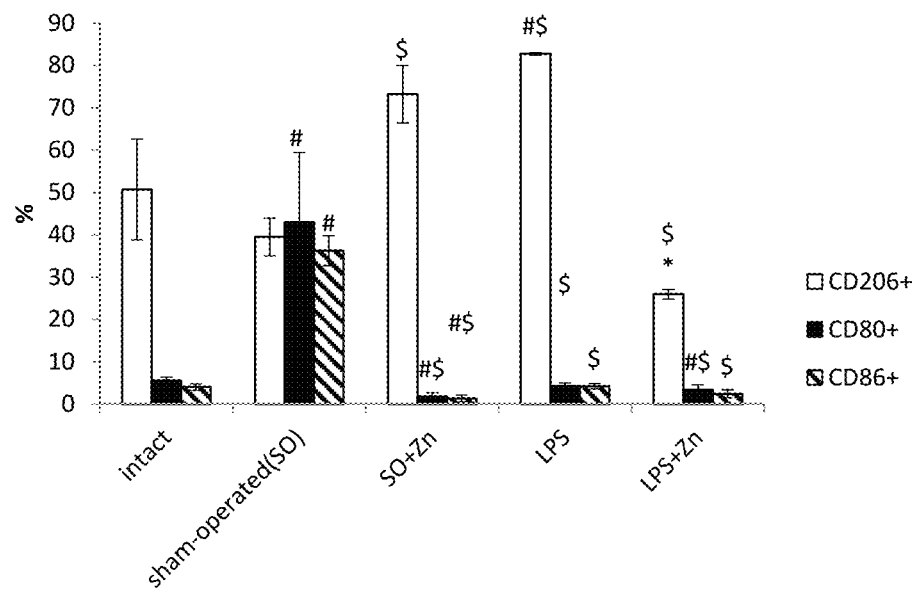
Figure 70B:
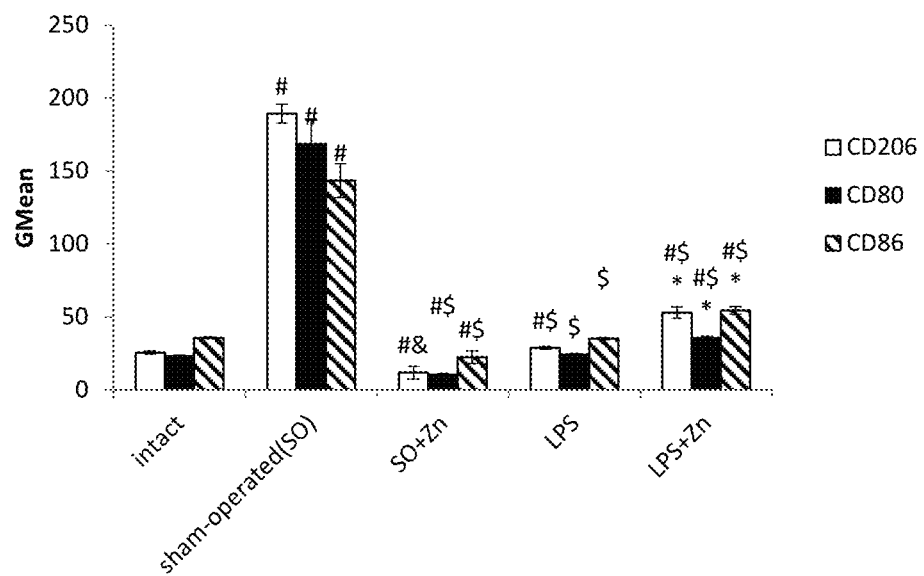
Figure 71A:
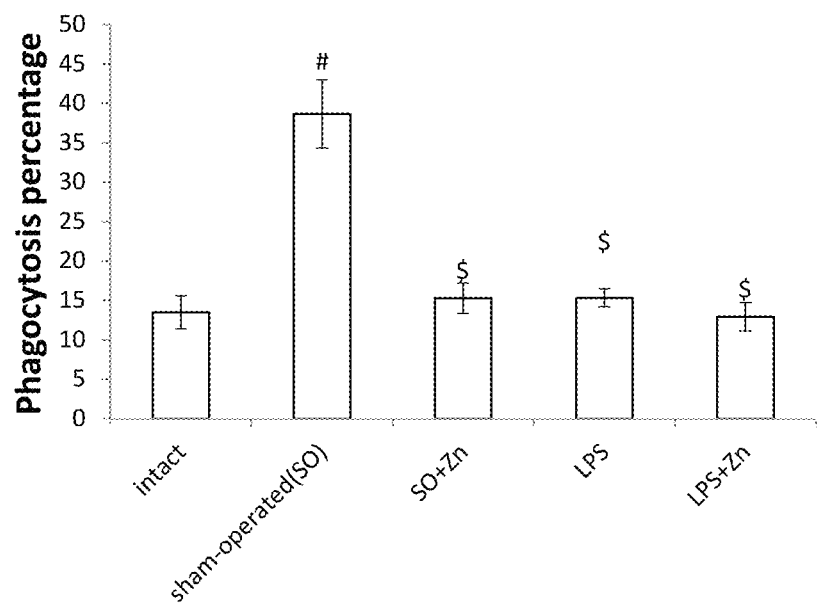
Figure 71B:
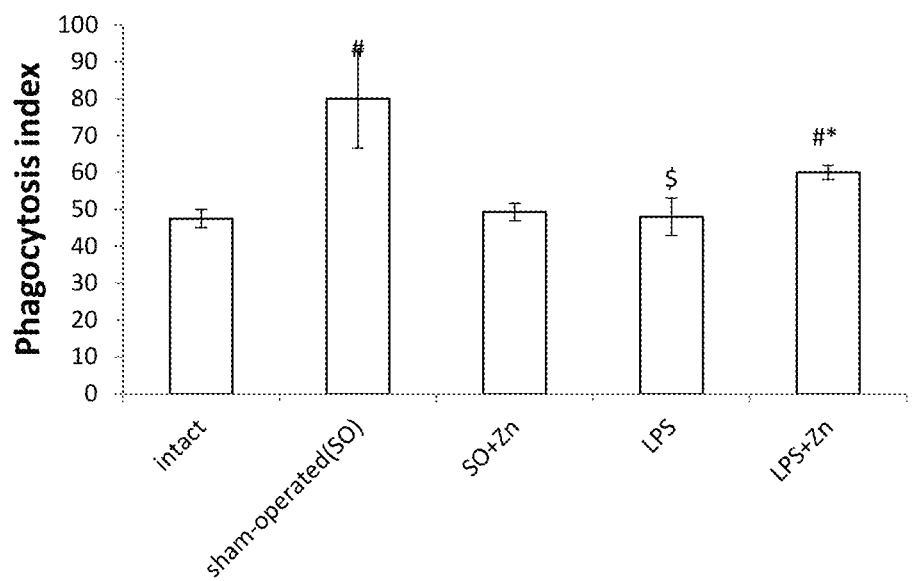

FIG. 69A and FIG. 69B show the therapeutic effects of 64Zn-asp on oxidative metabolism of circulating monocytes (FIG. 69A) and granulocytes (FIG. 69B) in LPS rat models of Parkinson's disease. #—$p \leq 0.05$ vs intact animals; $—$p \leq 0.05$ vs. sham-operated animals, *—$\leq 0.05$ vs. control animal models of Parkinson's disease, @—$p \leq 0.05$ vs. unstimulated sample FIG. 70A and FIG. 70B show the expression of phenotypic markers by circulating phagocytes in LPS rat models of experimental parkinsonism treated with 64Zn-asp. FIG. 70A—the number of expressing cells in the population analyzed, FIG. 70B—the expression level. #—$p \leq 0.05$ vs. intact animals; $—$p \leq 0.05$ vs. sham-operated animals, *—$p \leq 0.05$ vs. control animal models of Parkinson's disease FIG. 71A and FIG. 71B show the therapeutic effects of 64Zn-asp on phagocytic activity of peritoneal macrophages in LPS rat models of Parkinson's disease. FIG. 71A—relative number of phagocytic cells, FIG. 71B—phagocytic activity. #—$p \leq 0.05$ vs. intact animals; $—$p \leq 0.05$ vs. sham-operated animals, *—$p \leq 0.05$ vs. control animal models of Parkinson's disease.

FIG. 72 shows the therapeutic effects of 64Zn-asp on oxidative metabolism of peritoneal macrophages in LPS rat models of Parkinson's disease. #—$p \leq 0.05$ vs. intact animals, $—$p \leq 0.05$ vs. sham-operated animals, *—$\leq 0.05$ vs. control animal models of Parkinson's disease, @—$p \leq 0.05$ vs. unstimulated sample.

Figure 73B:
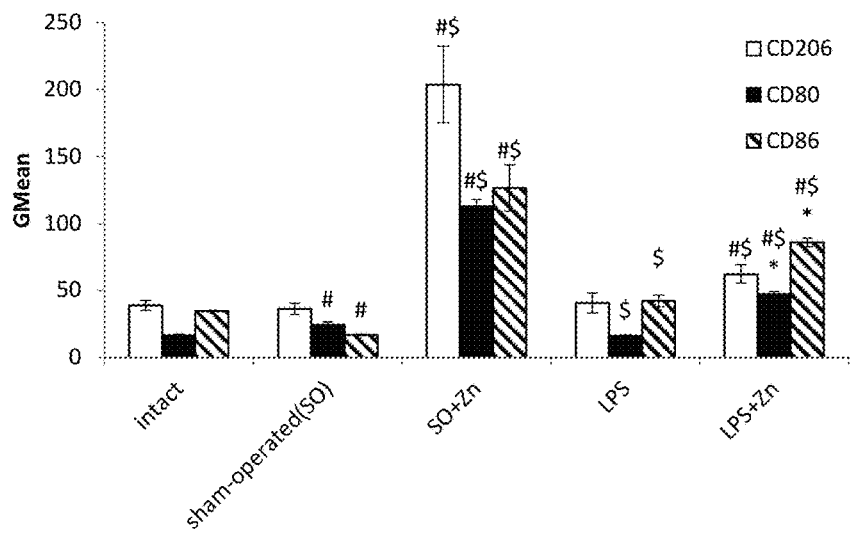

FIG. 73A and FIG. 73B show the expression of phenotypic markers by peritoneal macrophages in LPS rat models of experimental parkinsonism treated with 64Zn-asp. FIG. 73A—the number of expressing cells in the population analyzed, FIG. 73A—the expression level. #—$p \leq 0.05$ vs. intact animals; $—$p \leq 0.05$ vs. sham-operated animals, *—$p \leq 0.05$ vs. control animal models of Parkinson's disease.

Figure 74:
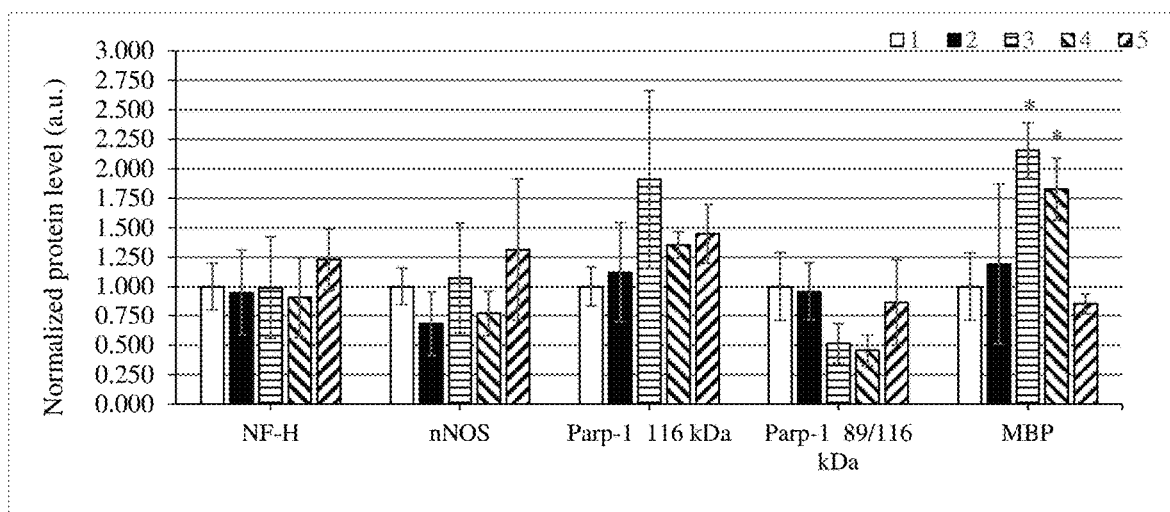

FIG. 74 shows neuronal nitric oxide synthase expression in astrocytes in LPS rat models of parkinsonism treated with 64Zn-asp. @—$p \leq 0.05$ vs. control animal models of Parkinson's disease. 1 is control; 2 is Sham-operated+H$_2$O; 3 is Sham-operated+Zn-asp 1.5 mg/kg; 4 is LPS+H$_2$O; 5 is LPS+Zn-asp 1.5 mg/kg.

DETAILED DESCRIPTION

As used herein, the word "a" or "plurality" before a noun represents one or more of the particular noun.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

As used herein, a subscript "e" appended to an isotope symbol refers to the element enriched for the isotope. For example, "$^{64}Zn_e$" refers to $^{64}$Zn-enriched zinc, and "$^{85}Rb_e$" refers to $^{85}$Rb-enriched rubidium.

"Compound 1" is referred to herein as the $^{85}$Rb-enriched rubidium organic salt of N-benzoyl-N'-(4-toluenesulfonyl)-o-phenylenediamine, as "E2+$^{85}Rb_e$," or as "$^{85}Rb_e$-E2." "E2" refers to N-benzoyl-N'-(4-toluenesulfonyl)-o-phenylenediamine.

As used herein, $^{64}Zn_e$ is zinc that is at least 50% $^{64}$Zn. Preferably, the zinc compounds, complexes and salts of the compositions for use in the disclosed methods comprise $^{64}Zn_e$ that is at least 75% $^{64}$Zn, such as at least 80%, 85%, 90%, 95%, or 99% $^{64}$Zn.

The term "effective amount" or "a therapeutically effective amount" refers to an amount of an agent that provides a beneficial effect to a patient. The term "effective amount" or "a therapeutically effective amount" refers to an amount of an agent that provides the desired biological, therapeutic, and/or prophylactic result. That result can be reduction, amelioration, palliation, lessening, delaying, and/or alleviation of one or more of the signs, symptoms, or causes of a disease or disorder in a patient, or any other desired alteration of a biological system. An effective amount can be administered in one or more administrations.

As used herein, a "patient" and a "subject" are interchangeable terms and may refer to a human patient or an animal subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Neurodegenarative Disorders

Neurodegenerative disorders (NDD), including Parkinson's disease (PD), are pathological conditions induced by an inflammatory process. Calabrese V, et al. Free Radic Biol Med. 2017; 115:80-91. doi: 10.1016/j.freeradbiomed.2017.10.379.1; Franceschi C, et al., Trends Endocrinol Metab. 2017; 28(3):199-212. doi: 10.1016/j.tem.2016.09.005; Monti D, et al. Mech Ageing Dev. 2017; 165(Pt B):129-138. doi: 10.1016/j.mad.2016.12.008. The development of NDD is characteristic for elderly people. The pathophysiological basis of this phenomenon has been termed as "inflammaging", which is a chronic, low-grade systemic inflammatory process accompanied by increased expression of inflammation mediators in tissues, organs and body fluids, as well as a pro-inflammatory shift in the metabolic profile of immune system cells, effectors of inborn immunity in particular, such as mono- and polymorphonuclear phagocytes (monocytes, macrophages and neutrophils) Franceschi C, Campisi J. J Gerontol A Biol Sci Med Sci. 2014 June; 69 Suppl 1:S4-9. doi: 10.1093/gerona/glu057. One of the most important inflammation mediators are reactive oxygen species (ROS) which perform a number of important biological functions, both in the normal condition and in the development of pathological conditions. Myeloid cells of the immune system (monocytes, neutrophils and macrophages) are the main sources of ROS. Monocytes and neutrophils are myeloid cells constantly circulating in the peripheral blood. Macrophages are resident cells that are present in all tissues without exception and serve as sentinels of the immune system. They are formed via differentiation of monocytes. In the normal condition, ROS function as signaling molecules that regulate cellular metabolism. It is ROS-mediated signaling that is involved in reparative processes in tissues associated with the stimulation of angiogenesis and differentiation of stem tissue elements necessary for the reconstruction of tissue lesions. ROS have a bactericidal function and are effector molecules of both intracellular and extracellular killing of pathogenic microorganisms. However, enhancement of ROS production leads to the development of abnormal cellular signaling and has a significant effect on the properties of proteins causing problems in their folding (formation of their functional tertiary structure), formation of protein aggregates and, as a consequence, abnormality/loss of their physiological functions and/or acquisition of pathological functions. Among all the proteins in the body, those that incorporate sulfur-containing amino acids—cysteine and methionine—are the most important targets for ROS. Ahmad S, et al. Front Biosci (Schol Ed). 2017; 9:71-87. Luo S, Levine R L. et al., FASEB J. 2009; 23(2):464-72. doi: 10.1096/fj.08-118414. Cysteine and methionine serve as ROS scavengers, thus preventing the development of oxidative stress. A mechanism of antioxidant action of these amino acids consists in immediate restoration of their oxidized forms by reductase present in all cells of the body. For example, the oxidized form of methionine is restored by methionine sulfoxide reductase (MSR). However, with aging, synthesis of reductase, including MSR, is significantly reduced which is one of the reasons for the realization of pathogenic effect of ROS and the development of inflammaging.

ROS are also pathogenetic factors of PD. The targets of pathogenic action of ROS in Parkinsonism are a number of methionine-containing proteins in the brain [Herrero M T, et al., Front Neuroanat. 2015; 9:32. doi: 10.3389/fnana.2015.00032; Glaser C B, et al., Biochimica et Biophysica Acta 2005; 1703; 157-169; Danielson S R, Andersen J K. Free Radic Biol Med. 2008 May 15; 44(10):1787-94. doi: 10.1016/j.freeradbiomed.2008.03.005], such as α-synuclein, tyrosine hydroxylase, mitochondrial complex I, PINK1 (PTEN-induced kinase 1), antioxidant DJ-1, etc. For example, ROS-mediated oxidation of methionine as a part of α-synuclein causes a decrease in its ability to exist in the form of protofibrils and promotes aggregation of monomers with the formation of a pathological form of this protein. Initially, it was thought that an inflammatory process accompanying the development of PD is localized exclusively in the brain, where activated microglial cells (resident macrophages of the brain) are the source of ROS. However, recent studies have convincingly demonstrated a systemic nature of the inflammatory process in PD with the involvement of phagocytes localized outside the brain in pathogenesis of the disease. It is proved that the development of PD in both humans and experimental animals is accompanied by pro-inflammatory activation of myeloid cells circulating in peripheral blood (monocytes and neutrophils). There are two types of pathological changes in the quantitative and functional changes in these cells: monocytosis against neutropenia with a pro-inflammatory shift of monocyte functions and neutrophilia against monocytopenia and a sharp increase in the neutrophil oxidative metabolism. Moreover, the quantitative and functional characteristics of circulating myeloid cells are considered as informative markers to monitor a PD course and evaluate the effectiveness of treatment of this pathology. Funk N, et al., Mov Disord. 2013; 28(3):392-5. doi: 10.1002/mds.25300. Grozdanov V, et al., Acta Neuropathol. 2014; 128(5):651-63. doi: 10.1007/s00401-014-1345-4. The development of PD is also closely associated with phagocytes localized within the gastrointestinal tract, including peritoneal macrophages. Studies carried out over the past few years have convincingly demonstrated a relationship between the development of Parkinsonism and dysbiotic disorders of the intestinal microbiota. A simplified scheme of involving dysbiosis in the development of PD looks as follows. Dysbiotic changes in the intestine are accompanied by pro-inflammatory activation of myeloid cells of the intestinal wall and peritoneal phagocytes which become a source of local ROS production. An increase in ROS concentration leads to pathological changes in the aerobic/anaerobic ratio in the intestinal microbiota with an increase in the relative number of aerobic forms of microorganisms against which there are no immune tolerance mechanisms. An increase in the number of pathogenic aerobic microorganisms further enhances the pro-inflammatory activation of myeloid cells. Acceleration of ROS synthesis leads to the formation of polymeric forms of α-synuclein in the intestine. Aggregates of α-synuclein cause pathological changes in the nervous system of the intestine which spread systemically, reaching the brain via a prion-like mechanism. Felice V D, et al., Parkinsonism Relat Disord. 2016; 27:1-8. doi: 10.1016/j.parkreldis.2016.03.012. Obata Y, Pachnis V. Gastroenterology. 2016 v; 151(5):836-844. doi: 10.1053/j.gastro.2016.07.044. Yoo B B, Mazmanian S K. T Immunity. 2017; 46(6):910-926. doi: 10.1016/j.immuni.2017.05.011. Mukherjee A, Biswas A, Das S K. World J Gastroenterol. 2016; 22(25):5742-52. doi: 10.3748/wjg.v22.i25.5742. The most important role of dysbiotic disorders in the pathogenesis of PD is proved by the fact that the only way to prevent this disease is the so-called Mediterranean diet characterized by a high content of complex carbohydrates that stabilize the metabolism of normal intestinal microbiota and polyunsaturated vegetable fatty acids that perform the function of powerful antioxidants. Cassani E., et al. Parkinsonism Relat Disord. 2017; 42:40-46. doi: 10.1016/j.parkreldis.2017.06.007.

See also U.S. patent publication nos. 2019/0105345 and 2016/0153957; and U.S. Pat. Nos. 10,226,484, 9,861,659, and 10,183,041.

Disclosed Compounds, Compositions and Methods

This disclosure relates to methods, compounds and compositions for the treatment of a neurodegenerative disease in a subject, such as Parkinson's disease.

This disclosure provides compounds, separately or in combination with each other, salts and complexes that comprise $^{64}$Zn-enriched zinc, such as $^{64}$Zn-enriched zinc aspartate, or any $^{64}$Zn-enriched zinc amino acids, and an $^{85}$Rb-enriched rubidium organic salt (structure shown below) for use to treat a neurodegenerative disease in a subject, such as Parkinson's disease.

In another aspect, this disclosure provides compositions that comprise $^{64}$Zn-enriched zinc complexes, salts and compounds and/or certain $^{85}$Rb-enriched rubidium compounds to treat neurodegenerative disorders (NDD), in particular, Parkinson's disease (PD). The disclosed composition comprises one or more of the isotope-enriched compounds, optionally in combination with other active ingredients useful to treat NDD. The disclosed composition can be used individually and in combination with other anti-NDD therapies. The disclosed compounds have low toxicity to a patient.

In certain embodiments, this disclosure provides a composition that comprises a compound of Formula 1 to treat neurodegenerative disorders (NDD), in particular, Parkinson's disease (PD).

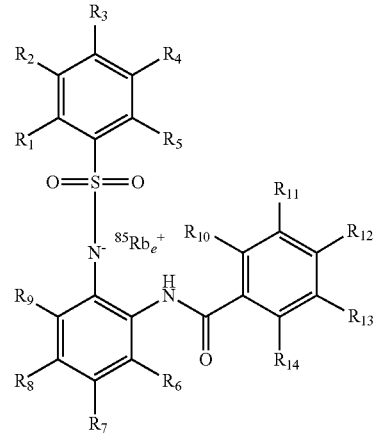

Formula 1

A compound of Formula 1 is a rubidium salt, wherein the rubidium is enriched for $^{85}$Rb and wherein each of $R_1$ through $R_{14}$ is independently selected from H, OH, F, Cl, Br, I, $C_1$-$C_6$ alkyl, $C_1$-$C_6$ alkoxy, and $NO_2$.

In certain embodiments, $R_1$, $R_2$, $R_4$, $R_5$, $R_6$, $R_8$, $R_{10}$, $R_{11}$, and $R_{13}$ of Formula 1 are all H, and
a) $R_3$ is $CH_3$ and $R_7$, $R_9$, $R_{12}$, and $R_{14}$ are all H (Compound 1),
b) $R_3$, $R_7$, $R_9$, $R_{12}$, and $R_{14}$ are all H (Compound 2),
c) $R_3$ is $CH_3$, $R_{14}$ is Cl, and $R_7$, $R_9$, and $R_{12}$ are all H (Compound 3),
d) $R_3$ is $CH_3$, $R_{14}$ is OH and $R_7$, $R_9$, and $R_{12}$ are all H (Compound 4),
e) $R_{14}$ is OH and $R_3$, $R_7$, $R_9$, and $R_{12}$ are all H (Compound 5),
f) $R_3$ is OH and $R_7$, $R_9$, $R_{12}$, and $R_{14}$ are all H (Compound 6),
g) $R_{14}$ is $NO_2$ and $R_3$, $R_7$, $R_9$, and $R_{12}$ are all H (Compound 7),
h) $R_{12}$ is Br, $R_{14}$ is $NO_2$ and $R_3$, $R_7$, and $R_9$ are all H (Compound 8),
i) $R_3$ and $R_9$ are both $OCH_3$, $R_{12}$ is Br, $R_{14}$ is $NO_2$ and $R_7$ is H (Compound 9), or
j) $R_3$ and $R_9$ are both $OCH_3$, $R_{14}$ is $NO_2$ and $R_7$ and $R_{12}$ are both H (Compound 10).

In any of the above compounds of Formula 1, the rubidium preferably is at least 75% $^{85}$Rb, more preferably at least 85% $^{85}$Rb, and still more preferably at least 95% $^{85}$Rb, and in some embodiments is at least 99% $^{85}$Rb, such as 99.8% $^{85}$Rb. "Rb that is N % $^{85}$Rb" refers to Rb of which N % of the Rb atoms are the isotope $^{85}$Rb.

In certain embodiments, $R_1$, $R_2$, $R_4$, $R_5$, $R_6$, $R_8$, $R_{10}$, $R_{11}$, and $R_{13}$ of Formula 1 are all H and the remaining R groups are as defined above. In other embodiments, $R_1$, $R_2$, $R_4$, $R_5$, $R_6$, $R_8$, $R_{10}$, $R_{11}$, and $R_{13}$ of Formula 1 are all H, $R_3$ is selected from H, $CH_3$, $OCH_3$, and $NO_2$, $R_7$ and $R_9$ are each independently selected from H and $OCH_3$, and $R_{12}$ and $R_{14}$ are each independently selected from H, Br, I, and $NO_2$. In another embodiment, $R_1$, $R_2$, $R_4$, $R_5$, $R_6$, $R_8$, $R_{10}$, $R_{11}$ and $R_{13}$ of Formula 1 are all H, $R_3$ is selected from H, $CH_3$, OH, $OCH_3$ and $NO_2$, $R_7$ and $R_9$ are each independently selected from H and $OCH_3$, $R_{12}$ is selected from H, Br, I and $NO_2$, and $R_{14}$ is selected from H, OH, Cl, Br, I and $NO_2$.

In certain embodiments, the composition comprises $^{64}Zn_e$-asp; in further embodiments, the composition further comprises 10% rubidium salt containing Rb-85.

In an exemplary embodiment, Compound 1 of the invention, $R_3$ is $CH_3$ and the remaining R groups are H. This compound is also referred to herein as the $^{85}$Rb-enriched rubidium organic salt of N-benzoyl-N'-(4-toluenesulfonyl)-o-phenylenediamine and as "$^{85}Rb_e$ E2" and "E2+$^{85}Rb_e$." "E2" refers to N-benzoyl-N'-(4-toluenesulfonyl)-o-phenylenediamine. (In the Figures, the terms "E2+$^{85}$Rb", "E2Rb85", and "85RbE2" refer to $^{85}Rb_e$-E2.)

The disclosed compounds are prepared as disclosed herein and/or using chemical synthetic methods known in the art.

Rubidium is a chemical element of the main subgroup of group 1, period 5, of the periodic table, with atomic number 37. $^{85}$Rb is a stable isotope, with a percent natural abundance of 72.2%. That is, naturally occurring rubidium consists of a mixture of rubidium isotopes. In a sample of naturally occurring rubidium, 72.2% of the rubidium atoms are isotope $^{85}$Rb.

As used herein, "$^{85}$Rb-enriched rubidium" is rubidium that consists of more than 72.2% $^{85}$Rb. Thus, in the disclosed compounds, the rubidium is more than 72.2% $^{85}$Rb, such as at least about 75% (e.g. at least 75%), at least about 80% (e.g. at least 80%), at least about 85% (e.g. at least 85%), at least about 90% (e.g. at least 90%), or at least about 95% $^{85}$Rb (e.g. at least 95% $^{85}$Rb).

In certain embodiments of the disclosed compound, composition, and methods, the rubidium is at least about 90% $^{85}$Rb (e.g. at least 90% $^{85}$Rb) and may be over 99% $^{85}$Rb, such as about 99.8% $^{85}$Rb (e.g. 99.8% $^{85}$Rb). The disclosed compositions comprise such $^{85}$Rb-enriched compounds, and the disclosed methods entail administering such compositions.

The term "about" as used herein indicates plus or minus 3% of the subject amount (e.g., "about 80%" refers to the range from 77.6% to 82.4%).

In another aspect, this disclosure provides a method of treating or slowing the progress of a neurodegenerative disease, such as Parkinson's disease, comprising administering: a therapeutically effective amount of a composition comprising: a $^{85}$Rb-enriched rubidium compound of Formula 1 and/or a $^{64}Zn_e$-containing salt, complex or compound, either alone or in combination with a conventional form of NDD or PD therapy. In certain embodiments, the method comprises administering: a therapeutically effective amount of a composition that comprises a $^{64}Zn_e$-containing compound, salt, or complex; a therapeutically effective amount of a composition that comprises an $^{85}$Rb-enriched rubidium compound of Formula 1; or a composition that comprises both a $^{64}Zn_e$-containing compound, salt or complex and an $^{85}$Rb-enriched rubidium compound. In further embodiments, such a composition includes at least one excipient. In certain embodiments, the $^{64}Zn_e$-containing compound and $^{85}$Rb-enriched rubidium compound are present in certain ratios to each other, such as 90% $^{64}Zn_e$-containing compound and 10% 85Rb-enriched rubidium compound of Formula 1, such as 90%$^{64}Zn_e$-asp and 10% $^{85}Rb_e$-E2, where the percentage is with respect to masses of the elements. In other embodiments, the $^{64}Zn_e$-containing salt, complex or compound is $^{64}Zn_e$-aspartate. In some embodiments, the compound is a peptide that is up to 20 amino acids long.

In certain embodiments, the disclosed composition comprises a $^{64}Zn_e$-aspartate chelate complex. In some embodiments, the compound is a protein or peptide structure in the form of zinc finger, which contains one or two zinc ions, and one or about 20 amino acids. In such structure, zinc may act as a structure stabilizer.

In composition comprising both a $^{64}Zn_e$ and a $^{85}Rb_e$ compound, in certain embodiments, the ratio of $^{64}Zn_e$ and $^{85}Rb_e$ components is: 9 parts (by weight) of $^{64}Zn_e$ and 1 part of $^{85}Rb_e$; in other embodiments, the ratio is 7 parts (by weight) of $^{64}Zn_e$ and 3 parts of $^{85}Rb_e$. In some embodiments, the ratio is from 1 to 7 parts (by weight) of $^{64}Zn_e$ and from 3 to 9 parts (by weight) of $^{85}Rb_e$, in compositions comprising both a $^{64}Zn_e$ and a $^{85}Rb_e$ compound.

Instead of one composition comprising both, it is also provided two compositions, each comprising either a $^{64}Zn_e$ or a $^{85}Rb_e$ compound. In certain embodiments, even though these are two separate compositions, the ratio the ratio of $^{64}Zn_e$ and $^{85}Rb_e$ components is: 9 parts (by weight) of $^{64}Zn_e$ and 1 part of $^{85}Rb_e$; in other embodiments, the ratio is 7 parts (by weight) of $^{64}Zn_e$ and 3 parts of $^{85}Rb_e$. In some embodiments, the ratio is from 1 to 7 parts (by weight) of $^{64}Zn_e$ and from 3 to 9 parts (by weight) of $^{85}Rb_e$, in compositions comprising both a $^{64}Zn_e$ and a $^{85}Rb_e$ compound.

In certain embodiments, a composition is provided that comprises one or more compounds of Formula 1, such as any of Compounds 1-10 (e.g. the $^{85}$Rb-enriched rubidium salt of N-benzoyl-N'-(4-toluenesulfonyl)-o-phenylenediamine), and optionally also contains one or more other anti-NDD drugs, for example, one or more anti-PD drugs.

In some embodiments, the disclosed composition comprises, in addition to a compound of Formula 1, a $^{64}Zn_e$-containing compound, salt or complex, such as $^{64}Zn_e$ aspartate (also referred to herein as "$^{64}Zn_e$-asp"), $^{64}Zn_e$ glutamate, or a $^{64}Zn_e$ salt of another amino acid, such as any of the 18 other most common naturally occurring amino acids.

A method is disclosed that comprises administering to a human or to a veterinary animal a disclosed compound or composition and optionally at least one other form of anti-NDD therapy. The method may be used to treat an NDD (e.g., PD) or to slow the advance of the disease in a patient who has the disease.

In certain embodiments, a compound comprising $^{85}$Rb-enriched rubidium salt of N-benzoyl-N'-(4-toluenesulfonyl)-o-phenylenediamine (Compound 1) is disclosed, wherein the enriched rubidium is 99.8% $^{85}$Rb.

Combination Therapies

In various embodiments, the disclosed composition is administered before, simultaneously with, or after the administration of another NDD or PD therapy or treatment. In an embodiment, when not administered simultaneously, the interval between administrations is about 48 hours or less, such as 48 hours or less, 36 hours or less, or 24 hours or less.

In other embodiments, the disclosed composition comprises a $^{64}Zn_e$-containing compound, salt or complex, such as $^{64}Zn_e$ aspartate, $^{64}Zn_e$ glutamate, or a $^{64}Zn_e$ salt of another amino acid, such as any of the 18 other most common naturally occurring amino acids, and does not contain a compound of Formula 1. In some embodiments, such a composition contains one or more additional anti-NDD agents, such as an anti-PD agent.

In certain embodiments, in a composition that contains both the $^{85}$Rb-enriched rubidium salt of formula I and an anti-PD drug, the $^{85}$Rb$_e$ salt at a suitable dose, and a conventional, prior art anti-NDD drug, such as a conventional, prior art anti-PD drug, is present at a dose that is, for example, between 0.05 and 2.5 times the approved dosage (or at the dosage that the anti-NDD drug would have been prescribed if not administered in conjunction with a disclosed compound).

The anti-PD drugs may be any anti-PD drugs, such as, for example, anti-PD agent, for example, one or more drugs selected from L-dopa (optionally in combination with carbidopa), melevodopa, or etilevodopa; dopamine agonists, such as ropinirole, pramipexole, rotigotine, bromocriptine, pergolide, dihydroergocryptine mesylate, cabergoline, piribedil, and apomorphine; monoamine oxidase B inhibitors, such as rasagiline, selegiline, opicapone, and safinamide; catechol-O-methyltransferase inhibitors, such as entacapone, tolcapone; anticholinergics, such as trihexyphenidyl, benztropine biperiden, metixene, procyclidine, profenamine, dexetimide, phenglutarimide, mazaticol, bornaprine, tropatepine, etanautine, orphenadrine (chloride), etybenzatropine, budipine; and amantadine. The anti-PD drug composition optionally contains one or more adjuvant agents.

Formulating and Administering Compositions

The disclosed compositions include those conventional forms known in the art for administration to humans or animals.

In some embodiments, the disclosed compositions comprise at least one pharmaceutically acceptable vehicle or excipient. These include, for example, diluents, fillers, disintegrants, solubilizing agents, dispersing agents, preservatives, wetting agents, preservatives, stabilizers, buffering agents (e.g. phosphate, citrate, acetate, tartrate), suspending agents, emulsifiers, and penetration enhancing agents such as DMSO, as appropriate.

In certain embodiments, the composition may additionally contain suitable diluents, glidants, lubricants, acidulants, stabilizers, fillers, binders, plasticizers or release aids and other pharmaceutically acceptable excipients.

The disclosed compositions, in some embodiments, are solutions for injection, such as intravenous injection. Water is preferably used as a dosing vehicle and diluent in an injectable composition. Other pharmaceutically acceptable solvents and diluents may also be used in addition to or instead of water, such as saline, glycerol and ethanol.

A complete description of pharmaceutically acceptable excipients can be found, for example, in Remington's Pharmaceutical Sciences (Mack Pub., Co., N.J. 1991) or other standard pharmaceutical science texts, such as the *Handbook of Pharmaceutical Excipients* (Shesky et al. eds., 8th ed. 2017).

The type of compositions includes any type known in the art, including but not limited to liquid compositions formulated for intravenous or other parenteral administration, compositions formulated for topical administration, and compositions formulated for oral administration, such as, for example, tablets, pills, capsules, lozenges, granules.

In certain embodiments, the compositions comprise between 0.4 millimoles and 30 millimoles of a disclosed compound, such as between 1 millimole and 10 millimoles, or such as 1, 2, 5, 10, 20, 25, or 30 millimoles. The compositions further comprise one or more excipients appropriate to the formulation.

Intravenous formulations comprise at least one of: an appropriate solvent, such as water; a salt or ions such as sodium chloride, potassium chloride, potassium ion, sodium ion, chloride ion; a sugar such as glucose and sucrose; a buffer; other excipients, such as DMSO.

Topical formulations include but are not limited to ointments, creams, lotions, salves and comprise at least one of: an appropriate vehicle; a penetration enhancer, such as DMSO and related analogues; and an emulsifier.

Tablets comprise at least one excipient such as, for example: a filler (e.g. starches, lactose, sucrose, glucose); a binder (e.g. carboxymethylcellulose, gelatin, polyvinylpyrrolidone, sucrose); a disintegrating agent (e.g. calcium carbonate, alginic acid, sodium carbonate); a wetting agent (e.g. cetyl alcohol, and glycerol monostearate, sodium lauryl sulfate); a buffering agent; a lubricant (e.g. talc, calcium stearate, magnesium stearate, solid polyethylene glycols, sodium lauryl sulfate); and a coating.

Large macromolecules that are slowly metabolized, such as proteins, polysaccharides, polylactic acids, polyglycolic acids, polymeric amino acids, and copolymers of amino acids can also be used as vehicles for the disclosed agent and composition.

For any disclosed compound, a therapeutically effective dose can be estimated initially from cell culture or animal model assays. Mice, rats, guinea pigs, rabbits, dogs or pigs are commonly used as models in animal testing. An animal model can be used to determine the appropriate range of concentrations and route of administration. Such information can then be used to determine appropriate doses and routes of administration in humans. To estimate human equivalent dose, it is recommended to use the dosage conversion table given in the Guidance for Industry and the Reviewers document (2002, U.S. Food and Drug Administration, Rockville, MD, USA). The exact effective dose to a patient will depend on various considerations, including the severity of illness, the overall health of the patient, age, body weight and sex of the patient, nutrition, time and frequency of administration, route of administration, combination(s) of medicaments, reaction sensitivity and tolerability/response to therapy. The exact dose can be determined by routine experiments and according to the attending physician's professional judgment and discretion. In an embodiment, the total dose of a compound of Formula 1 of the invention is between about 1.25 mg $^{85}$Rb$_e$/kg body weight and about 12.5 mg $^{85}$Rb$_e$/kg body weight. Prophylactic doses of $^{64}$Zn$_e$ (by metal) range from 0.1 to 1.5 mg of pure $^{64}$Zn$_e$ per 1 kg of human body weight. Therapeutic doses of $^{64}$Zn$_e$ (by metal) range from 1 to 15 mg of pure $^{64}$Zn$_e$ per 1 kg of human body weight.

In certain embodiments, prophylactic doses of $^{85}$Rb$_e$ (by metal) range from 0.1 to 1.25 mg of pure $^{85}$Rb$_e$ per 1 kg of human body weight. In certain embodiments, therapeutic doses of 85Rbe (by metal) range from 1.25 to 12.5 mg of pure $^{85}$Rb$_e$ per 1 kg of human body weight.

In some embodiments, the disclosed compositions are administered intravenously, intraperitoneally, orally or intramuscularly. For IV, the dosage form may be in solution. Other conventional routes of administration may also be used, including, but not limited to, other routes of injection and via oral and topical administration.

Exemplary Methods for Making Disclosed Compounds

The disclosed compositions are prepared using methods within the general practice applied in the pharmaceutical industry, such as, for example, methods illustrated in the latest edition of Remington's Pharmaceutical Science Handbook, Mack Pub. N.Y., USA.

Light isotopes may be purchased. Zn-64 oxide and Rb-85Cl with the necessary degree of enrichment may be purchased from, for example, Oak Ridge National laboratory, Oak Ridge, TN, USA.

The compounds of formula 1, for a compound wherein $R_9$ is H, can be prepared as diagrammed below.

Phase 1. Aryl sulfonation

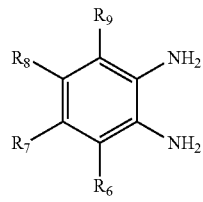

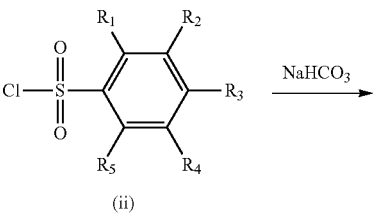

Phase 2. Acylation

Phase 3. Obtaining rubidium complex. To prepare $^{85}$Rb-enriched compounds, $^{85}$Rb$_e$Cl ($^{85}$Rb$_e$ is 99% $^{85}$Rb, for example) is used in the final step shown below.

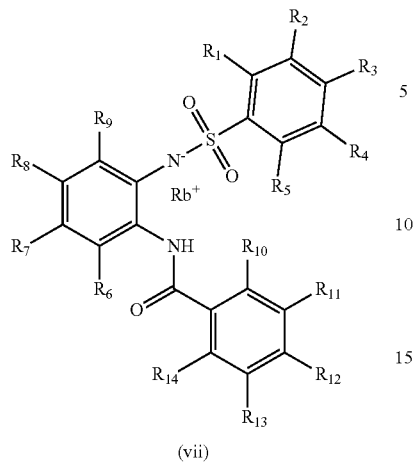

(vii)

A compound of formula 1 can be prepared using intermediate (v) above or a salt thereof as starting material or as an intermediate in the synthesis of the compound of formula 1.

In an embodiment, the R groups of the compound of intermediate (v) and salts thereof are the same as the corresponding R groups of the compound of formula 1. In an embodiment, the synthetic method proceeds as outlined below:

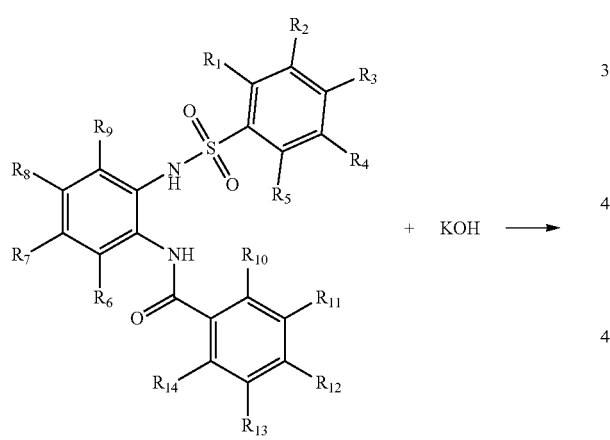

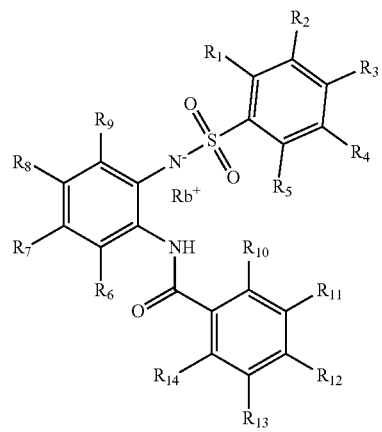

This synthesis produces the potassium salt as an intermediate and the rubidium salt as the product. In an analogous method, $^{85}Rb_eCl$ can be used instead of RbCl to obtain a product in which the rubidium is enriched for $^{85}Rb$.

A synthetic scheme for preparing certain disclosed compounds wherein $R_9$ is H is set forth below.

Phase 1. Aryl Sulfonation of o-phenylenediamine:

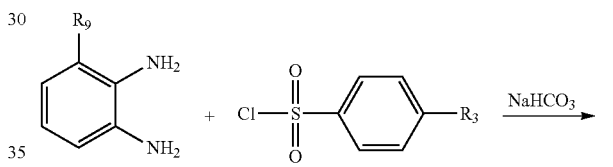

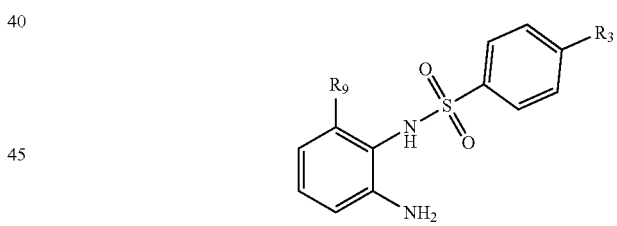

Phase 2. Acylation of N—$R_3$-phenylsulfonyl-o-phenylenediamine:

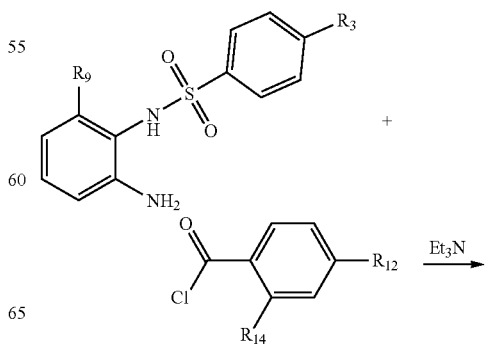

23

-continued

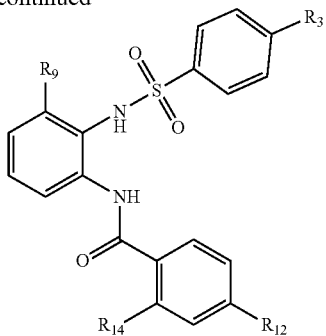

Phase 3. Obtaining of N—(R12, R14-benzoyl)-N'—(R3-phenylsulfonyl)-o-phenylenediamine rubidium complex. To prepare $^{85}$Rb-enriched compounds, $^{85}$Rb$_e$Cl ($^{85}$Rb$_e$ is 99% $^{85}$Rb, for example) is used in the final step shown below.

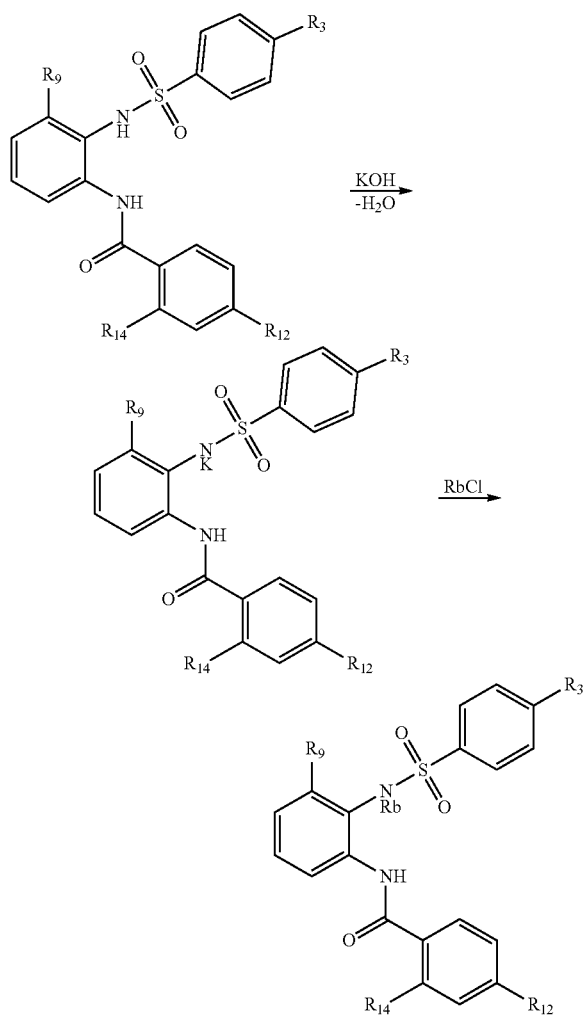

Compounds 1-10 may be prepared by the above synthesis.

EXAMPLES

For this invention to be better understood, the following examples are set forth. These examples are for purposes of illustration only and are not be construed as limiting the scope of the invention in any manner.

Example 1. Effects of Prophylactic Administration of $^{64}$Zn$_e$-Asp and $^{64}$Zn$_e$-Asp+10% E2$^{85}$Rb$_e$ Preparations on the Functional Profile of Phagocytes of Different Localization in Rat Models of Parkinson's Disease Methods: Adult mature rodents were used in the study. Before the beginning of the experiment they were randomized by weight and divided into 7 groups of 8 animals each: group 1—intact animals; group 2—sham-operated animals; group 3—sham-operated animals administered with $^{64}$Zn$_e$-asp; group 4—animal models of Parkinson's disease induced by intracerebral stereotaxic administration of 6-hydroxydopamine (6-OHDA); group 5—animal models of Parkinsonism receiving prophylactic injections of $^{64}$Zn$_e$-asp; group 6—sham-operated animals receiving injections of $^{64}$Zn$_e$-asp+10% E2$^{85}$Rb$_e$; group 7—animal models of Parkinsonism receiving prophylactic injections of $^{64}$Zn$_e$-asp+10% E2$^{85}$Rb$_e$. Before prophylactic administration of the experimental drugs, the animals underwent an open field test to assay their general locomotor activity levels and anxiety. The prophylactic course consisted of 10 daily intraperitoneal injections of the drugs (in the case of combination drug, its components were administered at an interval of 2 hours). After the end of prophylactic course, Parkinson's disease was modelled in the animals. The degree of destruction of neurons in the black substance was studied in dynamics during the apomorphine test 7 and 14 days after the initiation of the disease. Ten days after the last (second) apomorphine test, the animals' behavioral responses were assessed in the open field test followed by euthanasia and analysis of functional (metabolic and phenotypic) profiles of phagocytes of different localization. Thus, the study of the functional profile of phagocytes in rat models of Parkinson's disease was performed on day 28 after the end of the course of prophylactic treatment with the experimental drugs. Resident peritoneal macrophages were isolated from sterile cell suspension of peritoneal exudate; enrichment of the suspension was carried out by 2-hour adhesion. Non-adherent and dead cells were separated by centrifugation. Functional characteristics of circulating phagocytes (monocytes and neutrophils) were evaluated in whole blood taken into a tube containing EDTA used as an anticoagulant. Mononuclear and polymorphonuclear phagocytes were analyzed on a flow cytofluorimeter using a gating method. Phagocytes of microglia were isolated using a Percoll density gradient. To assess the phenotypic profile of phagocytes, expression indices of the pan-phagocytic marker CD14 (co-receptor of the bacterial lipopolysaccharide) and the marker of alternative polarization of phagocytes CD206 (mannose receptor 1) were used. To characterize the metabolic profile, oxidative metabolism and phagocytic activity of microglia as well as the pathway of arginine metabolism were studied using flow cytometry and spectrometric methods respectively. FITC-labeled *Staphylococcus aureus* Wood 46 was used as the object of phagocytosis. The hemogram parameters were analyzed on the hematological analyzer Particle counter model PCE 210 (ERMA, Japan) adapted for the study of blood cells of rats and mice.

Results: At the time of completion of the experiment (14 days after the end of the prophylactic course with the drugs), a reduction in the degree of destruction of neurons in the black substance was recorded in both experimental groups.

The number of animals in the control group with 100% unilateral destruction of neurons in the black substance reached 75%, whereas in the groups where animals received $^{64}Zn_e$-asp and $^{64}Zn_e$-asp containing 10% of $E2^{85}Rb_e$ only 35% (over 50% less than in the control) and 30% (60% less than in the control) of animals, respectively, were observed with complete loss of neurons in the black substance. In addition, 86% destruction of dopaminergic neurons was recorded in 14% of animals in the $^{64}Zn_e$-asp+10% $E2^{85}Rb_e$ group (Table 1).

TABLE 1

Effects of prophylactic administration of $^{64}Zn_e$-asp and $^{64}Zn_e$-asp containing 10% of $E2^{85}Rb_e$ on the destruction of dopaminergic neurons in the black substance in rat models of Parkinson's disease at the time of completion of the experiment

| Index | Control animal models of Parkinsonism n = 8 | $^{64}Zn_e$-asp | $^{64}Zn_e$-asp + 10% $E2^{85}Rb_e$ |
|---|---|---|---|
| Number of animals with 100% destruction of neurons (%) | 75 | 35 | 30 |
| Number of animals with 86% destruction of neurons (%) | — | — | 14 |
| Rate of rotational movements in animals with 100% destruction of neurons (r/30 min) | 484.0 ± 169.8 | 224.3 ± 35.9* | 461.0 ± 45.3 |

*p ≤ 0.05 versus control group of animal models of Parkinsonism

It should also be noted that the rate of rotational movements during the apomorphine test in animals with 100% destruction of neurons of the black substance in the control was 2.2 times higher than in the rat models of experimental Parkinsonism after the prophylactic administration of $^{64}Zn_e$-asp.

The recorded effect of the drugs reducing the degree of damage to dopaminergic neurons in the black substance was accompanied by the following changes in the functional profile of phagocytes of different localization.

Microglia

Figure 1A:
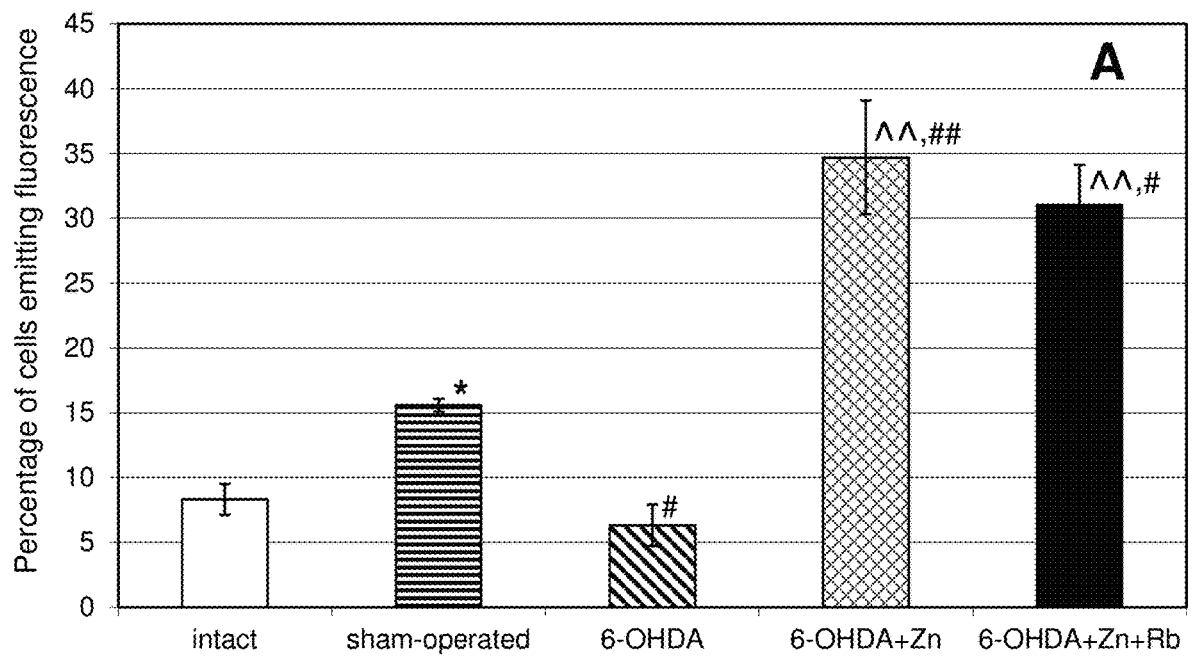
FIG. 1A and FIG. 1B show the effects of $^{64}Zn_e$-asp and $^{64}Zn_e$-asp containing 10% of E2$^{85}Rb_e$ after their prophylactic administration on phagocytic activity of microglia in rat models of experimental Parkinsonism.
Figure 1B:
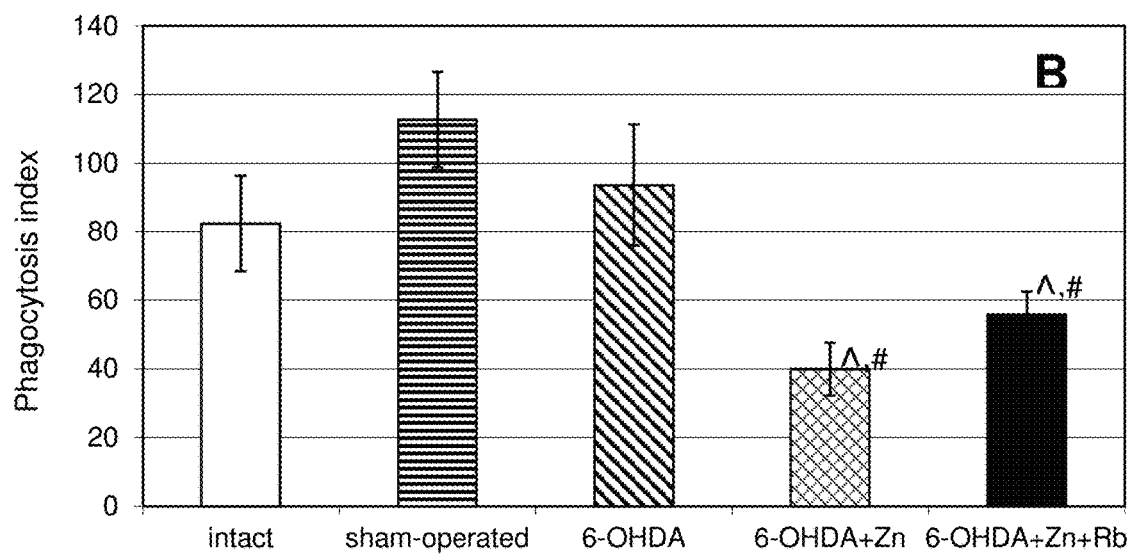

Increase in the phagocytic activity of microglia is an indicator of their activation, both in reparative processes and in the process of development of inflammation. The terminal stages of inflammation are accompanied by complete loss of the ability of microglial cells to phagocytosis associated with the acquisition by microglial cells of the properties of antigen-presenting cells and activation of adaptive pro-inflammatory immune responses. See, e.g., Janda E, Boi L, Carta A R. *Front Mol Neurosci.* 2018; 11:144. doi: 10.3389/fnmol.2018.00144; Fu R, Shen Q, Xu P, Luo J J, Tang Y. *Mol Neurobiol.* 2014; 49(3):1422-34. doi: 10.1007/s12035-013-8620-6. The development of Parkinsonism was accompanied by a decrease in the number of phagocytising cells in microglia and a slight decrease in their phagocytic activity compared to the sham-operated animals, which was probably due to the toxic effect of 6-OHDA. The number of phagocytising cells in microglia in animals that received preventive treatment with the drugs significantly increased while their endocytic activity decreased. Changes in this metabolic process were more pronounced when using the combination drug (FIG. 1A & FIG. 1B).

The modulating effect of $^{64}Zn_e$-asp on the phagocytic activity of microglia cells in intact animals (in vitro) was diametrically opposed to that observed in vivo. It can be assumed that the modulating effect of this drug on the phagocytic activity of microglial cells depends on its basal level, and the nature of the effect is homeostatic (normalizing).

Enhancement of oxidative metabolism of microglia is also characteristic for their activated state which occurs both in reparative and in destructive inflammatory processes. The development of Parkinsonism (as well as surgery without administering 6-OHDA) was accompanied by a decrease in the oxidative metabolism of microglia in the laboratory animals.

In animal models of Parkinson's disease that received a prophylactic course with the drugs, the indicators of oxidative metabolism of microglia were significantly higher than in the control rat models of Parkinson's disease (twice for animals that received the zinc-based drug and 4.5 times for animals that received the combination drug).

At the same time, in the group that received $^{64}Zn_e$-asp, this index was at the level of control intact animals, and in the group that received $^{64}Zn_e$-asp containing 10% of $E2^{85}Rb_e$, the index of reactive oxygen species (ROS) production was 2 times higher than in intact animals (FIG. 1.1.2). Given the nature of clinical prophylactic effect, it can be assumed that the enhancement of oxidative metabolism of microglia after the action of the drugs is due to activation of reparative processes mediated by microglial cells.

Figure 2:
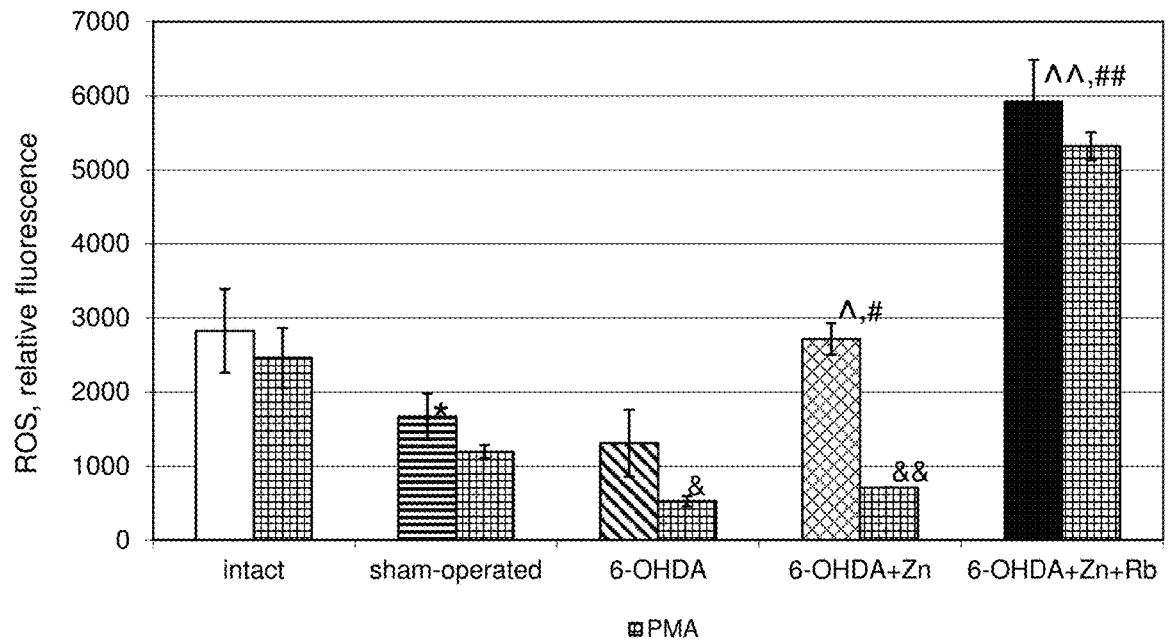
FIG. 2 shows the effects of $^{64}Zn_e$-asp and $^{64}Zn_e$-asp containing 10% of $E2^{85}Rb_e$ after their prophylactic administration on oxidative metabolism of microglia in rat models of experimental Parkinsonism. Key: *—$p \leq 0.05$ versus the group of intact animals; #—$p \leq 0.05$ versus the group of sham-operated animals; ##—$p$ 0.01 versus the group of sham-operated animals; +—$p \leq 0.05$ versus the control group of animal models of Parkinsonism; ++—$p \leq 0.01$ versus the control group of animal models of Parkinsonism; &—$p \leq 0.05$ versus a corresponding index in the unstimulated sample; &&—$p \leq 0.01$ versus a corresponding index in the unstimulated sample.

In addition to the basal level of oxidative metabolism, a metabolic reserve of this function was also analyzed. For this purpose, the cells were treated with phorbol myristate acetate (PMA) in vitro. The metabolic reserve of oxidative metabolism of microglial cells was absent in all animals. FIG. 2.

Increased synthesis of reactive nitrogen species, NO in particular, characterizes the arginine metabolic pathway in phagocytes with the use of NO synthase and is a criterion for pro-inflammatory (M1) activation of microglia accompanying destructive inflammatory processes. A decrease in synthesis of this apoptogenic mediator is indicative of an anti-inflammatory metabolic shift in phagocytes, including those in microglia.

Figure 3:
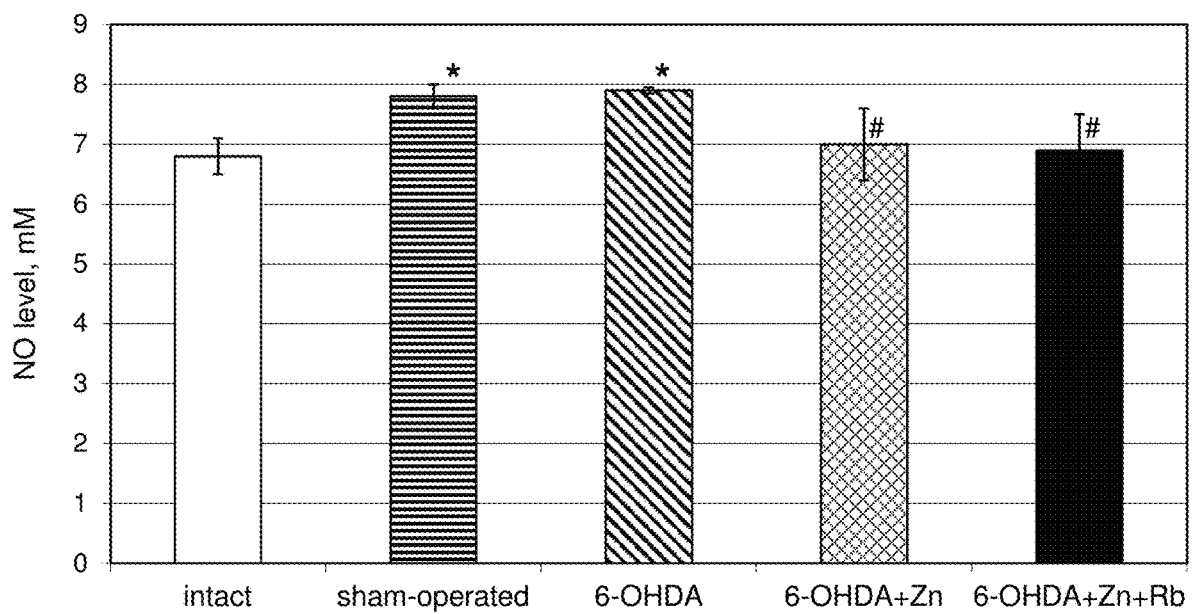
FIG. 3 shows the effects of $^{64}Zn_e$-asp and of $^{64}Zn_e$-asp containing 10% of $E2^{85}Rb_e$ after their prophylactic administration on NO synthesis by microglial cells in rat models of experimental Parkinsonism. Key: *—$p \leq 0.05$ versus the group of intact animals; #—$p \leq 0.05$ versus the group of animal models of Parkinsonism.

The development of Parkinsonism was accompanied by an increase in the production of reactive nitrogen species by phagocytes of microglia, which indicates pro-inflammatory activation of these cells (FIG. 3).

In the groups of animal models of Parkinson's disease that received the drugs, the level of NO synthesis did not differ from that in intact animals. This is evidence of the anti-inflammatory immunomodulatory effect of the drugs on microglial cells. Such assumption is supported by the fact that the NO synthesis is inversely related to the synthesis of ROS. Singh A K, et al., *Nitric Oxide.* 2016; 58:28-41. doi: 10.1016/j.niox.2016.06.002. Taking into account the fact that an increased synthesis of ROS was recorded in the groups of animal models of Parkinsonism that received the drugs, it is logical to assume that this circumstance led to a decrease in the synthesis of apoptogenic reactive nitrogen species by microglial cells and was associated with reduction in the destruction of neurons in the black substance.

It should be noted that in the in vitro study, both drugs had an inhibitory effect on the synthesis of reactive nitrogen species by nonsensitized microglial cells in intact animals, which supports the above assumption.

Arginase activity is the second or alternative pathway for the utilization of arginine by phagocytes. The arginine metabolic pathway is always characterized by changes in both indices (NO synthesis level and arginase activity).

Figure 4:
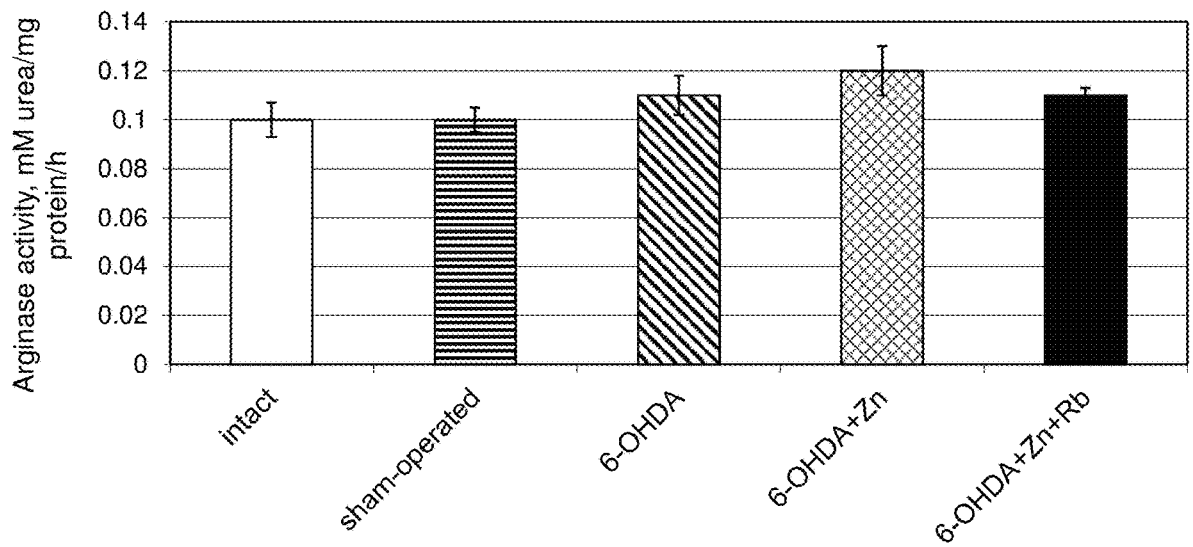
FIG. 4 shows the effects of $^{64}Zn_e$-asp and of $^{64}Zn_e$-asp containing 10% of $E2^{85}Rb_e$ after their prophylactic administration on the arginase activity of microglia in rat models of experimental Parkinsonism. Arginase activity expressed in terms of mM urea/mg protein/hour.

Arginase activity was not statistically significant in the animals of different groups. FIG. 4.

Together with the nature of changes in the level of NO synthesis by microglial cells in animals of different groups, this is another confirmation of the assumption about an anti-inflammatory metabolic shift of microglial phagocytes in rat models of experimental Parkinsonism after prophylactic administration of the drugs.

Neither drug had any statistically significant effects on the arginase activity of nonsensitized microglial cells in intact animals. This indicates that the effect of the drugs on arginine metabolism is mediated and depends on changes in the oxidative metabolism in phagocytes.

Figure 5A:
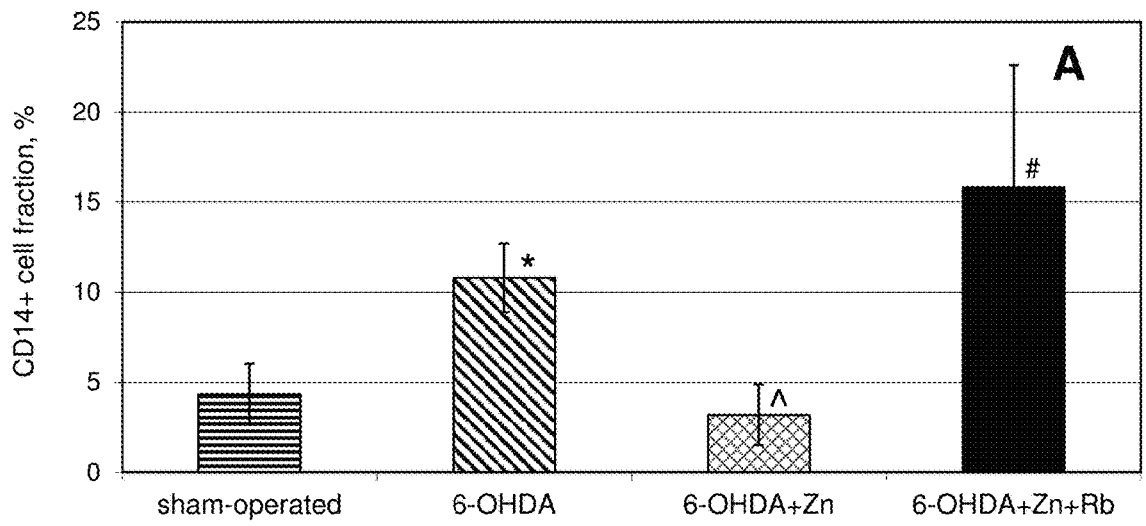
FIG. 5A and FIG. 5B show the expression of CD14 in a population of microglia in rat models of experimental Parkinsonism that received preventive treatment with $^{64}Zn_e$-asp and with $^{64}Zn_e$-asp containing 10% of $E2^{85}Rb_e$, expressed in terms of CD14$^+$ cell fraction (%) (FIG. 5A) and in terms of CD14 expression (GMean) (FIG. 5B). Key: *—$p \leq 0.05$ versus the group of intact animals; #—$p \leq 0.05$ versus the group of sham-operated animals; ##—$p \leq 0.01$ versus the group of sham-operated animals; +—$p \leq 0.05$ versus the control group of animal models of Parkinsonism; ++—$p \leq 0.01$ versus the control group of animal models of Parkinsonism.
Figure 5B:
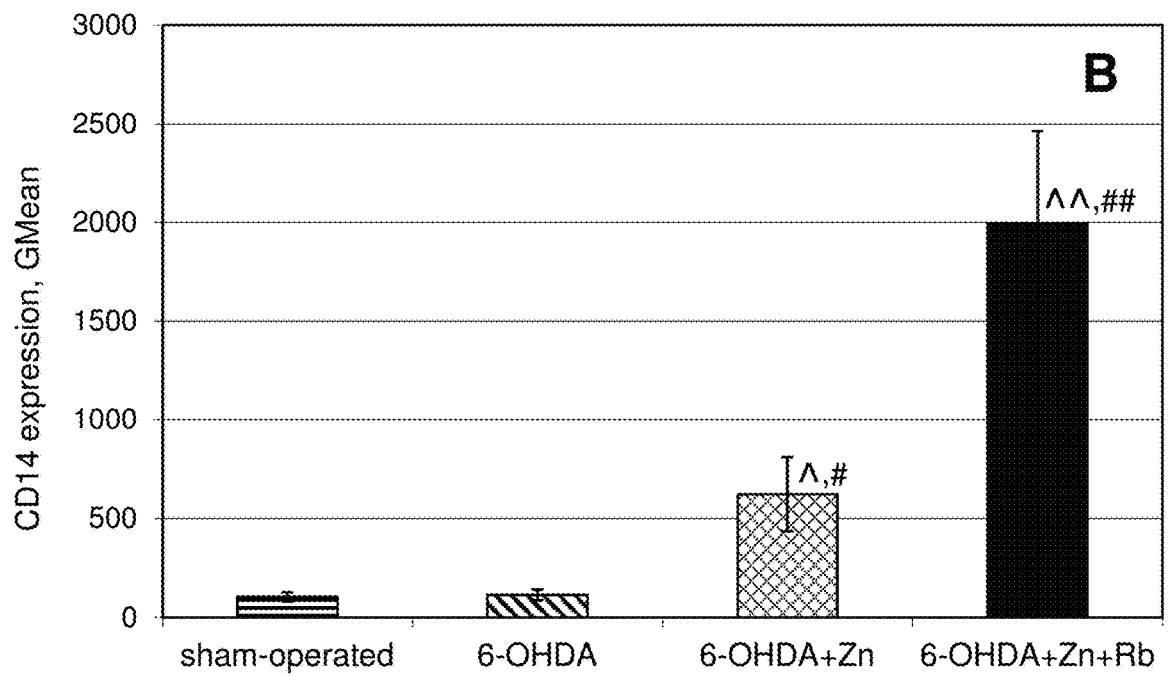
Figure 6A:
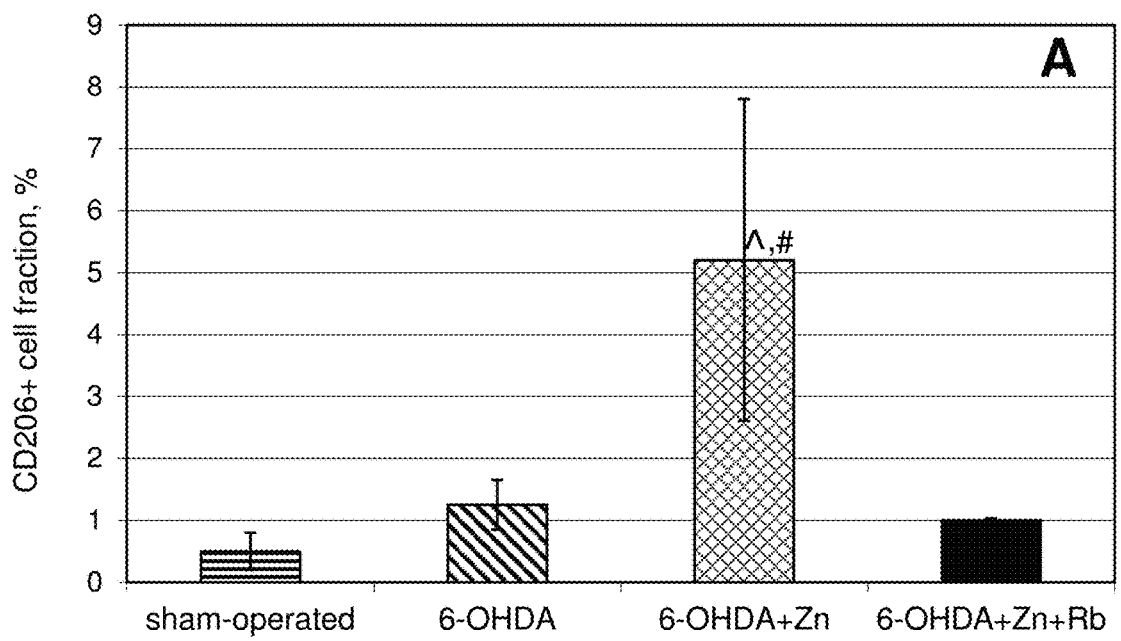
FIG. 6A and FIG. 6B show the expression of CD206 in a population of microglia in rat models of experimental Parkinsonism that received preventive treatment with $^{64}Zn_e$-asp and $^{64}Zn_e$-asp containing 10% of $E2^{85}Rb_e$, expressed in terms of CD206$^+$ cell fraction (%) (FIG. 6A) and in terms of CD206 expression (Gmean) (FIG. 6B). Key: #—$p \leq 0.05$ versus the group of sham-operated animals.
Figure 6B:
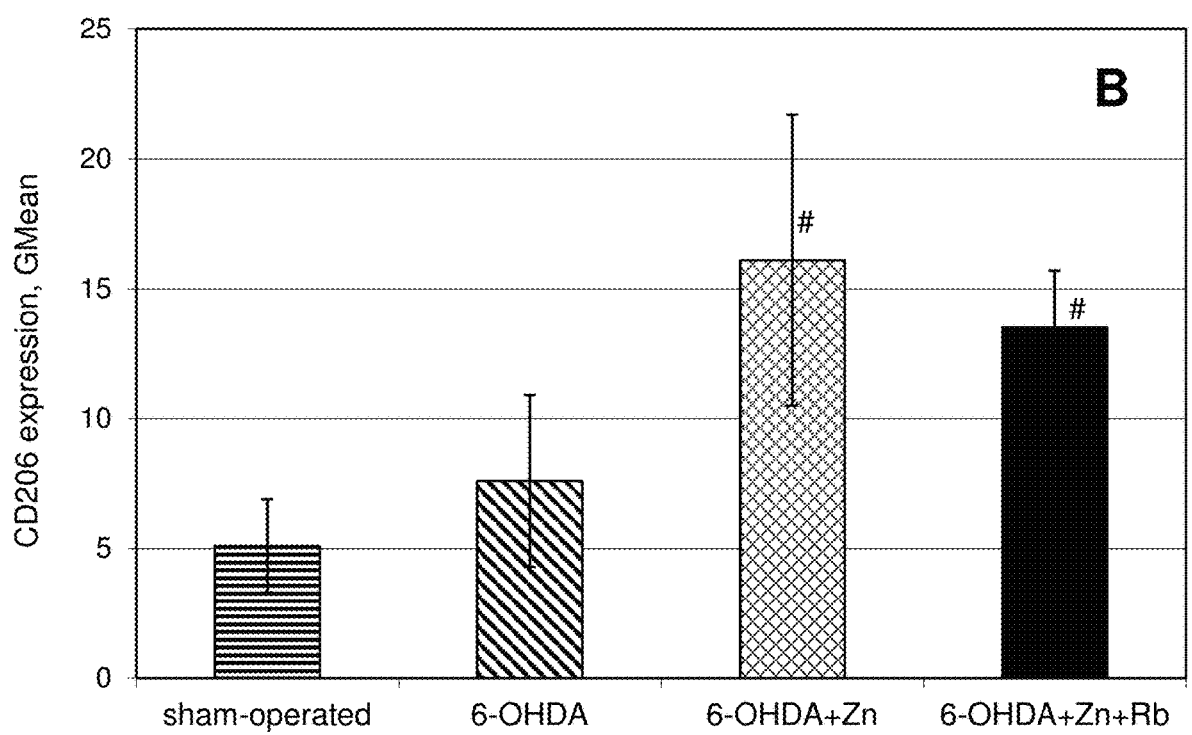

CD14 is a pan-phagocytic marker (expressed by all phagocytes, including microglia). The level of its expression increases with functional maturation of cells associated with their activation (both pro- and anti-inflammatory). The development of Parkinsonism was accompanied by an increase in the number of CD14+ cells in microglia, which may be a consequence of the migration of phagocytes in circulating blood to the brain as a result of the breakdown of the blood-retinal barrier characteristic for the development of neurodegenerative diseases (FIG. 5A and FIG. 5B).

a. Prophylactic administration of $^{64}Zn_e$-asp was accompanied by a decrease in the relative number of CD14+ cells along with an increase in the level of its expression (FIG. 5B), which probably indicates the ability of the drug to reduce manifestations of the blood-retinal barrier disruption and/or migration of phagocytes simultaneously with stimulation of their functional maturation which can be both pro- and anti-inflammatory. Based on our own experience, we believe that an increase in the number of CD206+ cells in microglia is evidence of activation of their population as a whole. Such increase in the level of expression is evidence of an alternative (anti-inflammatory) metabolic polarization of the brain phagocytes. According to the results of our study, the development of Parkinsonism was accompanied by an increase in the fraction of CD206+ cells (FIG. 6A) without a significant increase in the average level of its expression (FIG. 6B), which is evidence of activation of pro-inflammatory microglia, taking into account pathogenesis of the disease. Prophylactic administration of $^{64}Zn_e$-asp caused a significant increase in the relative number of CD206+ cells in microglia along with an increase in the level of its expression, which is indicative of an anti-inflammatory shift in the functional profile of these cells. It should be noted that there was a significant individual variability of both indices in the animals of this group.

b. The effect of $^{64}Zn_e$-asp+10% $E2^{85}Rb_e$ on the phenotypic profile of microglia in animal models of Parkinsonism had a slightly different character. At the time of completion of the experiment, the relative number of CD14+ cells in microglia in the animals that had undergone the prophylactic course did not differ significantly from that in the control group of animal models of Parkinson's disease (FIG. 5B). However, the level of expression of this marker increased significantly (FIG. 6B). Both facts indicate that the drug, most likely, has no effect on the migration of peripheral phagocytes to the brain, but stimulates the functional maturation of resident microglial cells. The relative number of CD206+ cells in microglia after administration of this drug was not significantly different from that in the control animal models of Parkinsonism (FIG. 6A). At the same time, the level of its expression significantly increased (FIG. 6B), which convincingly demonstrates the ability of the drug to cause anti-inflammatory activation of brain phagocytes.

Circulating Phagocytes

Parkinson's disease is a multisystem neurodegenerative disorder which is based on the irreversible destruction of dopaminergic neurons occurring against the background of a pro-inflammatory shift in metabolism in the resident brain phagocytes called microglia. However, a growing number of recent experimental studies and clinical observations indicate that the inflammatory process in Parkinson's disease has a systemic nature and is accompanied by a pro-inflammatory functional shift of phagocytes localized at the periphery of the brain, including circulating mono- and polymorphonuclear phagocytes. Smith A M, et al., *Mov Disord.* 2018; 33(10):1580-1590. doi: 10.1002/mds.104. The development of Parkinsonism is associated with monocytosis and increased generation of precursors of monocytes in the bone marrow. Raj T, Rothamel K et al. Science. 2014; 344(6183):519-23. doi: 10.1126/science.1249547. Monocytosis in Parkinson's disease is associated with a decrease in the number of circulating granulocytes (neutrophils in the first place). Wijeyekoon R S, et al. *Front Neurol.* 2018 Oct. 16; 9:870. doi: 10.3389/fneur.2018.00870. Circulating monocytes in Parkinson's disease are characterized by an activated state, as evidenced by an increase in the expression of apoptosis markers (apoptosis induced by activation) Wijeyekoon R S, et al., *Front Neurol.* 2018 Oct. 16; 9:870. doi: 10.3389/fneur.2018.00870; Lin W C, et al., *Biomed Res Int.* 2014; 2014:635923. doi: 10.1155/2014/635923). There are also data about a decrease in the phagocytic activity of peripheral blood monocytes in patients with Parkinsonism. Grozdanov V, et al., *Acta Neuropathol.* 2014; 128(5):651-63. doi: 10.1007/s00401-014-1345-4. The disruption of monocyte functions is associated with a genetically determined defect in the expression of LRRK2 kinase (leucine-rich repeat kinase 2). Bliederhaeuser C, et al., *Acta Neuropathol Commun.* 2016; 4(1):123.

Figure 7A:
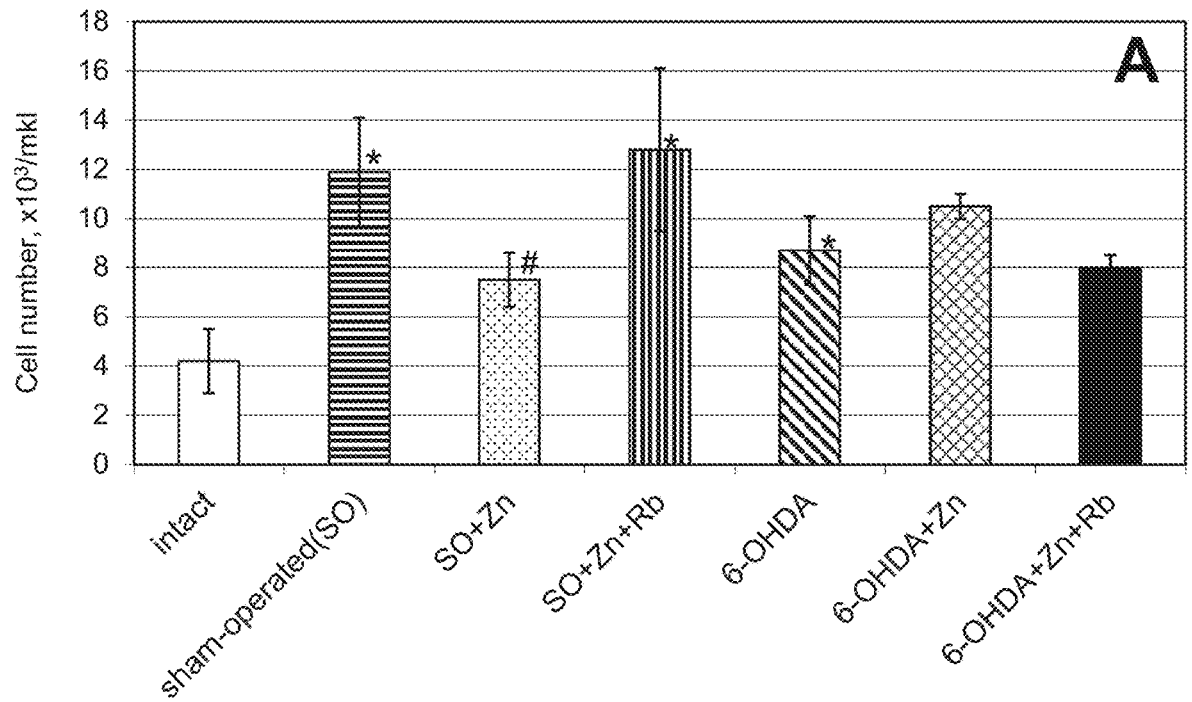
FIG. 7A and FIG. 7B show hemogram values of rat models of Parkinson's disease that received preventive treatment with $^{64}Zn_e$-asp and $^{64}Zn_e$-asp containing 10% of $E2^{85}Rb_e$. Results expressed as cell number×$10^3$/µl (or mkl) (FIG. 7A) and as cell fraction (%) (FIG. 7B). Key: *—$p \leq 0.05$ versus the values of intact animals; #—$p \leq 0.05$ versus the values of animal models of Parkinsonism.
Figure 7B:
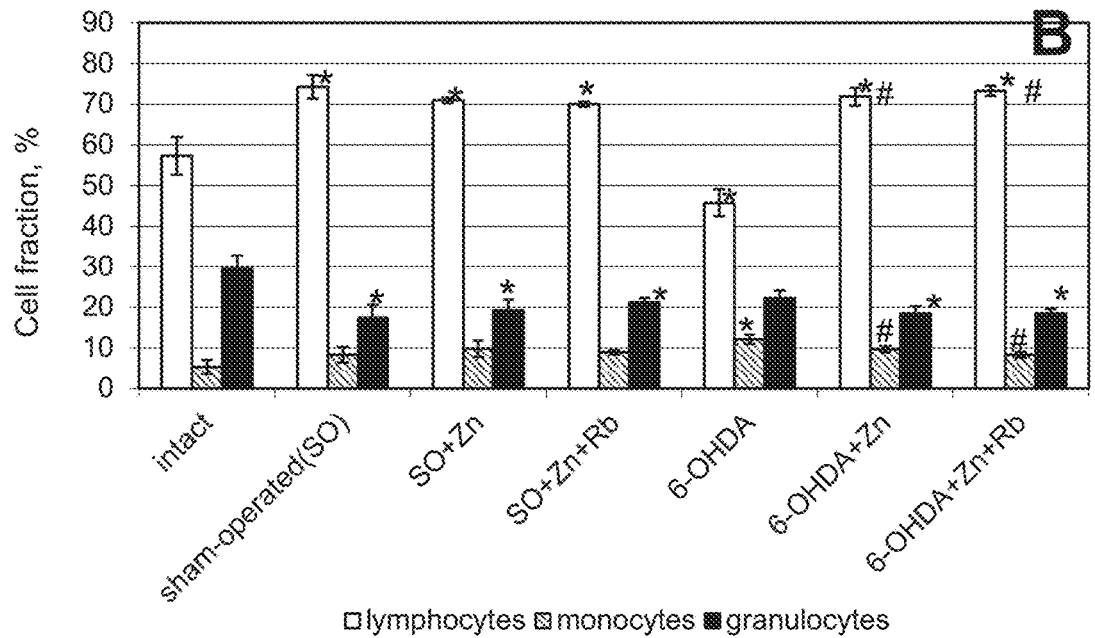

The development of Parkinsonism was accompanied by statistically significant leukocytosis (FIG. 7A and FIG. 7B). Analysis of the percentage of major leukocyte populations (lymphocytes, monocytes, granulocytes (neutrophils)) has shown that it is most likely that the cause of leukocytosis in Parkinsonism is monocytosis, since the fraction of these phagocytes is statistically significantly increased in rat models of Parkinson's disease (FIG. 7B). Leukocytosis was also observed in the sham-operated animals. However, in this case it was considered to be caused by an increase in the fraction of lymphocytes, as a natural sign of resolution of the inflammatory process, given that the study was conducted long after the sham operation. In the animal models of Parkinson's disease that received the drugs comprising microelements, the absolute circulating leukocyte count did not differ significantly from the same value in the control group of rat models of Parkinson's disease. However, no significant changes were recorded in the population composition of peripheral blood leucocytes after administering the drugs: there was a decrease in monocytosis and normalization of the relative circulating lymphocyte count, which is an indication of their anti-inflammatory systemic effect.

Figure 8A:
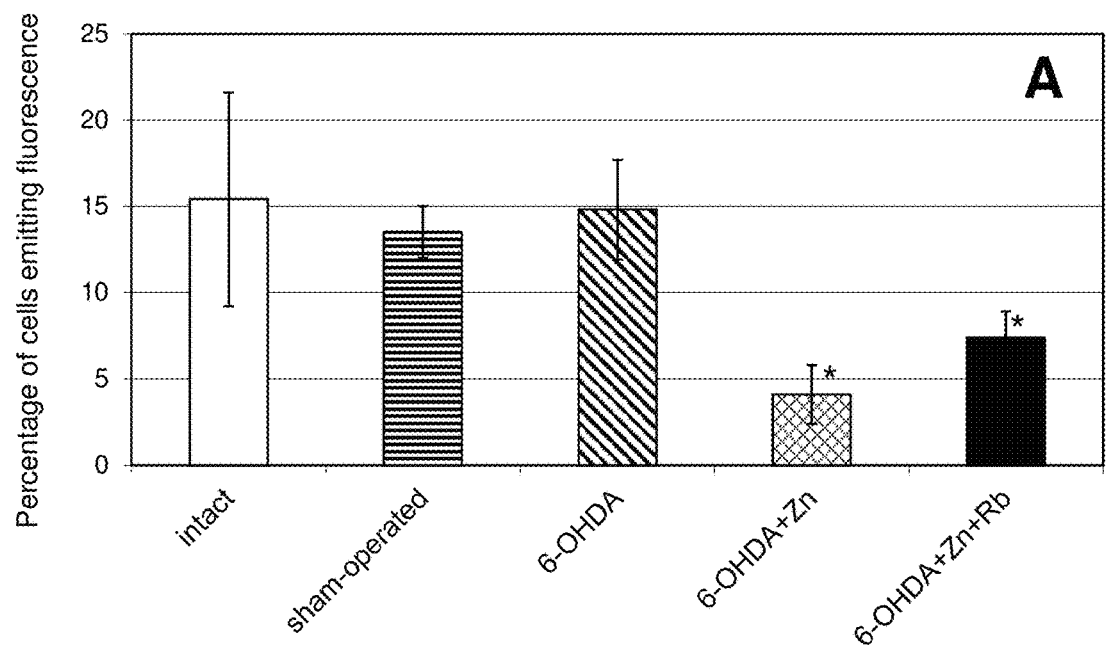
FIG. 8A and FIG. 8B show the effects of $^{64}Zn_e$-asp and $^{64}Zn_e$-asp containing 10% of $E2^{85}Rb_e$ after their prophylactic administration on the phagocytic activity of monocytes in rat models with experimental Parkinsonism.
Figure 8B:
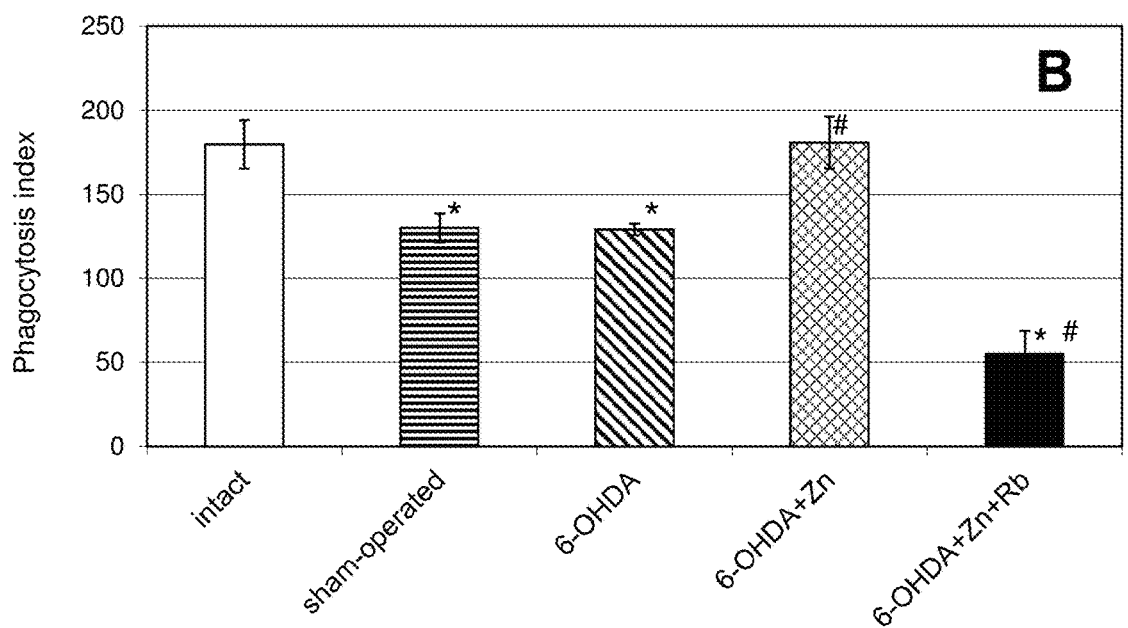

The phagocytic activity of circulating monocytes in the rat models of Parkinsonism at the end of the experiment was reduced in comparison with the intact animals (FIG. 8), which correlates with the results of the above clinical observations.

In the animals that received zinc as a drug, the phagocytic activity of monocytes did not differ from that of intact animals. In the rats receiving the combination drug, the phagocytic activity of monocytes was significantly reduced. The number of phagocytising cells in the animals that received preventive treatment with microelements was also reduced (FIG. 8B), which correlates with the data on the reduction in monocyte count after a prophylactic course with the drugs (FIG. 7A and FIG. 7B).

Figure 9:
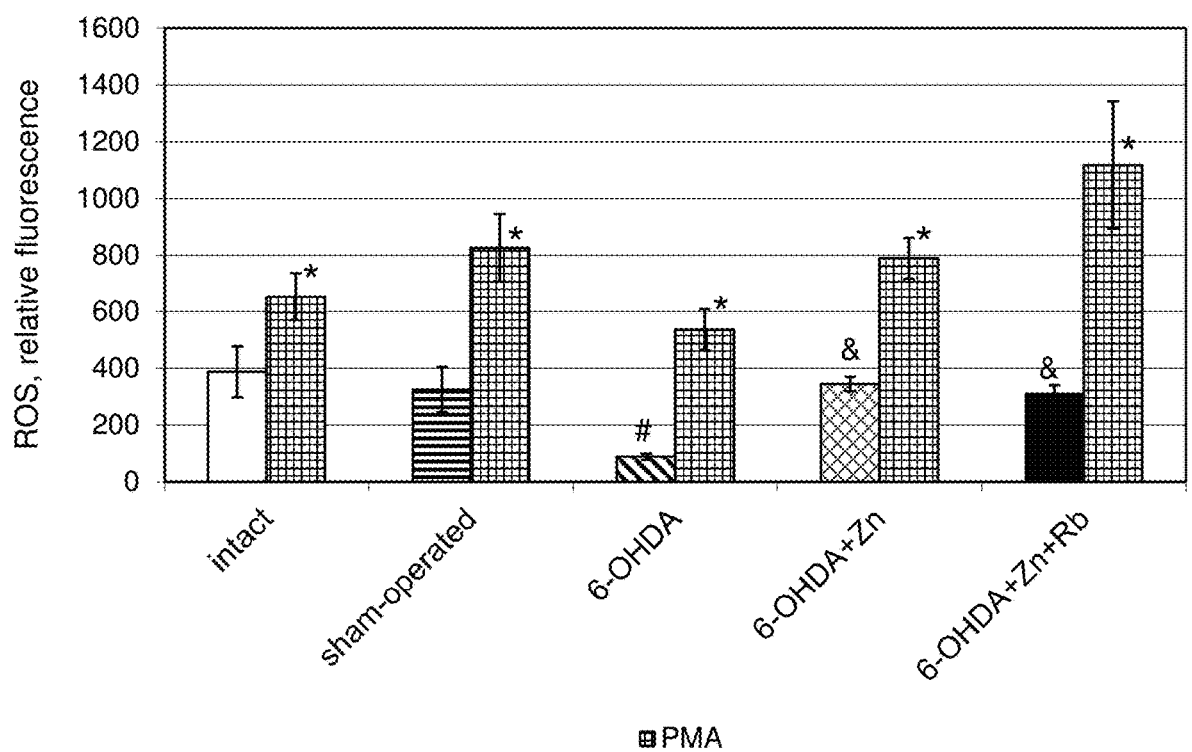
FIG. 9 shows the effects of $^{64}Zn_e$-asp and $^{64}Zn_e$-asp containing 10% of $E2^{85}Rb_e$ after their prophylactic administration on oxidative metabolism in circulating monocytes in rat models of experimental Parkinsonism. Key: *—$p \leq 0.05$ versus a corresponding index in the unstimulated sample; #—$p \leq 0.05$ versus the group of intact animals; &—$p \leq 0.05$ versus the control group of animal models of Parkinsonism.

Oxidative metabolism in monocytes in the animal models of Parkinson's disease was statistically significantly lower in comparison with that of intact animals (FIG. 9). In rats that received preventive courses with the trace elements, oxidative metabolism in circulating monocytes was within the normal range.

A functional reserve of oxidative metabolism was present in the cells of animals of all groups. It should be noted that in the in vitro study, the drug comprising microelements slightly inhibited intracellular oxidative metabolism in nonsynthesized monocytes of peripheral blood of the intact rats. In this case, as can be seen from FIG. 9, in the conditions of weakened oxidative metabolism in the in vivo study, the drugs produced a normalizing effect. It is likely that the nature of the effect of zinc and rubidium drugs on the intracellular production of reactive oxygen species by immature forms of mononuclear phagocytes depends on the initial value of this index in the cells.

Figure 10A:
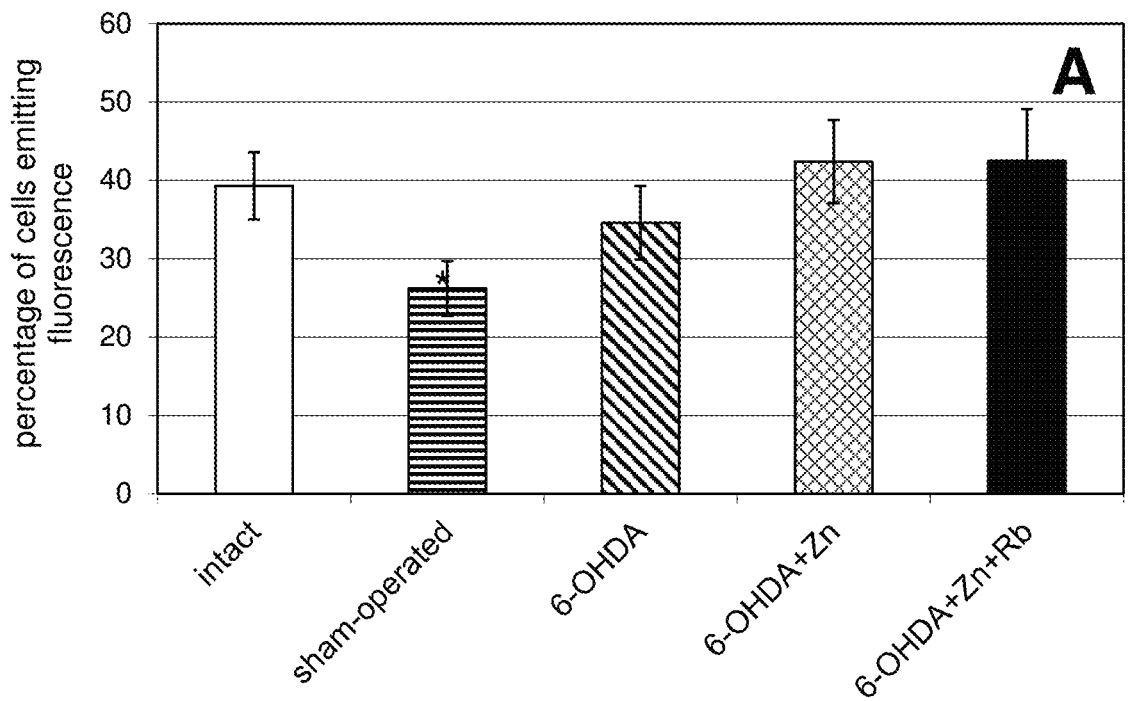
FIG. 10A and FIG. 10B show the effects of $^{64}Zn_e$-asp and $^{64}Zn_e$-asp containing 10% of $E2^{85}Rb_e$ after their prophylactic administration on the phagocytic activity of neutrophils in rat models of experimental Parkinsonism.
Figure 10B:
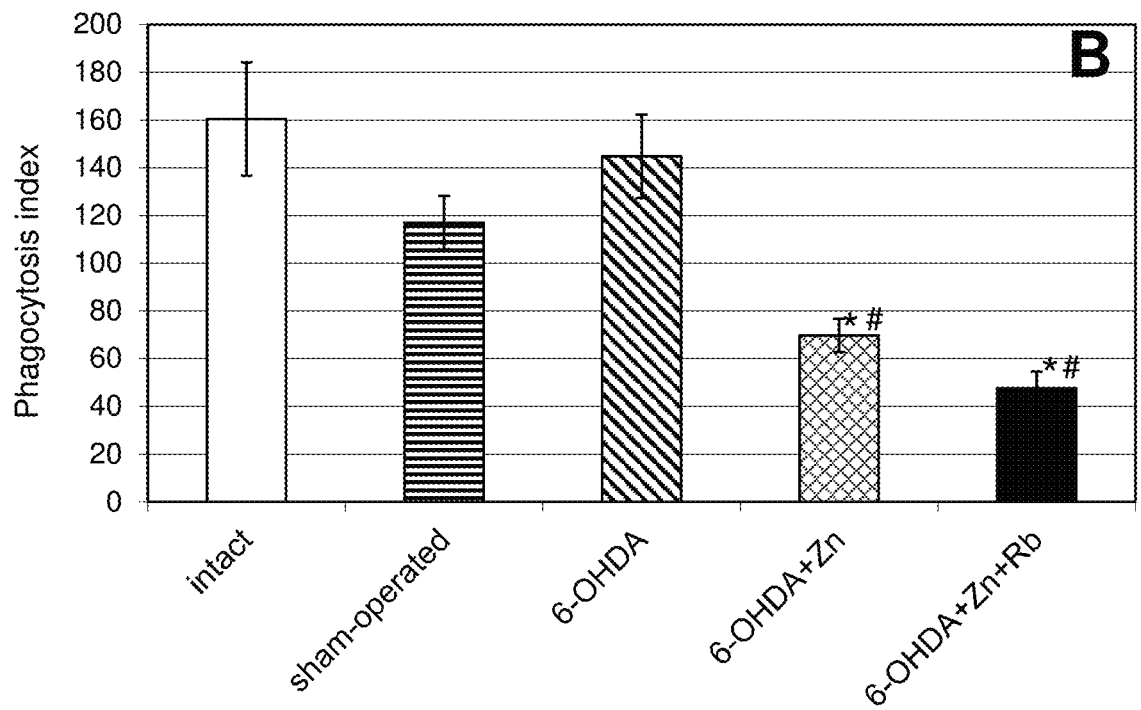

A modulating effect of the drugs comprising microelements regarding the functions of granulocytes (neutrophils) in the peripheral blood of rat models of Parkinsonism was also recorded. The relative number of circulating neutrophils in all animals of the experimental groups was lower than that of intact animals (FIG. 7B). At the same time, the phagocytic function of these cells in rat models of Parkinson's disease was the same as in the intact animals (FIG. 1.1.10). In the groups of animal models of Parkinsonism that received prophylactic courses with microelements, the phagocytic activity of peripheral blood neutrophils was significantly decreased in comparison with the control animal models of Parkinson's disease, as well as versus the intact animals. The obtained results coincide with the character of in vitro modulating effect of the drugs comprising microelements on the phagocytic function of nonsensitized neutrophils in peripheral blood of the intact rats. FIG. 10A and FIG. 10B.

Figure 11:
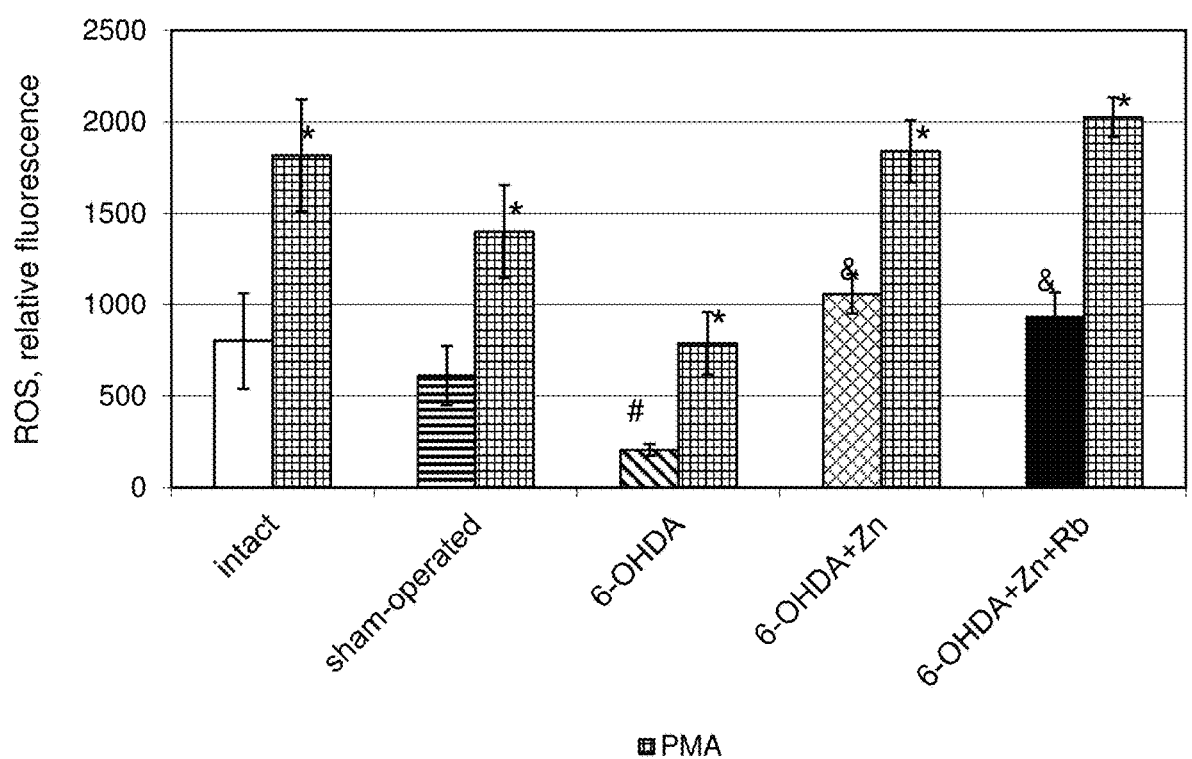
FIG. 11 shows the effects of $^{64}Zn_e$-asp and $^{64}Zn_e$-asp containing 10% of $E2^{85}Rb_e$ after their prophylactic administration on oxidative metabolism in circulating neutrophils in rat models of experimental Parkinsonism (results expressed as ROS, relative fluorescence). Key: *—$p \leq 0.05$ versus a corresponding index in the unstimulated sample; #—$p \leq 0.05$ versus the group of intact animals; &—$p \leq 0.05$ versus the control group of animal models of Parkinsonism.

In the development of Parkinson's disease, intracellular oxidative metabolism in peripheral blood neutrophils was reduced in comparison with the intact animals (FIG. 11).

Prophylactic administration of $^{64}Zn_e$-asp and $^{64}Zn_e$-asp containing 10% of $E2^{85}Rb_e$ was accompanied by the absence of any disturbances of oxidative metabolism in rat models of experimental Parkinsonism. A functional reserve of neutrophil oxidative metabolism was present in the animals of all groups.

Figure 12A:
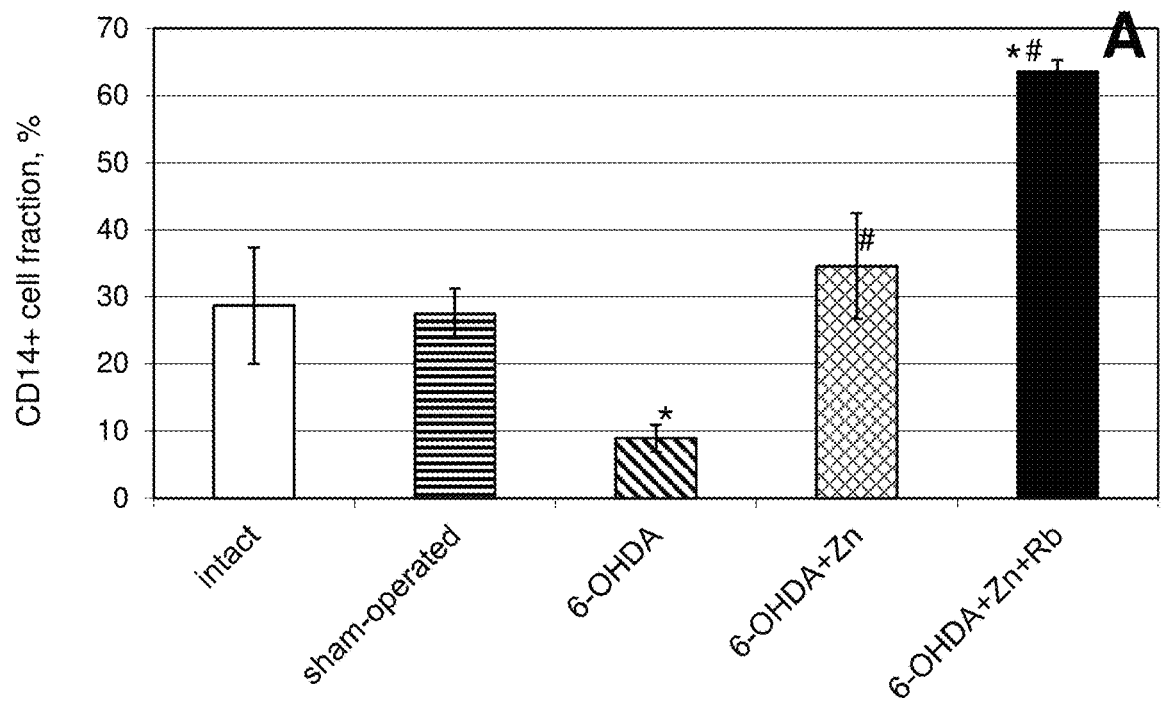
FIG. 12A and FIG. 12B show CD14 expression in a population of peripheral blood phagocytes in rat models of experimental Parkinsonism that received preventive treatment with $^{64}Zn_e$-asp and $^{64}Zn_e$-asp containing 10% of $E2^{85}Rb_e$. Key: *—$p \leq 0.05$ versus the group of intact animals; #—$p \leq 0.05$ versus the control group of animal models of Parkinsonism.
Figure 12B:
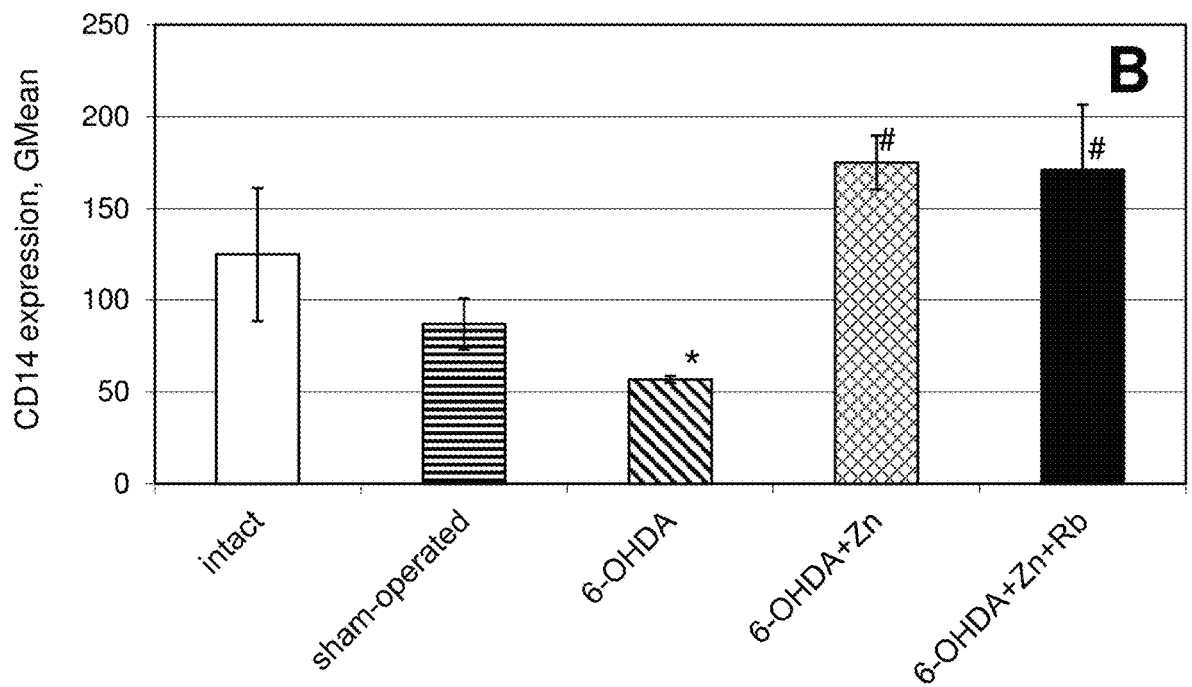

Data on the assessment of the phenotypic profile of peripheral blood phagocytes in the animals confirm the results of assessment of their metabolic characteristics. A fraction of CD14+ peripheral blood phagocytes in the control animal models of Parkinsonism was statistically significantly lower in comparison with that of intact animals, which indicates the circulation of immature cell forms, probably associated with monocytosis (FIG. 12A and FIG. 12B). The expression level of this marker in rat modes of Parkinson's disease was also lower than in intact animals, which is confirmed by the presence of immature forms of circulating phagocytes. FIG. 12A and FIG. 12B.

Figure 13A:
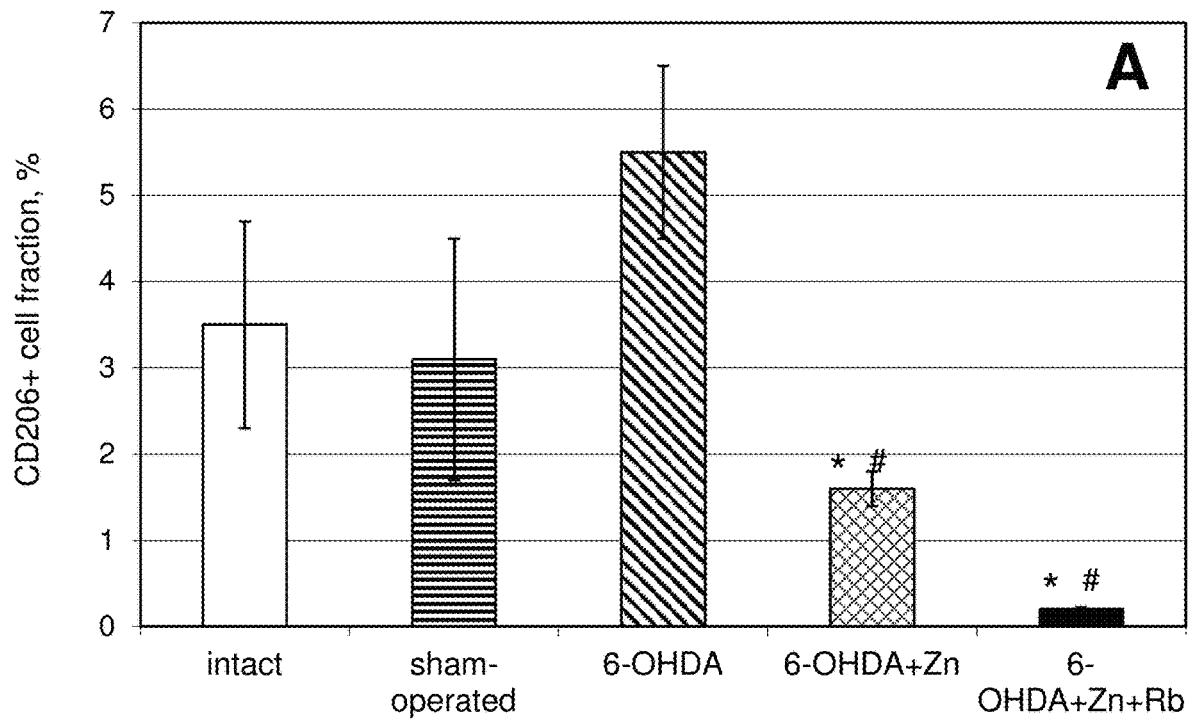
FIG. 13A and FIG. 13B show CD206 expression in a population of peripheral blood phagocytes in rat models of experimental Parkinsonism that received preventive treatment with $^{64}Zn_e$-asp and $^{64}Zn_e$-asp containing 10% of $E2^{85}Rb_e$ (13A, CD206$^+$ cell fraction, %; 13B, CD206 expression, Gmean). Key: *—$p \leq 0.05$ versus the group of intact animals; #—$p \leq 0.05$ versus the control group of animal models of Parkinsonism.
Figure 13B:
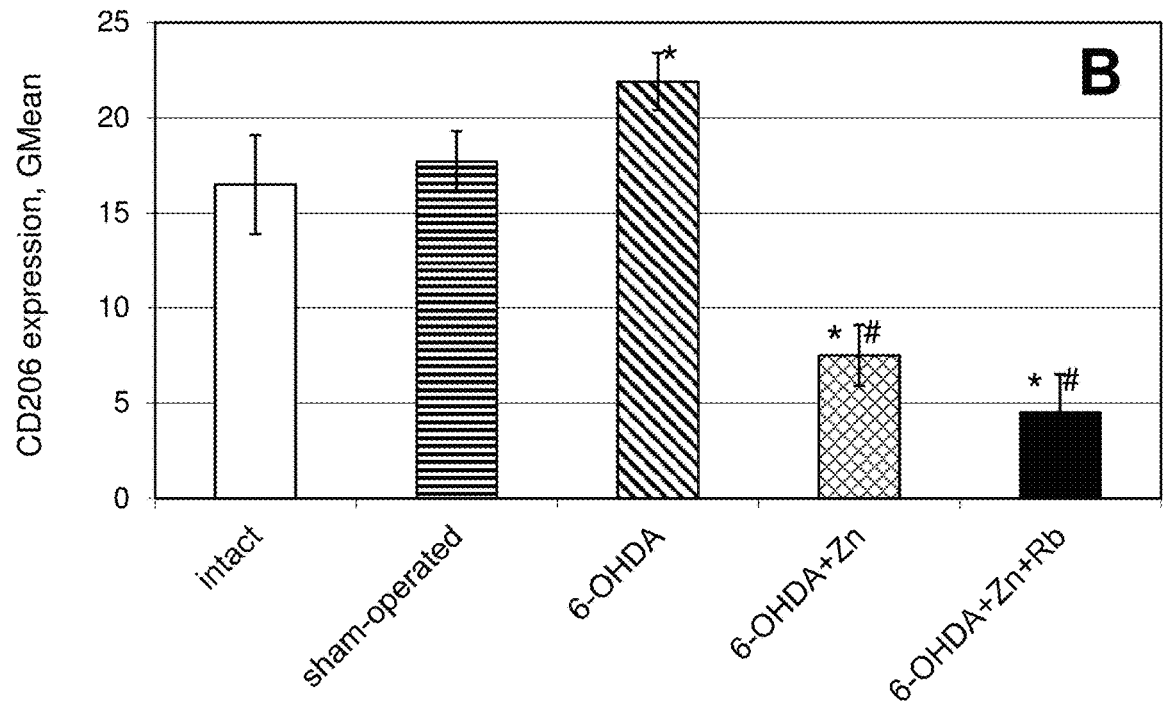

The relative number of circulating phagocytes expressing CD206, as well as the level of expression of this phenotypic marker in rat models of Parkinsonism, was higher than in intact animals, which should be considered as a sign of activation of immature phagocytes recruited from the bone marrow FIG. 13A and FIG. 13B.

At the end of the experiment, CD206 expression in the circulating phagocyte population in the animals that received prophylactic courses with the drugs comprising microelements was significantly lower than in the control group of animal models of Parkinson's disease and the group of intact animals. This is additional evidence of an anti-inflammatory effect of the drugs on phagocytes carried along by the circulating blood. In general, the analysis of metabolic and phenotypic characteristics of circulating phagocytes demonstrates the ability of the drugs to reduce manifestations of a systemic inflammatory response associated with monocytosis, which is a characteristic sign of Parkinsonism.

Peritoneal Macrophages

Analysis of the functional and phenotypic profile of peritoneal macrophages in the animal models of Parkinson's disease that received prophylactic courses with $^{64}Zn_e$-asp and $^{64}Zn_e$-asp containing 10% of $E2^{85}Rb_e$, was due to three circumstances. First, the drugs were administered intraperitoneally and peritoneal macrophages were the first cells of the immune system to be exposed to the action of preparations comprising microelements. Secondly, it is known that the blood-brain barrier is not an absolute barrier to interrelation between the brain and the peripheral immune system, and that the brain antigens are transported through lymphatic vessels of the central nervous system into regional lymph nodes, nasal and deep cervical, which are part of mucosa-associated lymphoid tissue (MALT) (Louveau A, et al., *Trends Immunol.* 2015 October; 36(10):569-577. doi: 10.1016/j.it.2015.08.006; Raper D, et al., *Trends Neurosci.* 2016 September; 39(9):581-586. doi: 10.1016/j.tins.2016.07.001). MALT also includes peritoneal cavity. According to the scheme of activation of the immune response in MALT, the presence of an antigenic stimulus in any of its compartments may be accompanied by the activation of MALT as a whole. And thirdly, a proven fact is the interrelation between neurodegenerative diseases and disorders of the normal intestinal microbiota—dysbiosis, the development of which is accompanied by activation of phagocytes in the peritoneal cavity adjacent to the intestine. Kishimoto Y, et al., *Neuromolecular Med.* 2019 May 11. doi: 10.1007/s12017-019-08539-5.

Figure 14A:
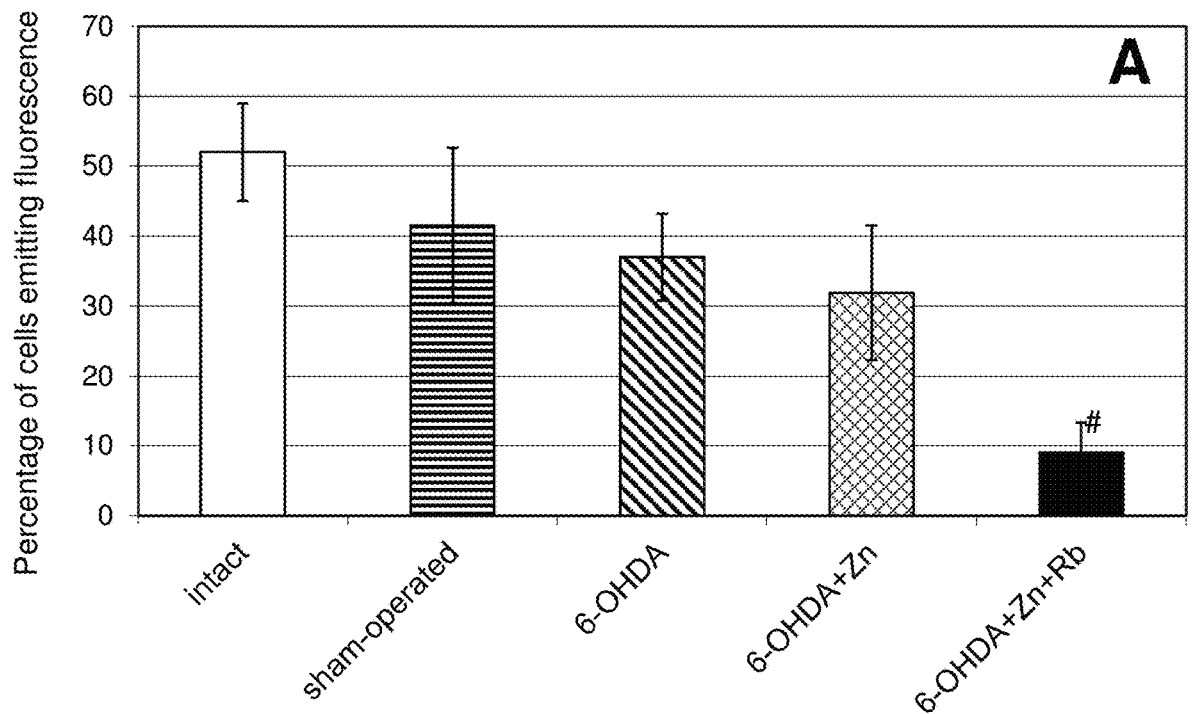
FIG. 14A and FIG. 14B show the effects of $^{64}Zn_e$-asp and $^{64}Zn_e$-asp containing 10% of $E2^{85}Rb_e$ after their prophylactic administration on the phagocytic activity of peritoneal macrophages in rat models of experimental Parkinsonism.
Figure 14B:
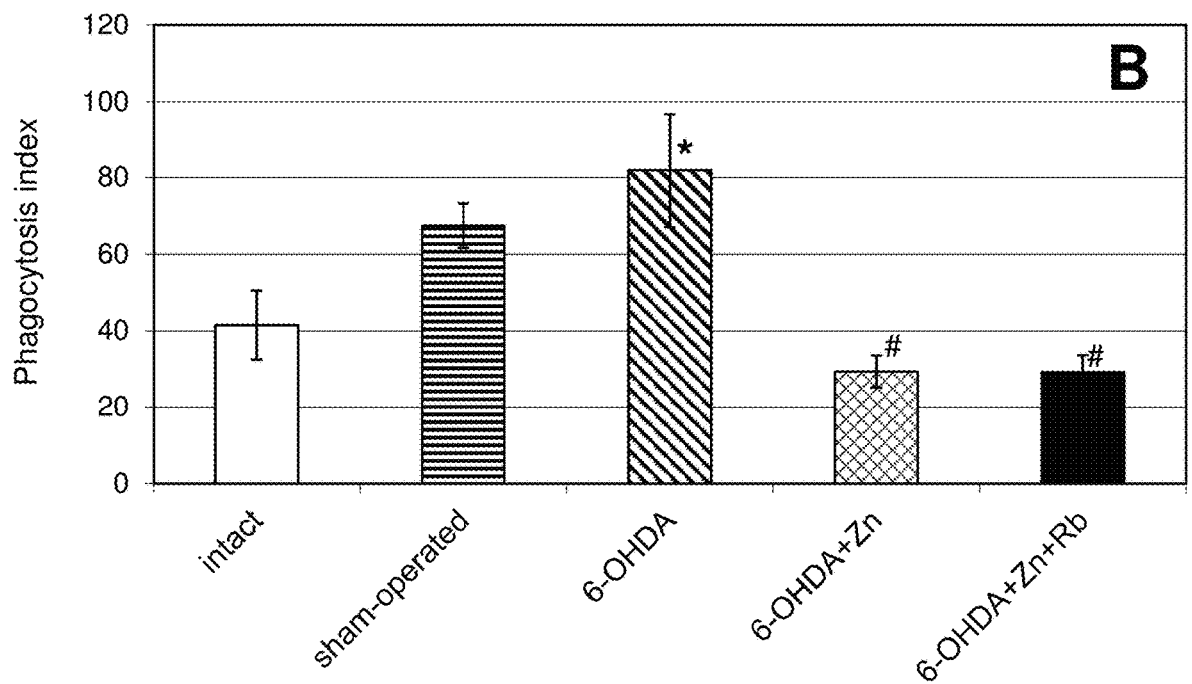

The development of Parkinson's disease was accompanied by activation of peritoneal macrophages in rats. Thus, peritoneal phagocytes in the animal models of Parkinsonism were characterized by a statistically significantly increased endocytic activity in comparison with intact animals. FIG. 14A and FIG. 14B.

Prophylactic administration of $^{64}Zn_e$-asp and $^{64}Zn_e$-asp containing 10% of $E2^{85}Rb_e$ prevented an increase in phagocytosis by peritoneal macrophages in Parkinsonism.

Figure 15:
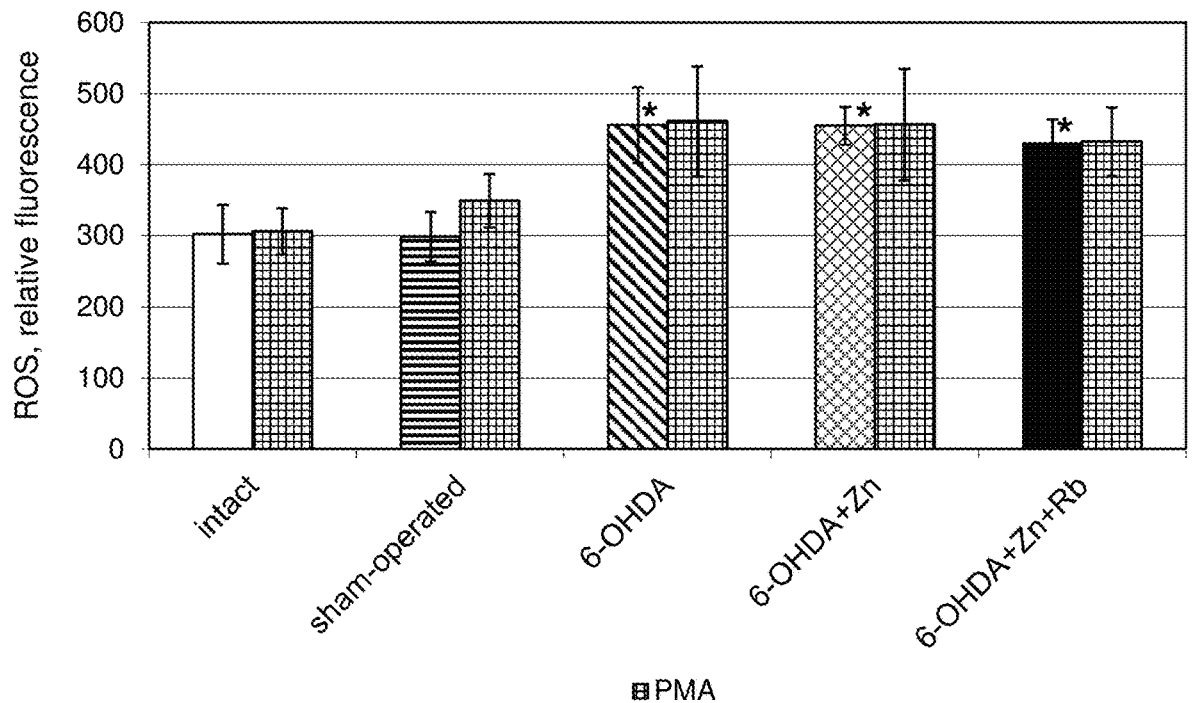
FIG. 15 shows the effects of $^{64}Zn_e$-asp and $^{64}Zn_e$-asp containing 10% of $E2^{85}Rb_e$ after their prophylactic administration on the oxidative metabolism of peritoneal macrophages in rat models of experimental Parkinsonism. Key: *—$p \leq 0.05$ versus a corresponding index in the unstimulated sample.

Oxidative metabolism of peritoneal macrophages in rat models of Parkinson's disease was also higher than that in intact animals. FIG. 15.

Preventive administration of the drugs comprising microelements did not influence this index in the animal models of Parkinsonism.

Figure 16:
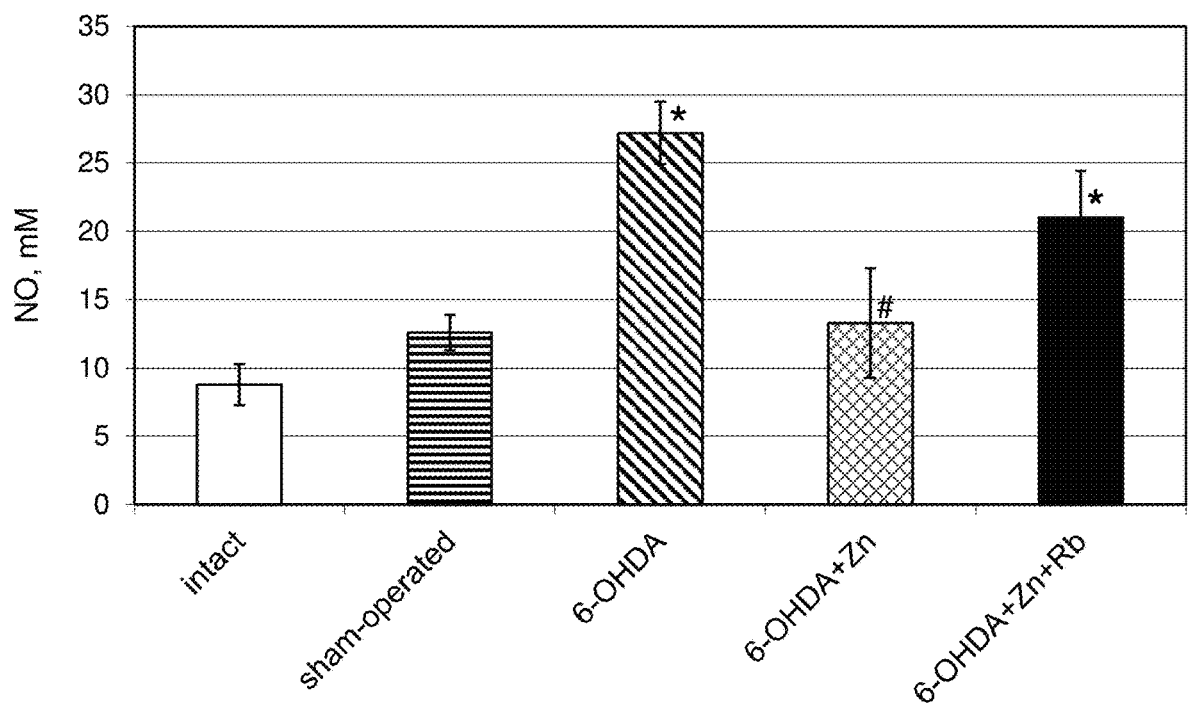
FIG. 16 shows the effects of $^{64}Zn_e$-asp and $^{64}Zn_e$-asp containing 10% of $E2^{85}Rb_e$ after their prophylactic administration on NO synthesis by microglial cells in rat models of experimental Parkinsonism. *—$p \leq 0.05$ versus the group of intact animals; #—$p \leq 0.05$ versus the group of animal models of Parkinsonism.

Greatly enhanced production of reactive nitrogen species is also indicative of the pro-inflammatory activation of peritoneal macrophages in Parkinsonism. FIG. 16.

Prophylactic administration of $^{64}Zn_e$-asp and $^{64}Zn_e$-asp containing 10% of $E2^{85}Rb_e$ prevented an increase in NO synthesis by peritoneal macrophages in the animal models of Parkinsonism.

Figure 17:
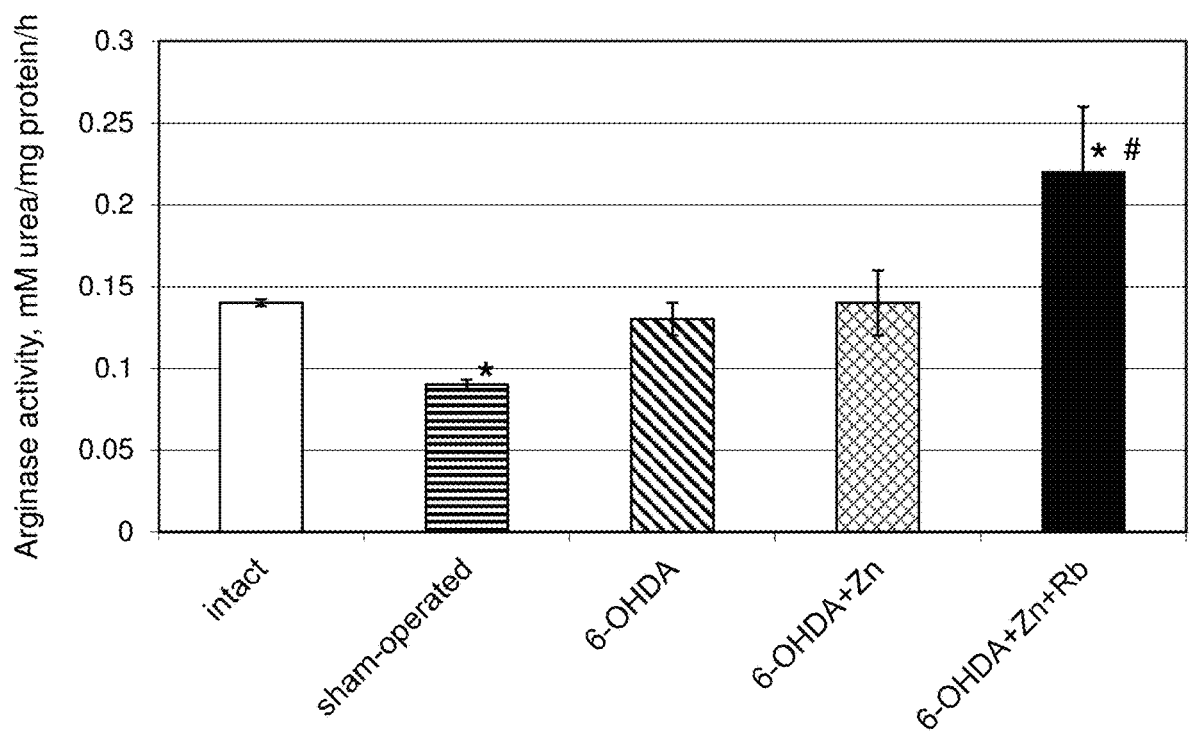
FIG. 17 shows the effects of $^{64}Zn_e$-asp and $^{64}Zn_e$-asp containing 10% of $E2^{85}Rb_e$ after their prophylactic administration on the arginase activity of peritoneal macrophages in rat models of experimental Parkinsonism. Key: *—$p \leq 0.05$ versus the group of intact animals; #—$p \leq 0.05$ versus the group of animal models of Parkinsonism.

Another evidence of the ability of the drugs comprising microelements to prevent a pro-inflammatory shift in arginine metabolism in peritoneal macrophages in Parkinson's disease is also provided by the data on arginase activity of these cells. As it was mentioned above, arginase and NO-synthase are two enzymes that metabolize arginine by phagocytes. The arginine metabolic pathway is the main metabolic criterion for the functional polarization of phagocytes. An increase in the arginase activity is a sign of anti-inflammatory shift in metabolism in these cells, while an increase in the production of reactive nitrogen species is a criterion for their pro-inflammatory activation. According to our results, the arginase activity of peritoneal macrophages in rat models of Parkinsonism did not differ from that in intact animals, which, together with the increase in NO production, indicates a pro-inflammatory shift in metabolism in these cells. FIG. 17.

$^{64}Zn_e$-asp containing 10% of E2$^{85}Rb_e$ significantly increased arginase activity of peritoneal phagocytes which, along with a decrease in the production of reactive nitrogen species, indicates an anti-inflammatory metabolic profile of these cells. The zinc-based drug also contributed to an anti-inflammatory shift in arginine metabolism by peritoneal phagocytes, as evidenced by a decrease in NO synthesis and absence of any changes in arginase activity.

Figure 18A:
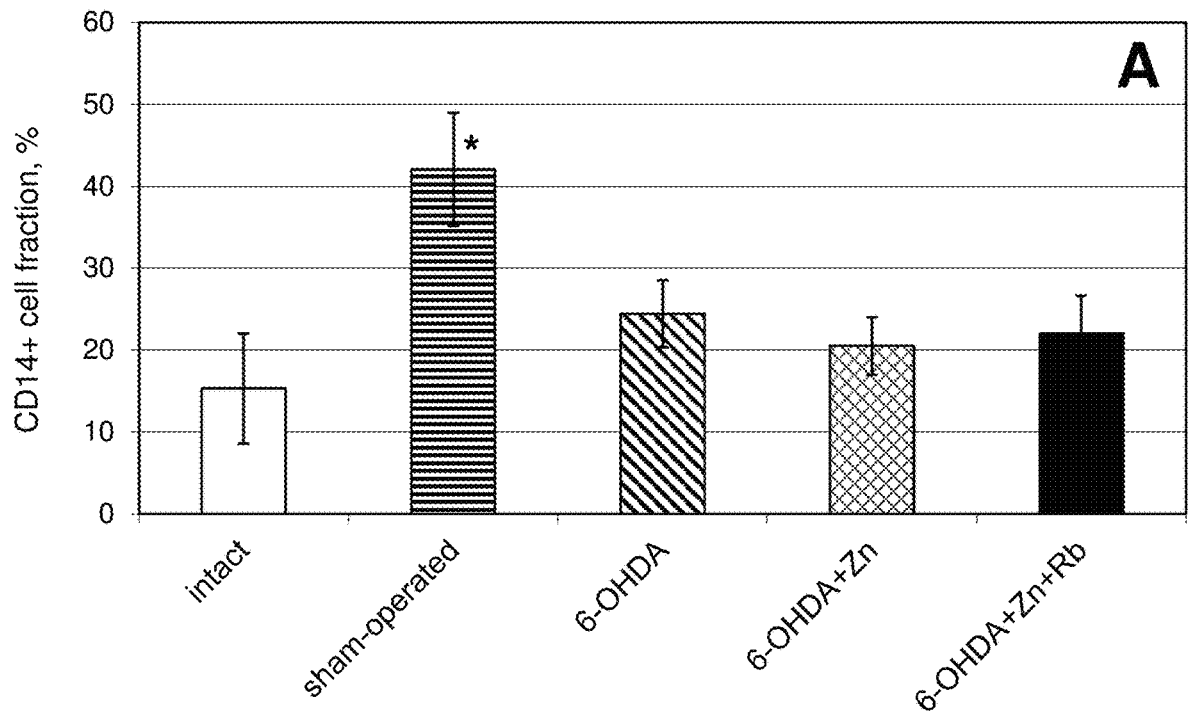
FIG. 18A and FIG. 18B show CD14 expression in a population of peripheral macrophages in rat models of experimental Parkinsonism that received preventive treatment with $^{64}Zn_e$-asp and $^{64}Zn_e$-asp containing 10% of E2$^{85}$Rb$_e$. Key: *—$p \leq 0.05$ versus the group of intact animals; #—$p \leq 0.05$ versus the control group of animal models of Parkinsonism.
Figure 18B:
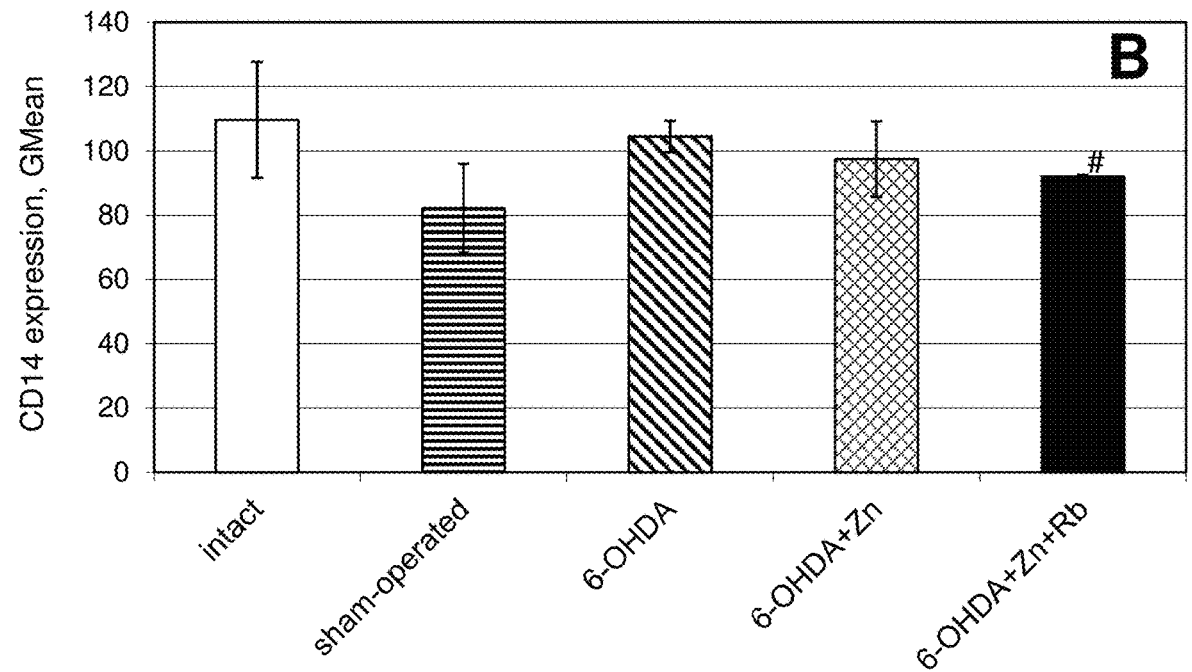

Analysis of the phenotypic profile of peritoneal macrophages confirmed their involvement in the development of the disease. To assess the phenotypic profile of peritoneal macrophages, we used the same phenotypic markers which were analyzed in phagocytes of microglia and circulating phagocytes. According to the results of our study, the expression of CD14 by peritoneal phagocytes did not change statistically significantly either under the conditions of the disease development or under the effect of the drugs comprising microelements, which is typical for resident tissue phagocytes for the CD14 expression on their membrane is at the physiological maximum (FIG. 18A and FIG. 18B).

CD14 expression in a population of peripheral macrophages in rat models of experimental Parkinsonism that received preventive treatment with $^{64}Zn_e$-asp and $^{64}Zn_e$-asp containing 10% of E2$^{85}Rb_e$. *—p 0.05 versus the group of intact animals; #—p 0.05 versus the control group of animal models of Parkinsonism.

Figure 19A:
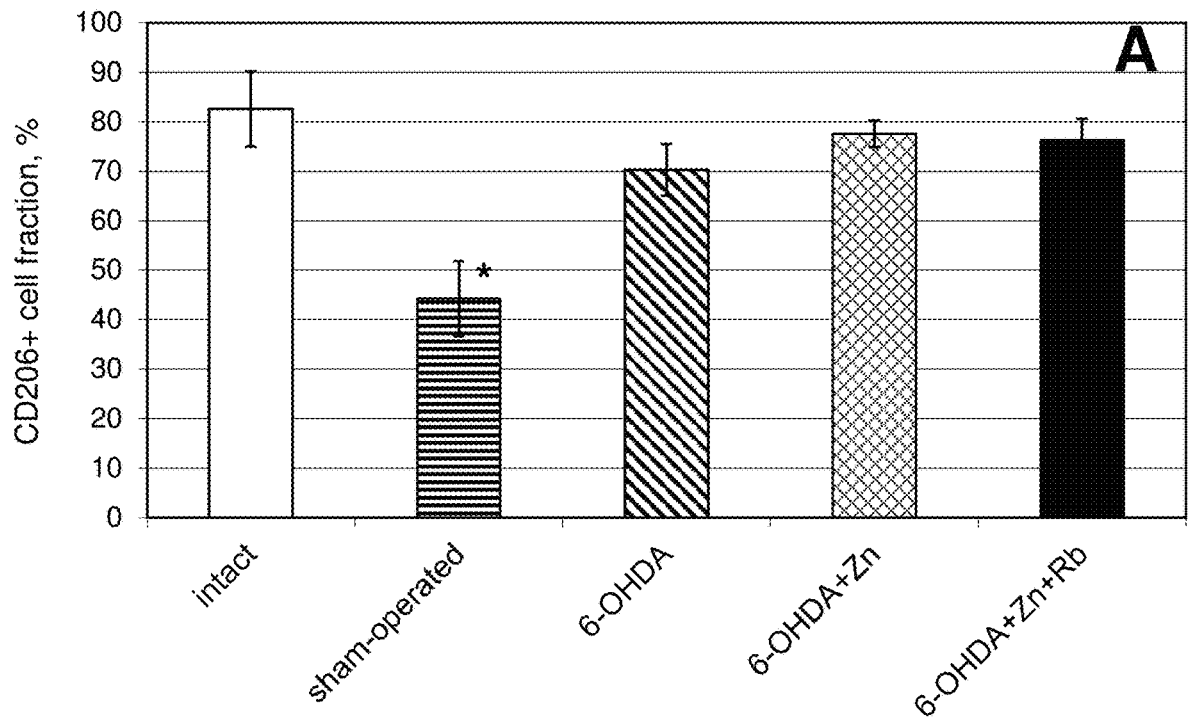
FIG. 19A and FIG. 19B show CD206 expression in the population of CD14+ peritoneal macrophages in rat models of experimental Parkinsonism that received preventive treatment with $^{64}Zn_e$-asp and $^{64}Zn_e$-asp containing 10% of E2$^{85}$Rb$_e$. Key: *—$p \leq 0.05$ versus the group of intact animals; #—$p \leq 0.05$ versus the control group of animal models of Parkinsonism.
Figure 19B:
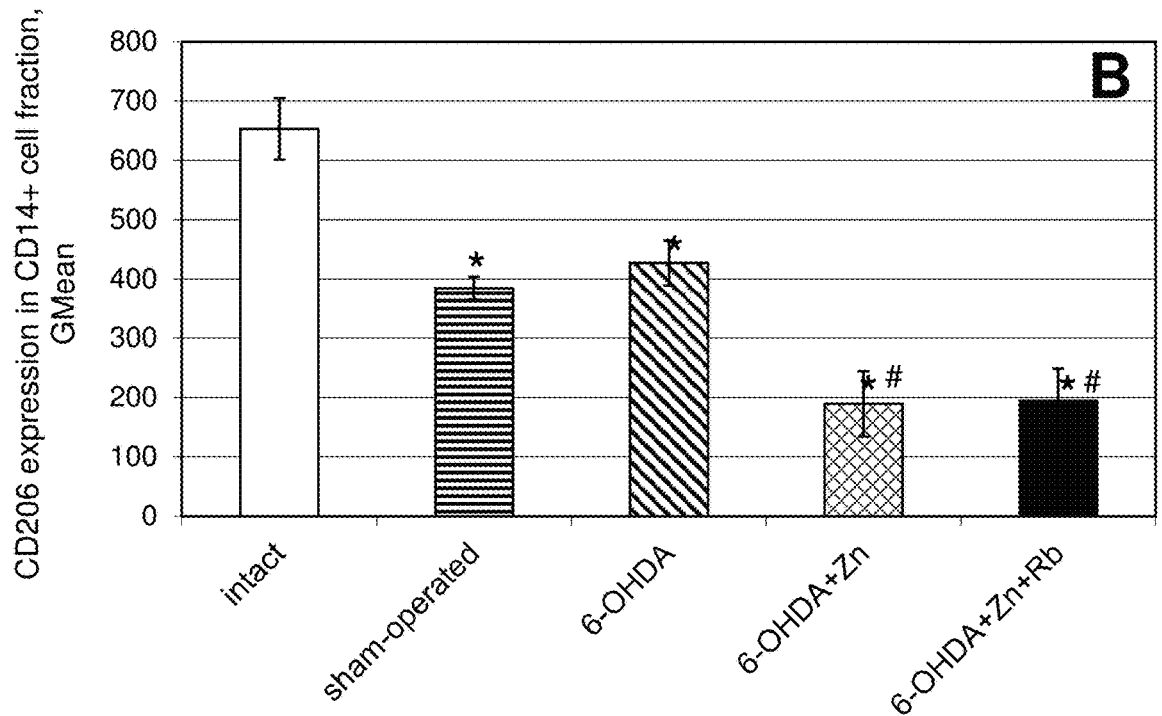

The fraction of CD206+ cells in the peritoneal cavity was rather low; therefore we analyzed the number of cells expressing this marker in the population of CD14+ peritoneal phagocytes. The results of the analysis showed that the fraction of peritoneal CD14+ phagocytes expressing CD206 did not change with the development of Parkinsonism (FIG. 19A). However, the level of expression of this marker was reduced in the animal models of Parkinson's disease in comparison with the intact animals.

Prophylactic administration of $^{64}Zn_e$-asp and $^{64}Zn_e$-asp containing 10% of E2$^{85}Rb_e$ was accompanied by a further decrease in the expression level of this marker in the population of peritoneal phagocytes, which is inconsistent with changes in the metabolic profile of the cells.

Findings in Example 1:
1. The development of experimental Parkinsonism is accompanied by changes in the functional and phenotypic profile of phagocytes of different localization with signs of their inflammatory activation.
2. Prophylactic systemic administration of $^{64}Zn_e$-asp and $^{64}Zn_e$-asp containing 10% of E2$^{85}Rb_e$ modulated metabolism and phenotypic profile of phagocytes of different localization in the animal models of Parkinsonism reducing the inflammatory metabolic shift in cells which occurred against the background of a decrease in the level of destruction of dopaminergic neurons in the animals.
3. The nature of modulating effects of the drugs comprising microelements on phagocytes differed depending on their localization and degree of maturity. Microglial cells in the animals receiving the drugs were characterized by activation of an anti-inflammatory (reparative) pathway. Prophylactic administration of the drugs prevented metabolic and phenotypic shifts in circulating phagocytes which are usually recruited to the brain during neurodegenerative disorders, which also was one of the reasons which caused reduction in the destruction of neurons in the black substance. Administration of the drugs prevented pro-inflammatory activation of phagocytes in the peritoneal cavity. The mechanism of this phenomenon can be complex, involving the effects of the drugs on the cells of immune system as well as on the microbiota and the intestine epitheliocytes, which may result in prevention of the formation of the pathological gut-brain axis. Analysis of such a complex effect calls for a study of the effects of the drugs on the intestinal barrier integrity, translocation of intestinal microorganisms and their metabolism.
4. The functional status and quantitative parameters of peripheral blood phagocytes can be considered as a sensitive criterion to monitor the effectiveness of $^{64}Zn_e$-asp and $^{64}Zn_e$-asp containing 10% of E2$^{85}Rb_e$ in neurodegenerative disorders. In these calculations, the mass characteristics of pure elements are used—$^{64}Zn_e$ and $^{85}Rb_e$. For example, 9 parts of $^{64}Zn_e$ and 1 part of $^{85}Rb_e$ in the mixture means that calculations are based on the masses of pure elements—9 parts of the $^{64}Zn_e$ pure element and 1 part of the $^{85}Rb_e$ pure element.

Example 2. Effects of $^{64}Zn_e$-Asp and E2+$^{85}Rb_e$ Preparations on the Metabolic Profile of Nonsensitized Mouse Peritoneal Macrophages Materials and methods: Peritoneal macrophages (PM) were isolated from the peritoneal cavity of male mice of c57/B6 line with an average body weight of 22 g without previous sensibilization. The metabolic profile of phagocytes was characterized by the arginine metabolic pathway (by the levels of arginase activity and NO synthesis measured using photocolorimetric methods), the level of formation of intracellular reactive oxygen species (ROS) by esterases and phagocytic activity measured using flow cytometry as well as the levels of NADH and NADPH oxidase activation, as determined in the NBT test. Duration of treatment of a standardized suspension of nonsensitized macrophages from the peritoneal cavity varied depending on the methodological characteristics of metabolic response. A 90 minute exposure to the drugs according to Kim D K, Pfeifer J. *Surg Forum.* 1977; 28:85-7 was used to analyze their effects on oxidative metabolism and phagocytic activity. An 18 hour exposure according to Lastra M D, et al., *J Trace Elem Med Biol.* 2001; 15(1):5-10 was used to analyze the effects on arginine metabolic pathway. To analyze the effects of the drugs under study on the induced (stimulated) metabolic activity of phagocytes, the cells were treated with lipopolysaccharide (LPS) from *E. coli* (Sigma, USA) according to Haddad J J. *Mol Immunol.* 2009; 47(2-3):205-14. doi: 10.1016/j.molimm.2009.09.034.

Figure 20:
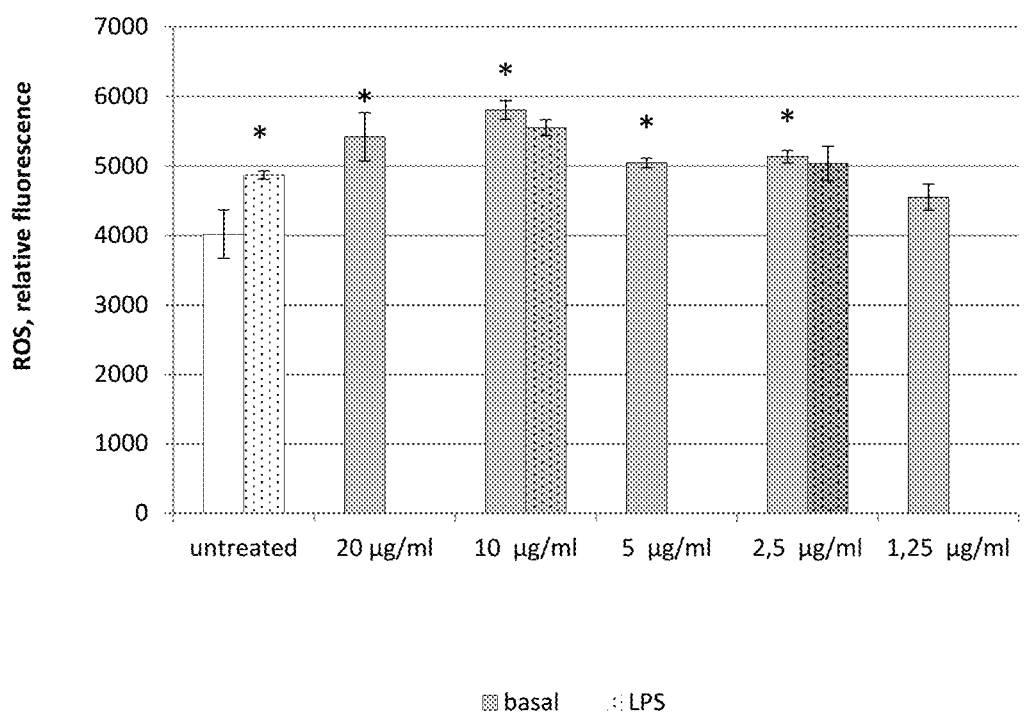
FIG. 20 shows the effects of $^{64}Zn_e$-asp on intracellular ROS production by nonsensitized and bacterial lipopolysaccharide-treated peritoneal macrophages. Key: *—$p \leq 0.05$ versus unstimulated cells.

Results:

PM treatment with $^{64}Zn_e$-asp for 90 min. had a moderate stimulating effect on spontaneous and LPS-stimulated ROS production by macrophages (FIG. 20). Treatment with the drug at a concentration of 10 µg/ml caused more expressive stimulation of ROS generation than after treatment with LPS. There was no clear dose-response relationship.

Figure 21:
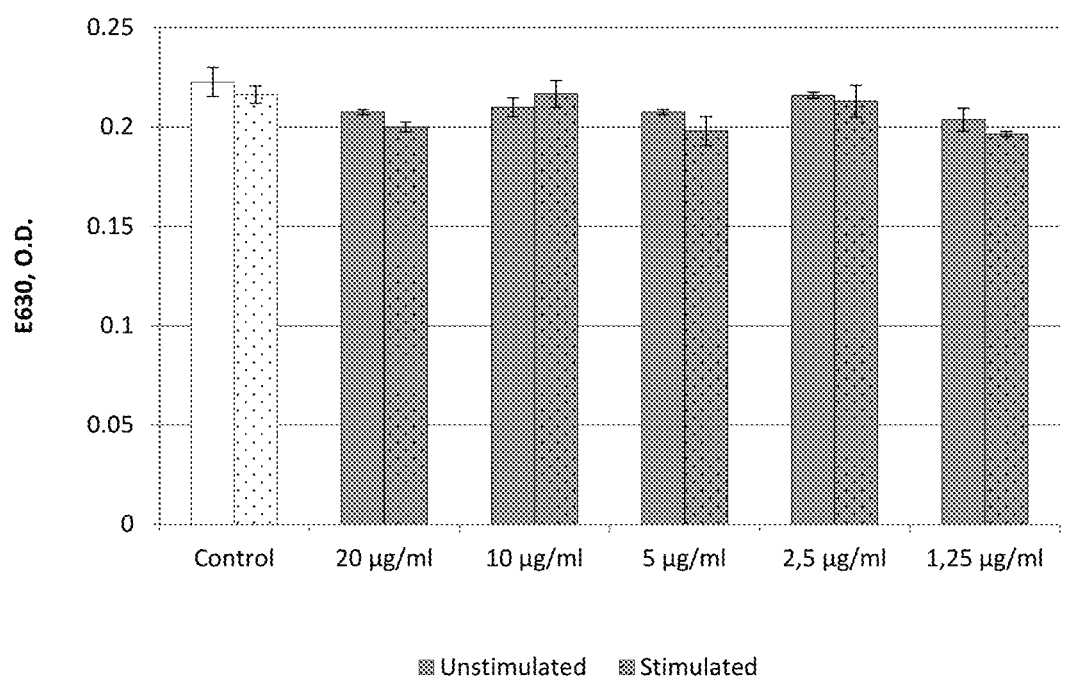
FIG. 21 shows the effects of $^{64}Zn_e$-asp on nitroblue Tetrazolium (NBTtest indices of nonsensitized and bacterial lipopolysaccharide-treated peritoneal macrophages.

90-minute cell treatment with the drug did not have a statistically significant effect either on the spontaneous or induced state of the hexose monophosphate shunt in peritoneal macrophages (activation of NADH and NADPH oxidases) (FIG. 21).

It should be noted that after 90 minutes of exposure of PM to the action of LPS did not change the levels of NADH and NADPH oxidase activation by peritoneal phagocytes, which may be due to insufficient treatment duration.

Figure 22:
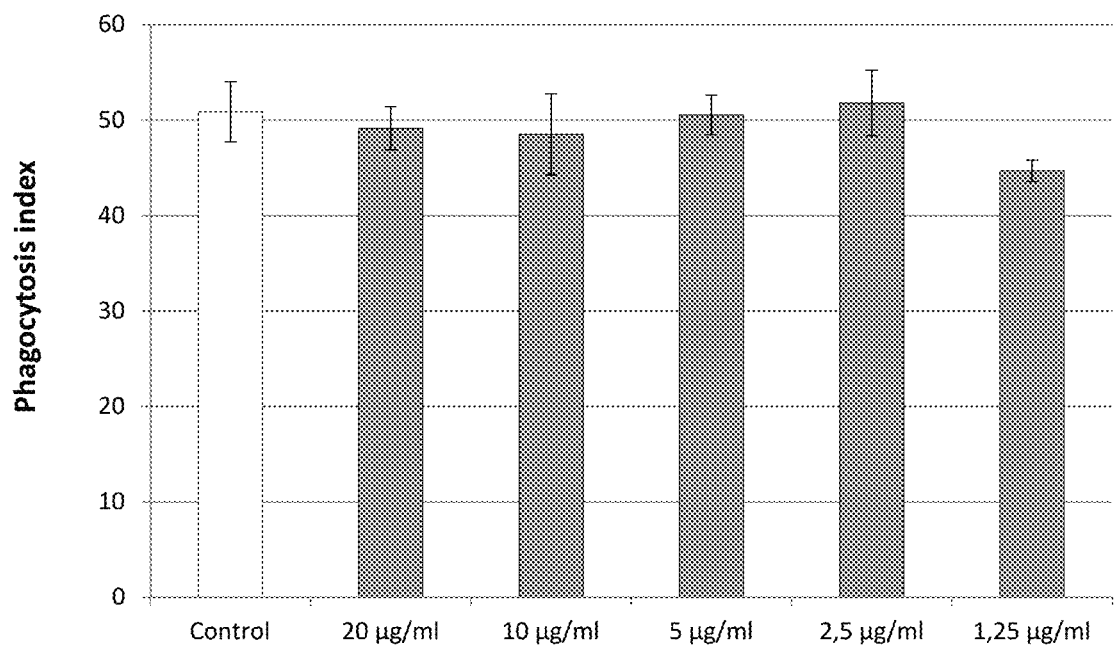
FIG. 22 shows the effects of $^{64}Zn_e$-asp on phagocytosis of nonsensitized peritoneal macrophages.

The drug comprising a stable isotope of zinc did not have a significant effect on phagocytic activity of the nonsensitized PM (FIG. 22).

A tendency towards a slight decrease in the intensity of endocytosis of the treated cells was observed only after using the drug at the lowest concentration.

Figure 23:
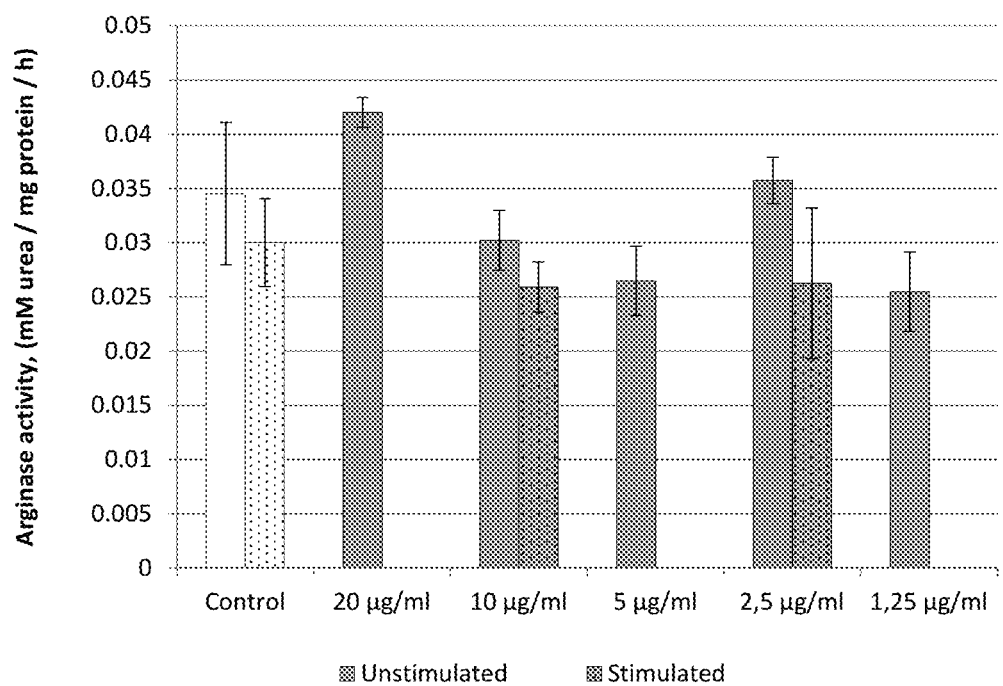
FIG. 23 shows the effects of $^{64}Zn_e$-asp on arginase activity of nonsensitized and bacterial lipopolysaccharide-treated peritoneal macrophages.

Ability of the drug to produce a multidirectional weak effect on arginase activity at the tendency level was observed after an 18-hour treatment of PM with the drug (FIG. 23).

It should be noted that there was a significant variability in the values of the optical density within each option of the experiment. In the concentration range of 5-20 µg/ml, a tendency to an insignificant dose-dependent decrease in arginase activity of the treated cells was observed. A further decrease in the concentration was accompanied by a loss of dose-response relationship.

No statistical significance of the said effects was present.

Figure 24:
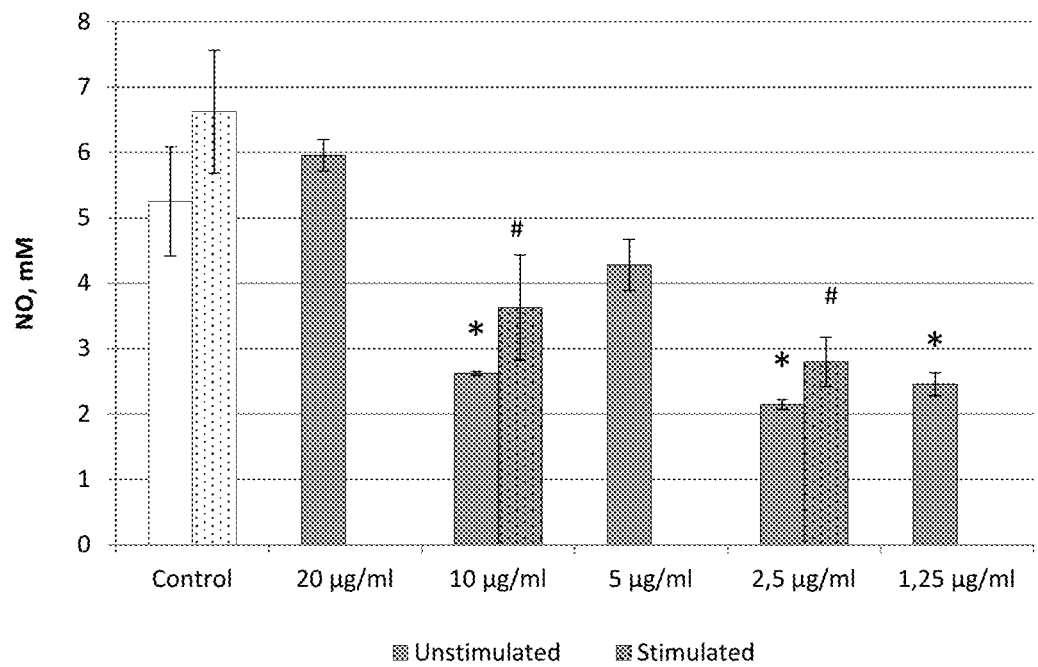
FIG. 24 shows the effects of $^{64}Zn_e$-asp on NO production by nonsensitized and bacterial lipopolysaccharide-treated peritoneal macrophages. Key: *—$p \leq 0.05$ versus unstimulated cells; #—$p \leq 0.05$ versus cells stimulated by bacterial lipopolysaccharide.

$^{64}Zn_e$-asp produced the most pronounced modulatory effect on the production of reactive nitrogen species by peritoneal phagocytes (FIG. 24).

18-hour exposure of cells to the drug at the concentration range from 1.25 to 10 g/ml resulted in statistically significant inhibition of spontaneous production of reactive nitrogen species by PM. There was no dose-response relationship. Treatment of bacterial LPS-stimulated cells with the preparation comprising a stable isotope of zinc also caused a statistically significant reduction in NO synthesis. A tendency towards inversely proportional dose dependence of the inhibitory effect of zinc-based drug on the production of reactive nitrogen species induced by phagocytes was recorded.

Figure 25:
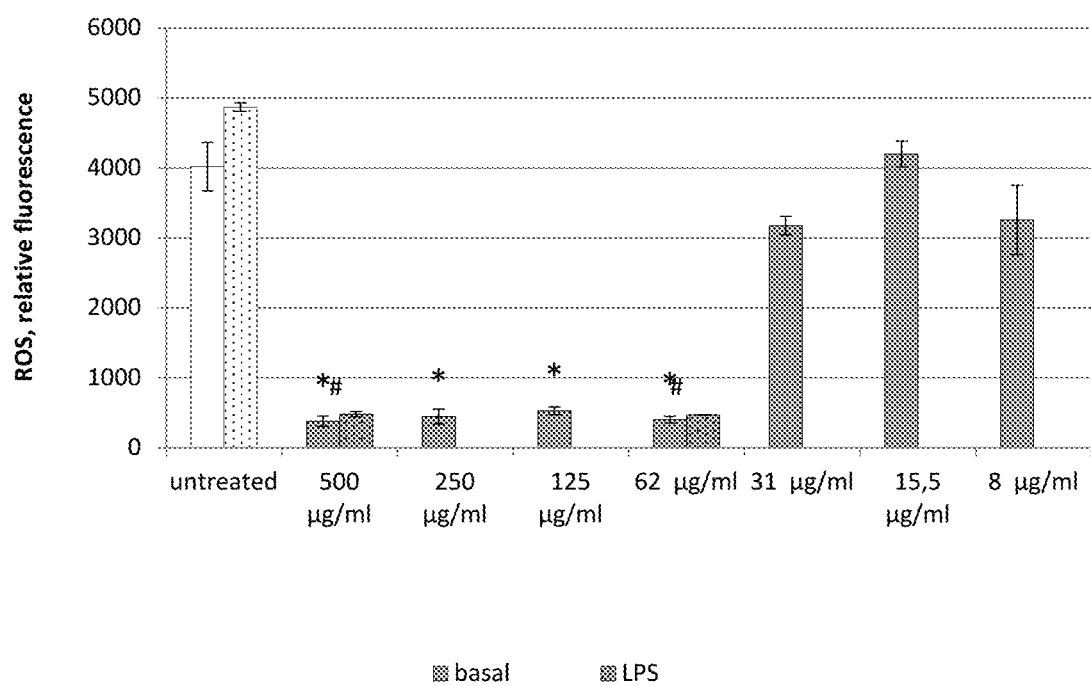
FIG. 25 shows the effects of E2+$^{85}$Rb$_e$ on intracellular ROS production by nonsensitized and bacterial lipopolysaccharide-treated peritoneal macrophages. Note: *—$p \leq 0.05$ versus unstimulated cells; #—$p \leq 0.05$ versus bacterial lipopolysaccharide-stimulated cells.

A modulatory effect of the E2+$^{85}Rb_e$ compound on the metabolic activity of peritoneal phagocytes was more pronounced than that of $^{64}Zn_e$-asp. The 90-minute exposure of nonsensitized PM to the drug at the concentration range of 62-500 µg/ml caused a sharp inhibition of spontaneous ROS production by them as a result of activation of esterases (FIG. 25). No dose-response relationship was observed. Addition of the drug (E2+$^{85}Rb_e$) at concentrations of 8, 15.5 and 31 µg/ml did not cause any statistically significant changes in the spontaneous realization of the metabolic function by cells.

E2+$^{85}Rb_e$, used at the same concentration range, caused a sharp inhibition of the induced (bacterial LPS-stimulated) intracellular ROS generation by peritoneal phagocytes. No dose-response relationship was observed. FIG. 25.

Figure 26:
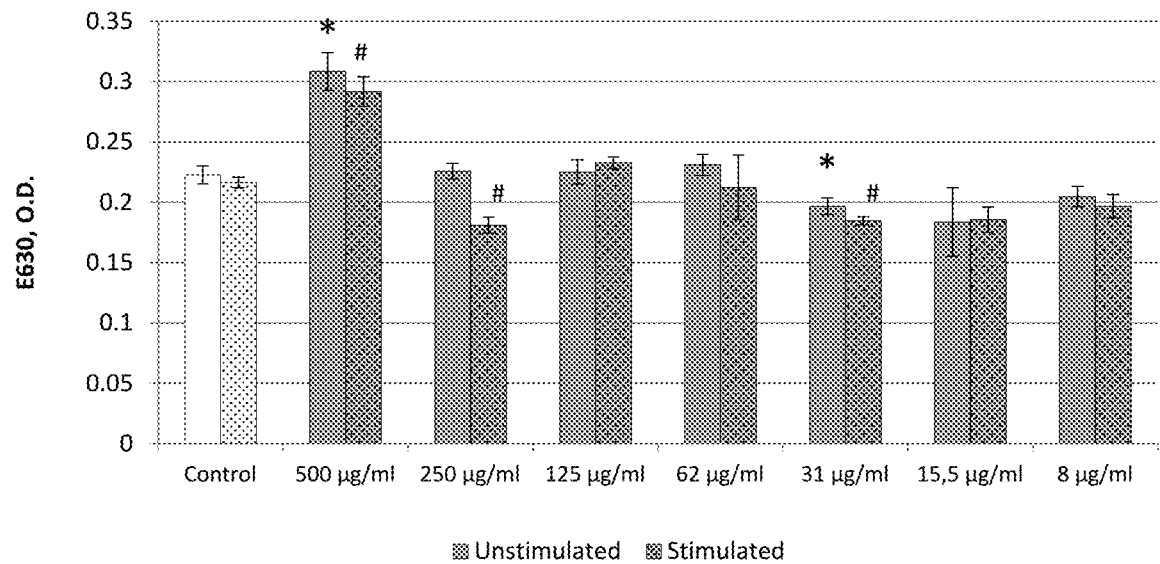
FIG. 26 shows the effects of E2+$^{85}$Rb$_e$ on NBT test indices of nonsensitized and bacterial lipopolysaccharide-treated peritoneal macrophages. Key: *—$p \leq 0.05$ versus unstimulated cells; #—$p \leq 0.05$ versus bacterial lipopolysaccharide-stimulated cells.

The nature of the effect of E2+$^{85}Rb_e$ on activation of NADH and NADPH oxidases of PM (FIG. 26) differed from that on the creation of reactive metabolites of oxygen by esterases (FIG. 26). Used at a concentration of 500 µg/ml, the drug caused a slight increase in the oxidase activity of phagocytes. All concentrations of the drug below 500 µg/ml produced no statistically significant effect on this index of metabolic activity of PM. The nature of the effect of the drug on the induced (LPS-stimulated) oxidase activity was similar to that on the spontaneous realization of this function by cells. When used in lower concentrations, the drug demonstrated a tendency towards an ability to reduce the formation of reactive oxygen species by oxidases. However, taking into account an insignificant level of the effect and disproportionate fluctuation of its direction depending on the concentration, it should be considered non-specific and attributed to the variability of optical densities. FIG. 26.

Figure 27:
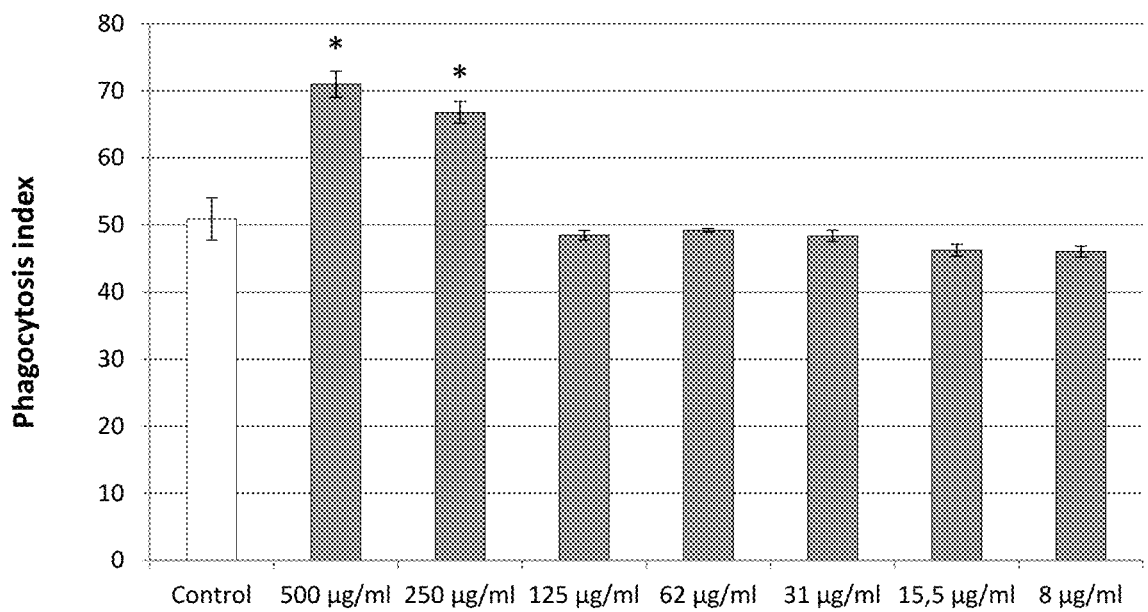
FIG. 27 shows the effects of E2+$^{85}$Rb$_e$ on phagocytosis of nonsensitized peritoneal macrophages. Key: *—$p \leq 0.05$ versus unstimulated cells.

The drug comprising a stable isotope of rubidium produced a similar effect on the phagocytic activity of nonsensitized peritoneal phagocytes (FIG. 27). When used at concentrations of 500 and 250 µg/ml, it moderately strengthened endocytosis of peritoneal phagocytes. A decrease in the drug concentration was accompanied by absence of its influence on this index of metabolism in PM.

Figure 28:
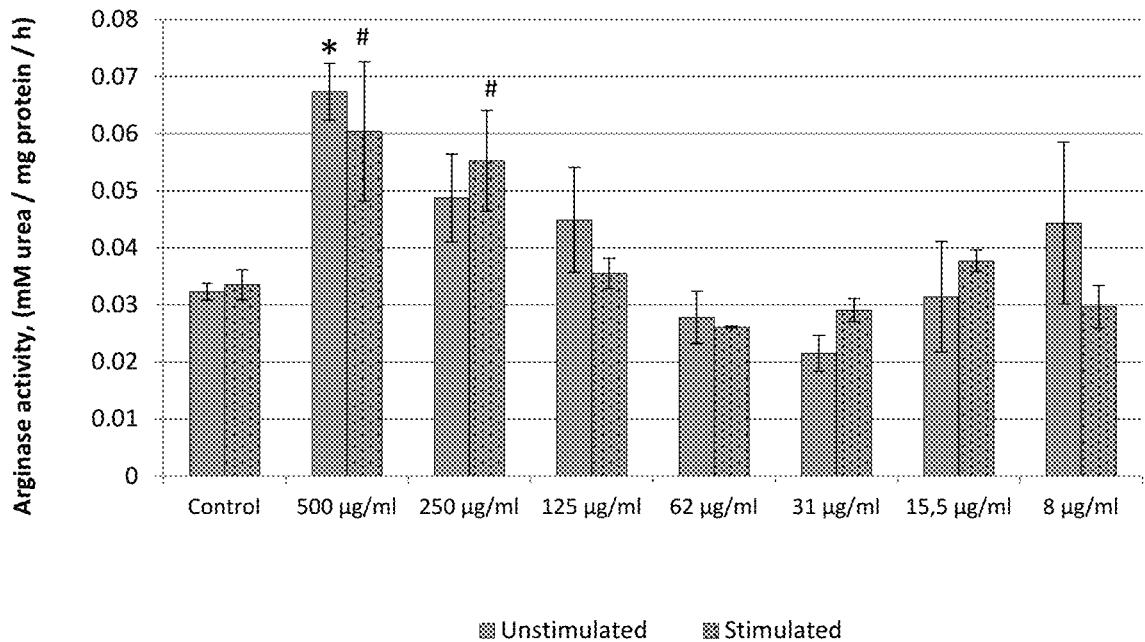
FIG. 28 shows the effects of E2+$^{85}$Rb$_e$ on arginase activity of nonsensitized and bacterial lipopolysaccharide-treated peritoneal macrophages. Key: *—$p \leq 0.05$ versus unstimulated cells; #—$p \leq 0.05$ versus bacterial lipopolysaccharide-stimulated cells.

The use of E2+$^{85}Rb_e$ at concentrations of 500 and 250 µg/ml with the 18-hour exposure caused a statistically significant increase in PM arginase activity (FIG. 28). A stimulating effect of the drug on this metabolic indicator of phagocytes did not depend on additional treatment of the cells with bacterial LPS and was more expressive in comparison with the effect on the phagocytic function of cells. The dose dependence of the modulatory effect of E2+$^{85}Rb_e$ on the arginase activity of PM was not statistically valid.

Figure 29:
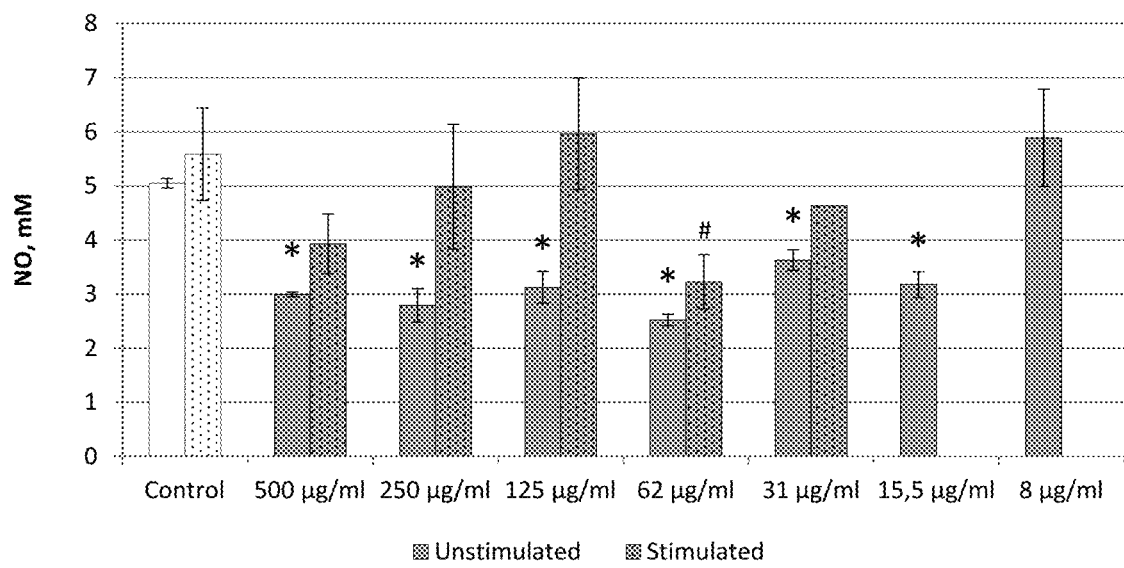
FIG. 29 shows effects of E2+$^{85}$Rb$_e$ on NO synthesis by nonsensitized and bacterial lipopolysaccharide-treated peritoneal macrophages. Key: *—$p \leq 0.05$ versus unstimulated cells; #—$p \leq 0.05$ versus bacterial lipopolysaccharide-stimulated cells.

The most expressive effect of E2+$^{85}Rb_e$, as with $^{64}Zn_e$-asp, was recorded to be produced on the generation of reactive nitrogen species by PM after the 18-hour exposure (FIG. 29).

Used at all the above mentioned concentrations, except for 8 µg/ml, the drug inhibited spontaneous production of reactive nitrogen species by PM. No dose-response relationship was observed. The drug also showed a tendency to weaken the induced production of NO by cells treated with bacterial LPS, also without dose-response relationship.

Findings on Example 2.
1. Both drugs under study have an anti-inflammatory modulatory effect on the metabolic profile of nonsensitized and bacterial LPS-stimulated peritoneal phagocytes. This conclusion is justified by changes in the effects of the drugs on the arginine metabolic pathway in phagocytes towards a sharp decrease in the generation of reactive nitrogen species which are a product of arginine metabolism by inducible NO synthase (iNOS). Reactive oxygen species are powerful mediators of inflammatory reactions and signaling molecules involved in the activation of apoptosis. Reduced activity of iNOS characterizes phagocytes of the alternative phenotype (M2). There is no clear dose-response relationship.
2. A more pronounced effect was recorded to be produced by the drug containing a stable isotope of rubidium, which also showed powerful antioxidant activity.
3. A high level of variability of some variables during the study may be a consequence of unstable solubility of both preparations in polar solvents (saline), especially the zinc-based preparation.

The lack of immunomodulating effect of zinc-based preparation may also be caused by insufficient exposure of cells to the drug. In this connection, it is advisable to carry out an additional in vivo study of the effects of the drugs on oxidative metabolism of phagocytes using intact animals which will enable a longer effect of the factor on this cell function, since in vitro studies are limited by methodological conditions.

Figures 30A, 30B, 30C:
FIGS. 30A-30C show stages of collection of brain tissue samples for the isolation of microglial cells.
Figure 31:
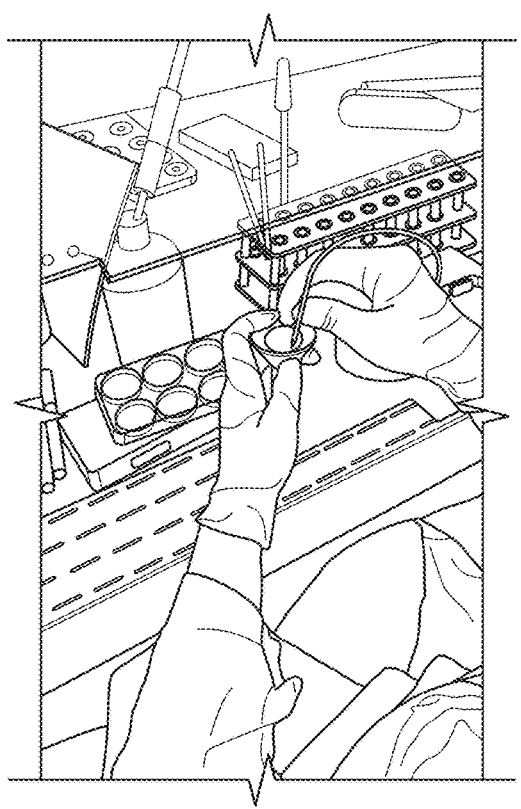
FIG. 31 shows making homogenate of brain tissue by mechanical disintegration using coolants.
Figure 32:
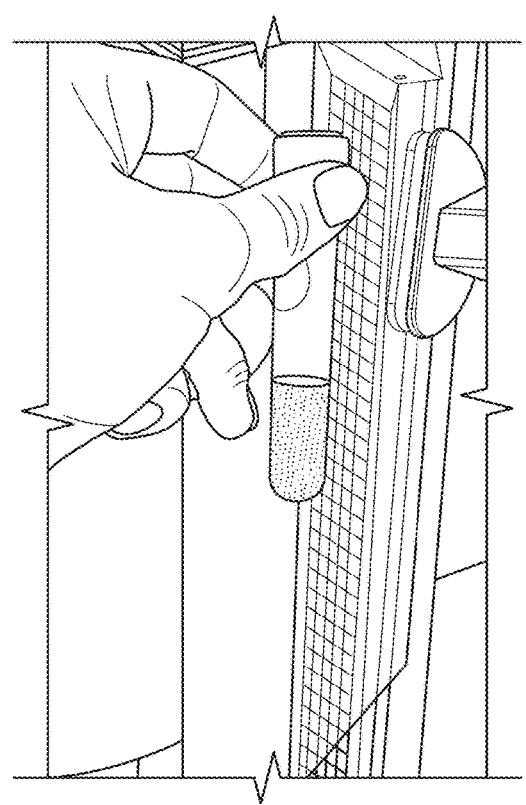
FIG. 32 shows the fractionation of homogenate of brain tissue in Percoll gradient.
Figure 33A:
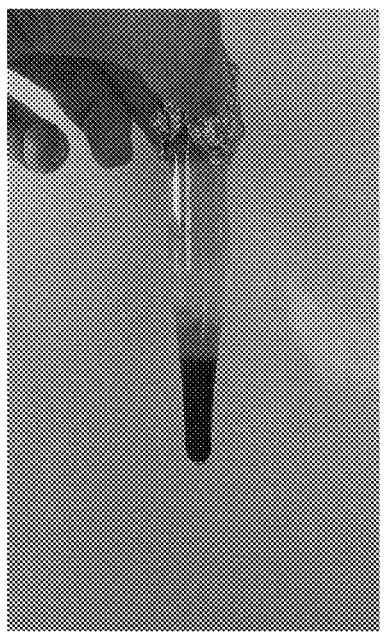
FIG. 33A and FIG. 33B show separation of circulating phagocytes using density gradient.
Figure 33B:
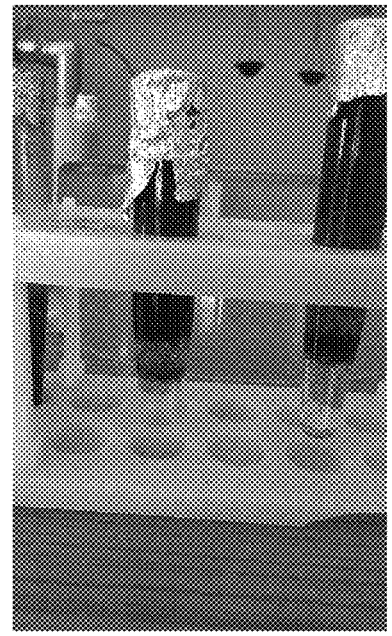

Example 3. Effects of $^{64}Zn_e$-Asp and E2+$^{85}Rb_e$ Preparations on the Metabolic Profile of Nonsensitized Microglial Cells, Circulating Monocytes and Neutrophils in Healthy Rats Materials and methods: Rat microglial cells were isolated by mechanical (cell sieves) disintegration of the brain tissue (FIG. 30A, FIG. 30B and FIG. 30C) followed by fractionation of the tissue homogenate in Percoll density gradient (Microglia: Methods and Protocols, Edited by Bertrand Josef and Jose Luis Venero, Springer protocol. Humana Press, 2013, 350 p.) (FIG. 31). Before the collection of the brain tissue, decapitation was performed to avoid hemorrhage to the brain during sampling (FIG. 32). Decapitation was performed immediately after anesthesia to minimize the death of brain tissue, including microglial cells. All manipulations for the isolation of microglial cells were carried out using coolants. Circulating neutrophils were isolated from venous blood taken into a tube containing EDTA in a two-step Percoll gradient (Alsharif K F et al. Vascul Pharmacol. 2015 August; 71:201-7. doi: 10.1016/j.vph.2015.02.006) (FIG. 33A and FIG. 33B). Circulating monocytes were isolated from venous blood collected into a tube containing heparin in a two-step Hypaque gradient (Macrophages and dendritic cells: Methods and Protocols, Edited by Neil E. Reiner, NY, Humana Press, 2009: 368 P). The metabolic profile of phagocytes was characterized based on the pathway of arginine metabolism (levels of arginase activity and NO synthesis measured using photocolorimetric methods), the level of formation of intracellular reactive oxygen species (ROS) by esterases and the indices of phagocytic activity determined by flow cytofluorimetry, as well as according to the activation levels of NADH and NADPH oxidases determined in NBT test. Duration of treatment of phagocytes of all the above mentioned populations varied depending on the methodological characteristics of metabolic response. A 90 minute exposure to the drugs according to Kim et al., 1977 (cited above) was used to analyze their effects on oxidative metabolism and phagocytic activity. An 18 hour exposure according to Lastra et al., 2001 (cited above) was used to analyze the drug effects on arginine metabolic pathway. To analyze the effects of the drugs under study on the induced (stimulated) metabolic activity of phagocytes, the cells were treated with lipopolysaccharide (LPS) from *E. coli* (Sigma, USA) according to Haddad et al., 2009 (cited above).

Results:

Microglia

Figure 34:
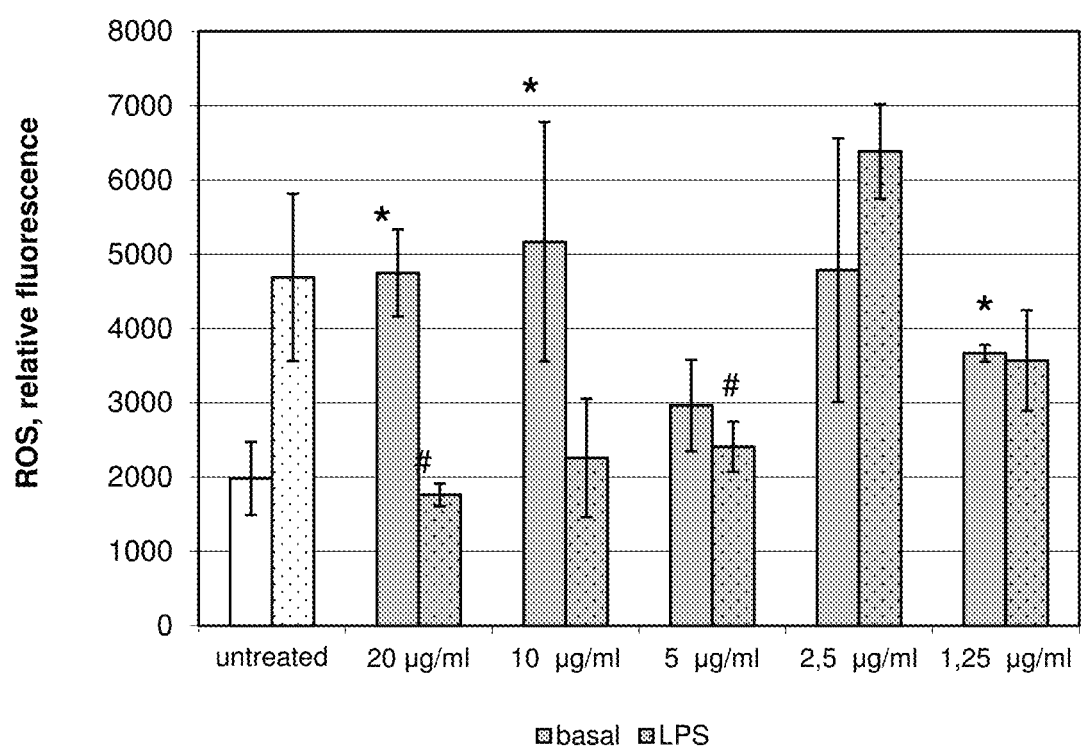
FIG. 34 shows the effects of $^{64}Zn_e$-asp on intracellular ROS production by nonsensitized rat microglial cells. Key: *—$p \leq 0.05$ versus untreated cells; #—$p \leq 0.05$ versus bacterial lipopolysaccharide-stimulated cells.

Treatment of nonsensitized microglial cells with $^{64}Zn_e$-asp had a multidirectional effect on spontaneous and LPS-stimulated generation of intracellular ROS in the absence of a clear dose-response relationship (FIG. 34). At concentrations of 20 and 10 µg/ml, the drug stimulated esterase-dependent oxidative metabolism in microglial cells, whereas at concentrations ≤5 µg/ml it had no statistically significant effect on this index. At concentrations of 20 and 5 µg/ml, the drug significantly inhibited ROS production stimulated by LPS. When used in other concentrations, it did not have any effect on the induced esterase-dependent oxidative metabolism in the cells under study.

Figure 35:
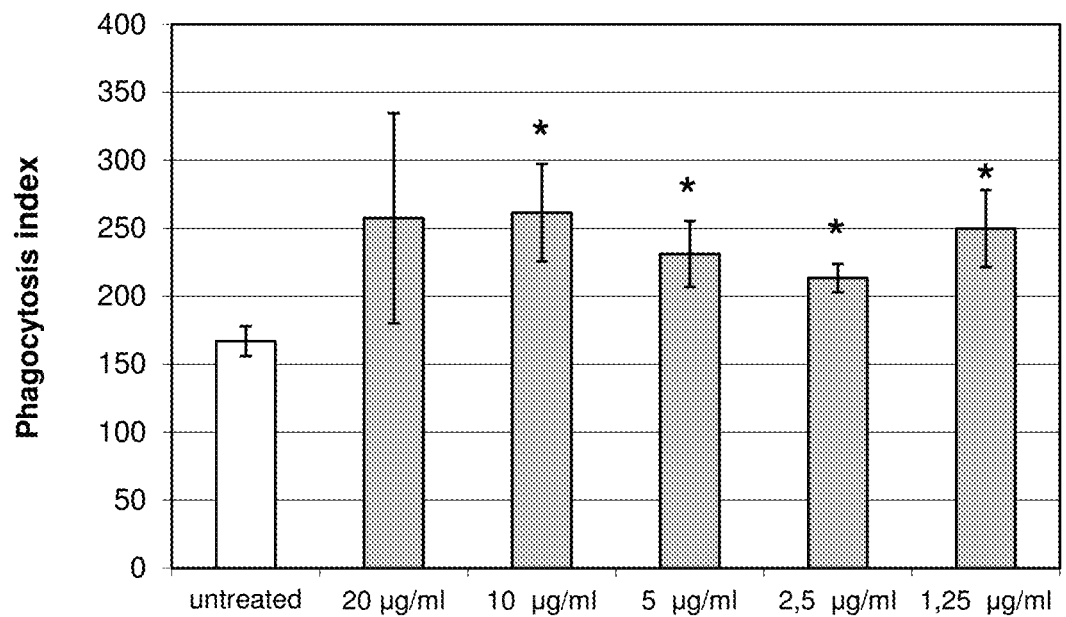
FIG. 35 shows the effects of $^{64}Zn_e$-asp on phagocytic activity of nonsensitized rat microglial cells. Key: *—$p \leq 0.05$ versus untreated cells.

At all the concentrations studied, the drug moderately increased phagocytic activity of microglial cells, without affecting the number of phagocytic cells in the population (FIG. 35). No clear dose-response relationship was observed.

Under normal, resident phagocytes of microglia are characterized by a low level of phagocytic activity. Its increase is a sign of functional activation of these cells.

Figure 36:
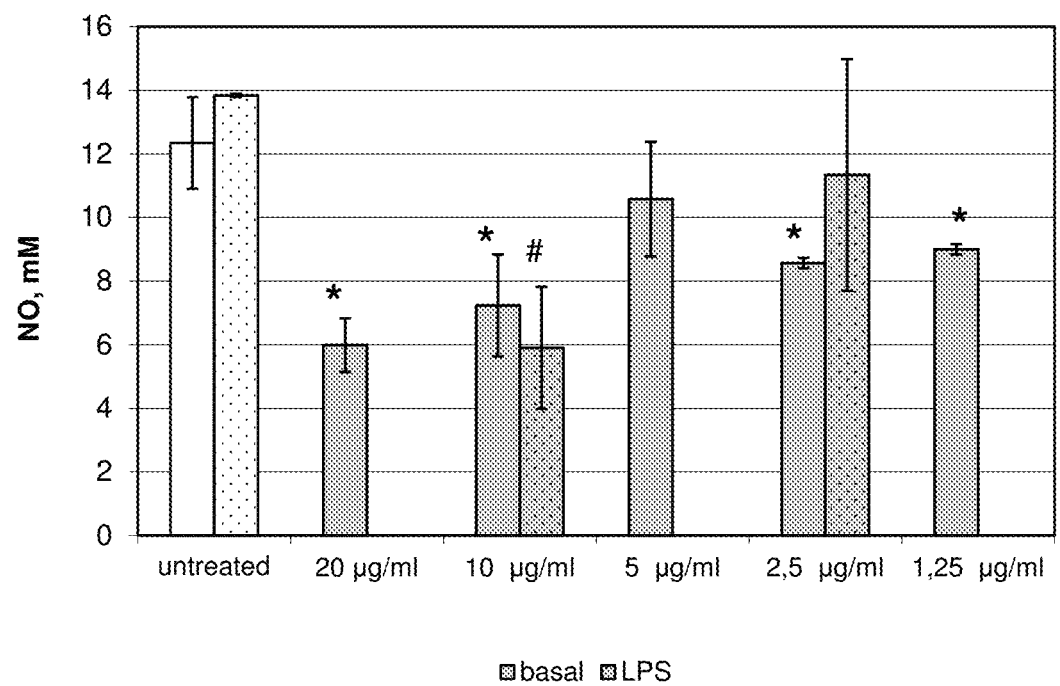
FIG. 36 shows the effects of $^{64}Zn_e$-asp on NO production by nonsensitized rat microglial cells. Key: *—$p \leq 0.05$ versus untreated cells; #—$p \leq 0.05$ versus bacterial lipopolysaccharide-stimulated cells.

Regardless of the concentration, the drug reduced spontaneous nitric oxide production by glial cells (FIG. 36). There was a weakly expressed inversely proportional dose-response relationship. At a concentration of 10 µg/ml, the drug also decreased the stimulated activity of NO synthase statistically significantly, as evidenced by a decrease in the synthesis of nitrites.

Figure 37:
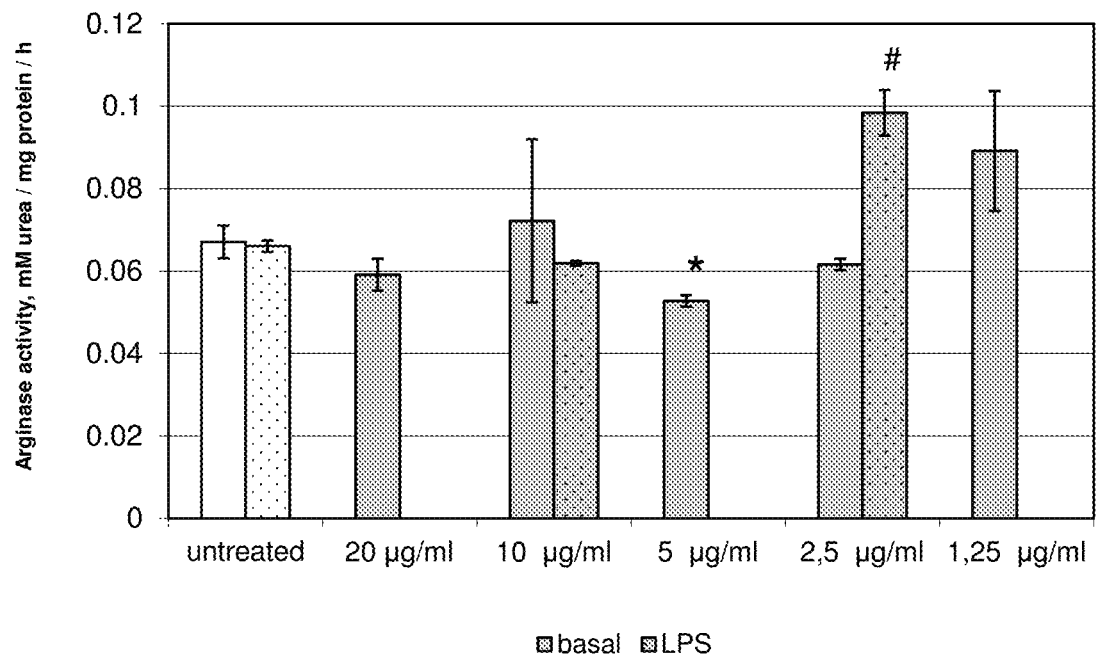
FIG. 37 shows the effects of $^{64}Zn_e$-asp on arginase activity of nonsensitized rat microglial cells. Key: *—$p \leq 0.05$ versus untreated cells; #—$p \leq 0.05$ versus bacterial lipopolysaccharide-stimulated cells.

Regardless of the concentration, the drug had virtually no effect on the spontaneous arginase activity of microglial cells (FIG. 37). On the background of LPS treatment, at a concentration of 2.5 µg/ml, the drug moderately strengthened this metabolic function of the brain phagocytes.

The absence of effect on arginase activity in combination with the inhibitory effect on the synthesis of nitrites is indicative of an anti-inflammatory modulatory effect of the drug on this population of phagocytes.

Peripheral Blood Monocytes

Figure 38:
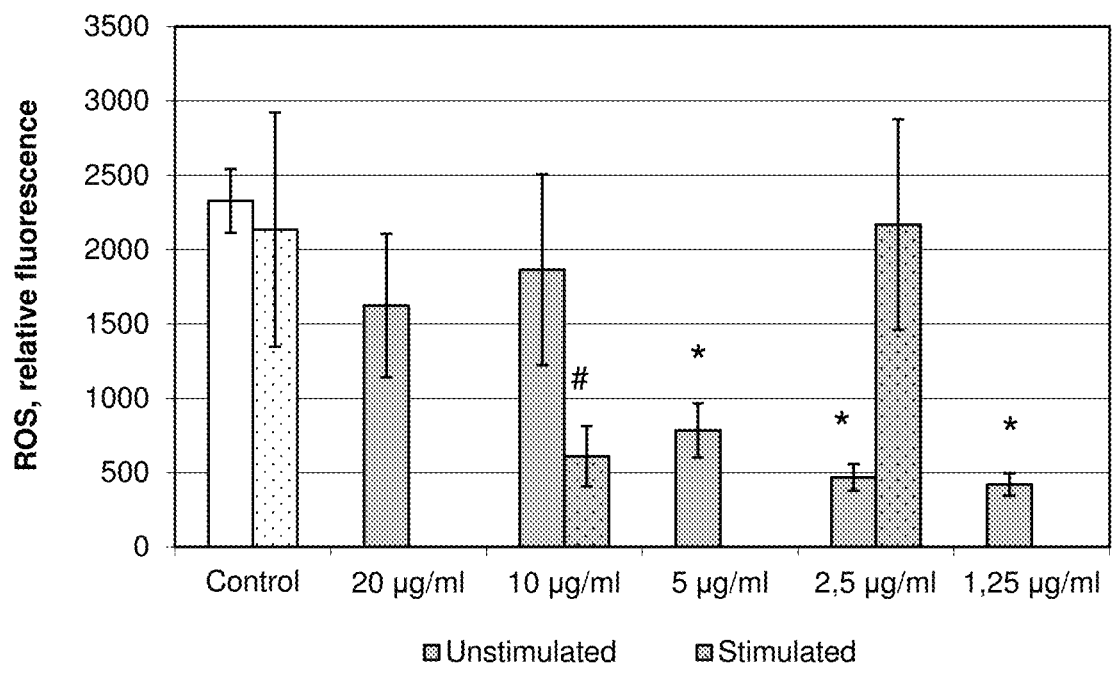
FIG. 38 shows the effects of $^{64}Zn_e$-asp on intracellular ROS production by nonsensitized rat peripheral blood monocytes. Key: *—$p \leq 0.05$ versus untreated cells; #—$p \leq 0.05$ versus bacterial lipopolysaccharide-stimulated cells.

Treatment of peripheral blood monocytes with $^{64}Zn_e$-asp resulted in a decrease in spontaneous esterase-dependent intracellular ROS production by cells. A weakly expressed inversely proportional dose-response relationship was observed (FIG. 38).

At a concentration of 10 µg/ml, the drug statistically significantly reduced this metabolic function of bacterial LPS-treated cells.

Figure 39:
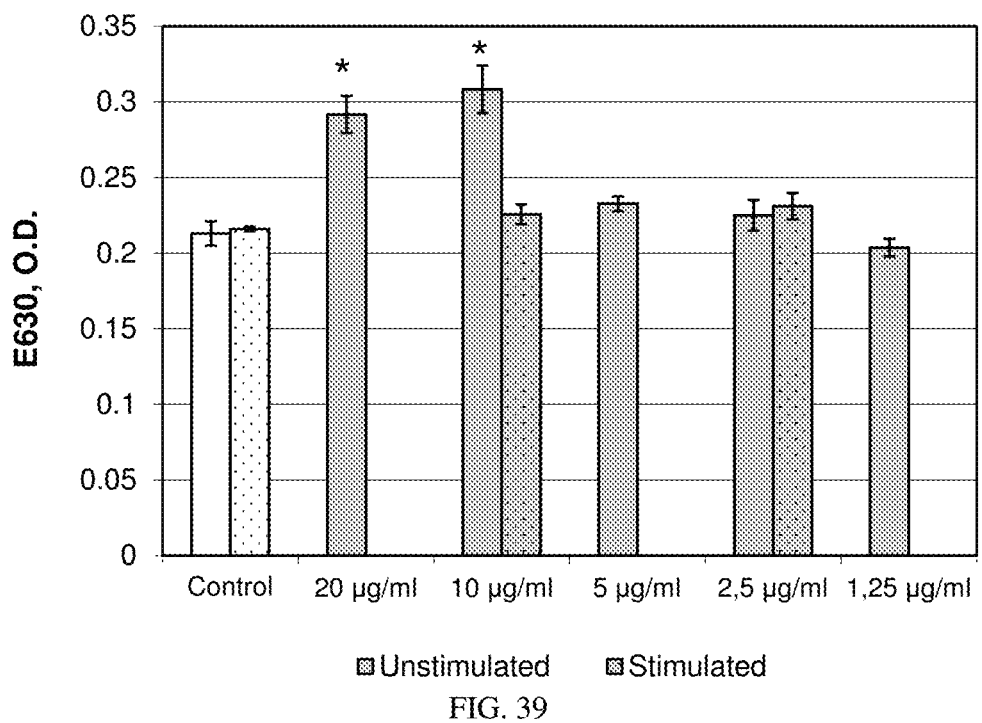
FIG. 39 shows the effects of $^{64}Zn_e$-asp on NBT test indices of nonsensitized rat peripheral blood monocytes. Key: *—$p \leq 0.05$ versus unstimulated cells.

At the same concentration, the drug slightly increased spontaneous oxidative metabolism in peripheral blood monocytes dependent on NADH and NADPH oxidases (FIG. 39).

The drug had no effect on the LPS-stimulated oxidase-dependent respiratory burst of monocytes.

Figure 40:
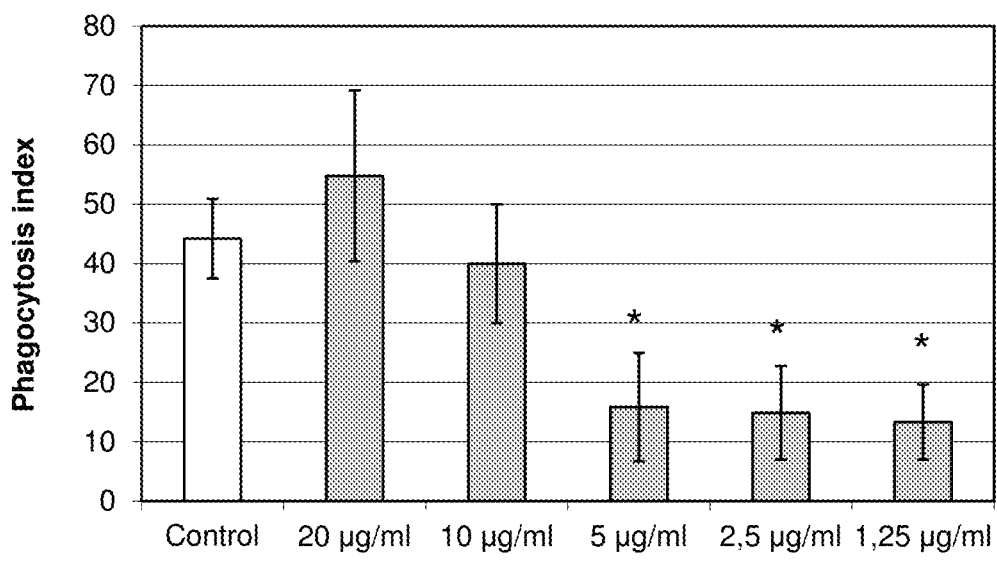
FIG. 40 shows the effects of $^{64}Zn_e$-asp on phagocytic activity of nonsensitized rat monocytes. Key: *—$p \leq 0.05$ versus untreated cells

At concentrations ≤5 µg/ml, the drug reduced phagocytic activity of monocytes (FIG. 40). It should be noted that there was a significant variability of the studied indicator, which might be caused by incomplete solubility of $^{64}Zn_e$-asp in isotonic saline or insufficient functional maturity of monocytes. To confirm these assumptions, a parallel study of the phagocytic function of cells and the expression of one or more endocytic receptors on the membrane of these cells is advisable.

Figure 41:
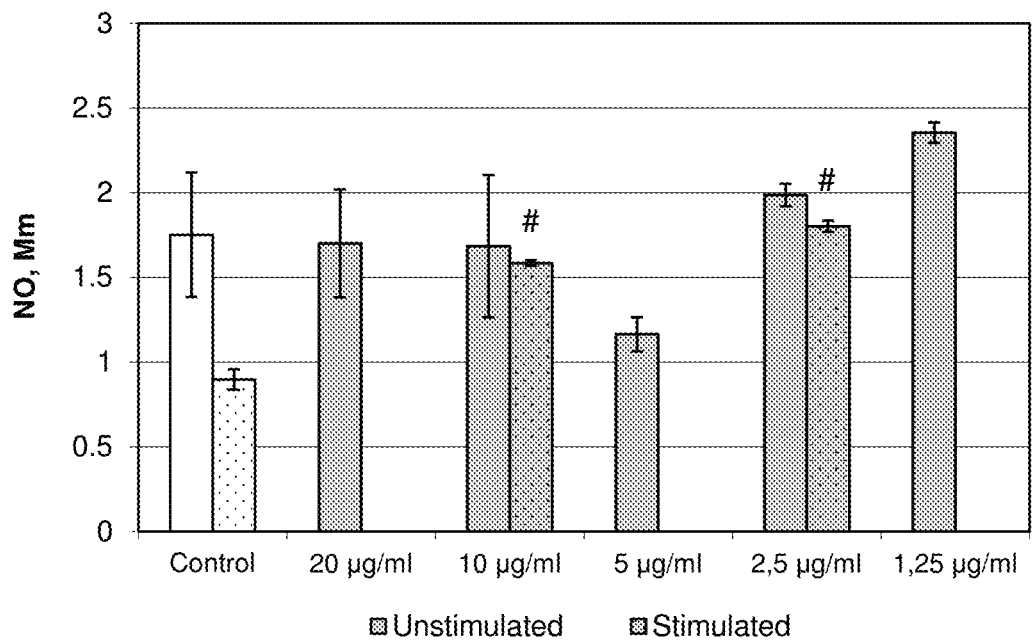
FIG. 41 shows the effects of $^{64}Zn_e$-asp on NO production by nonsensitized rat peripheral blood monocytes. Key: #—$p \leq 0.05$ versus bacterial lipopolysaccharide-stimulated cells.

Spontaneous production of nitrites by nonsensitized circulating monocytes did not change significantly after their treatment with the drug, regardless of the concentration used. However, the drug moderately increased the production of nitric oxide monocytes after they were treated with LPS (FIG. 41). A mechanism of this action is mediated by the effect of the drug on intracellular ROS production. It is known that the synthesis of reactive oxygen species has a negative effect on the synthesis of reactive nitrogen species by mononuclear phagocytes, especially in functionally immature cells, including monocytes. Therefore, a slight increase in the synthesis of nitric oxide may be due to the inhibitory effect of the drug on ROS production.

Figure 42:
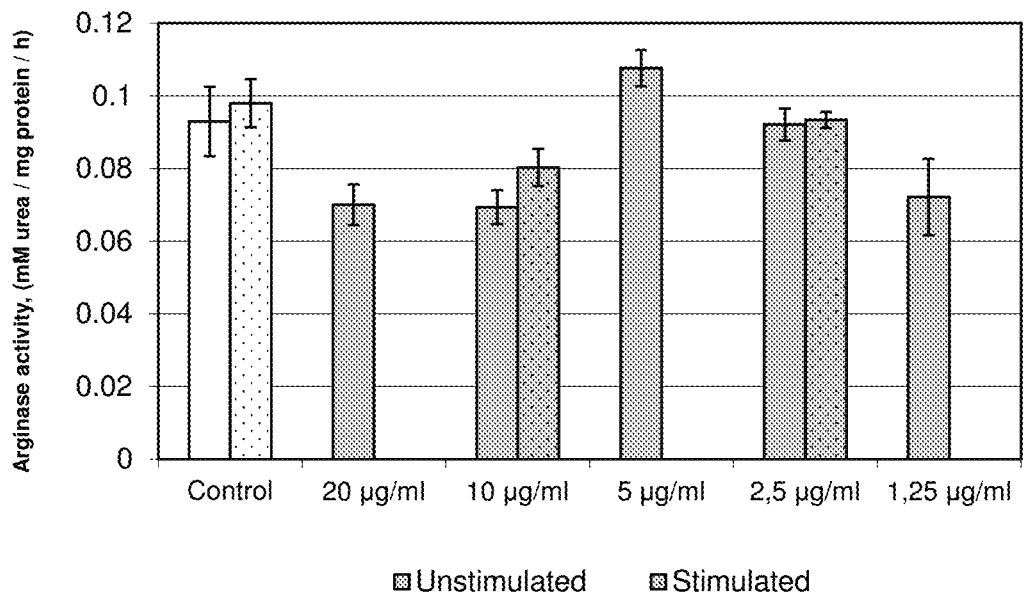
FIG. 42 shows the effects of $^{64}Zn_e$-asp on arginase activity of nonsensitized rat peripheral blood monocytes.

Statistically significant effects of $^{64}Zn_e$-asp on arginase activity of monocytes were absent both after treatment of resting cells and after addition of the drug against the background of bacterial LPS cell treatment (FIG. 42). The results of the study into arginase and NO synthase activity of monocytes indicate the absence of any significant effects of the drug on the arginine metabolic pathway in these cells. According to the degree of maturity and functional plasticity, phagocytes of microglia differ from circulating monocytes. Resident microglial cells are functionally mature tissue phagocytes originating from the yolk sac, capable of self-renewal and characterized in the literature as cells with very conservative metabolism. Circulating monocytes are functionally immature cells (except for the subpopulation of monocytes patrolling along the endothelial wall that are not separated by the method used in the study).

Many metabolic reactions (including signaling pathways) are in these cells in an inactive and/or semi-active state, which significantly increases the metabolic plasticity of monocytes.

Peripheral Blood Neutrophils

Figure 43:
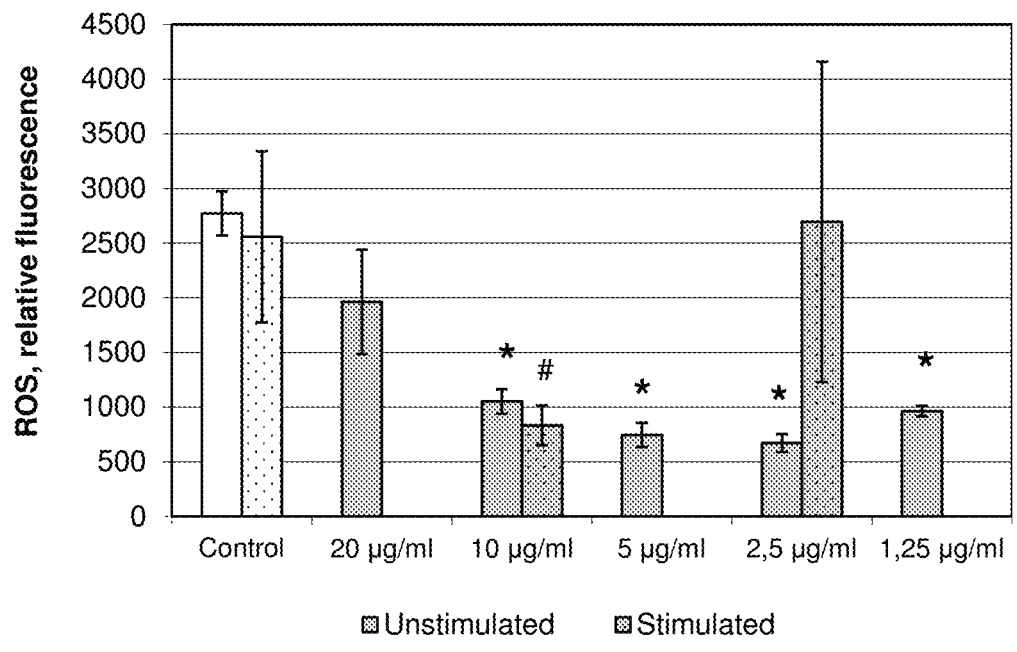
FIG. 43 shows the effects of $^{64}Zn_e$-asp on intracellular ROS production by nonsensitized rat peripheral blood neutrophils. Key: *—$p \leq 0.05$ versus untreated cells; #—$p \leq 0.05$ versus bacterial lipopolysaccharide-stimulated cells.

Treatment of circulating nonsensitized neutrophils with $^{64}Zn_e$-asp led to a sharp decrease in the intracellular ROS production by these cells (FIG. 43). The modulating effect had inversely proportional dose dependence. Adding the drug to cells against the background of their treatment with bacterial LPS also caused a sharp decrease in the esterase-dependent oxidative metabolism in neutrophils. It should be noted that neutrophils were the most sensitive cells to the antioxidant action of $^{64}Zn_e$-asp. Neutrophils differ from all previous phagocytes in their functional characteristics. Neutrophils are functionally mature cells with a very reactive metabolism, which causes a short duration of their life. These are exclusively circulating cells, which are the first and one of the main effectors of inflammatory reaction (both associated with infectious processes and aseptic inflammation). Metabolic plasticity of neutrophils is least studied.

Figure 44:
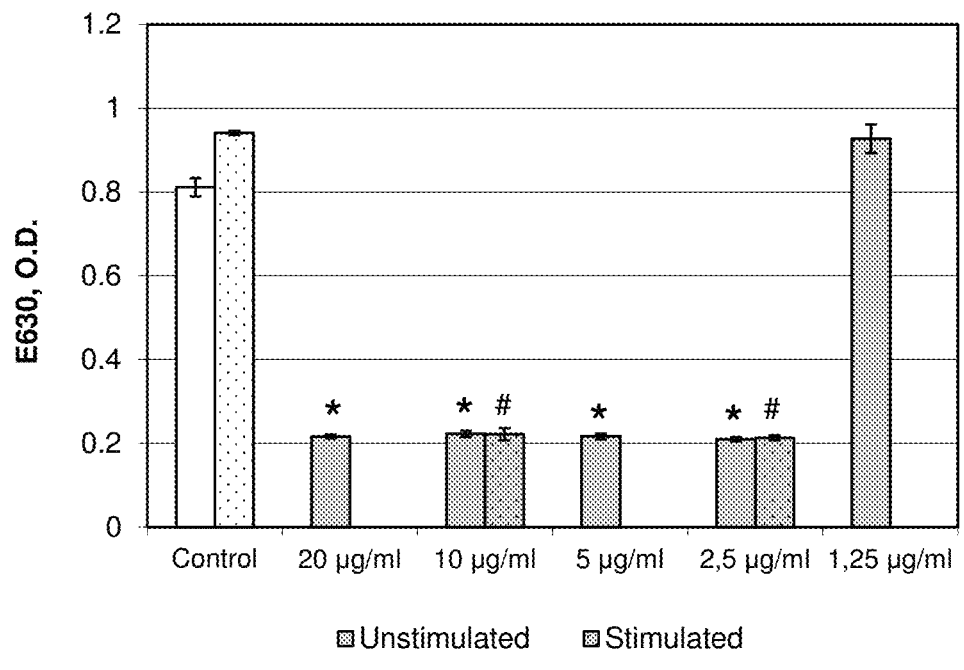
FIG. 44 shows the effects of $^{64}Zn_e$-asp on NBT test indices of nonsensitized rat peripheral blood neutrophils. Key: *—$p \leq 0.05$ versus untreated cells; #—$p \leq 0.05$ versus bacterial lipopolysaccharide-stimulated cells.

The drug also had a strong negative effect on the ROS production dependent on NADH and NADPH oxidases, irrespective of treatment of cells with bacterial LPS (FIG. 44).

However, there was no dose-response relationship in this case. Low variability of the studied indicator should also be noted.

Figure 45:
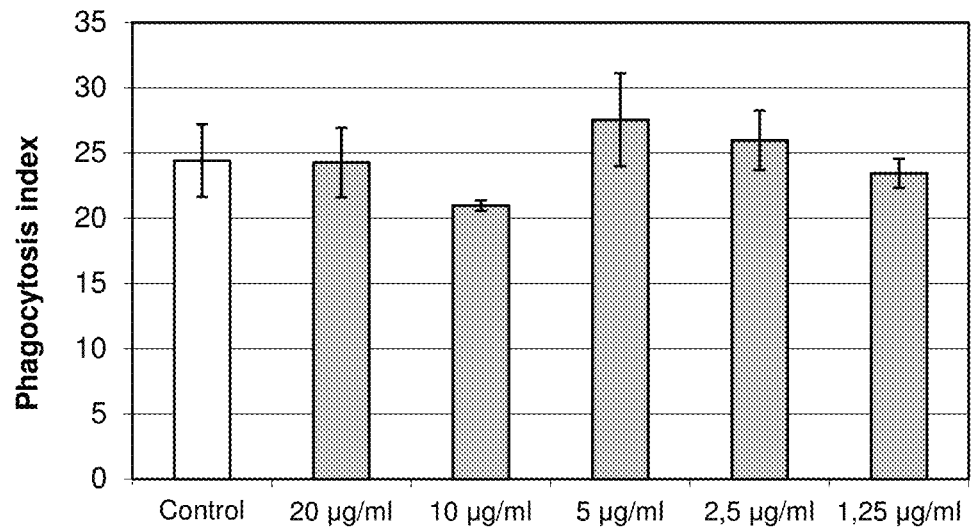
FIG. 45 shows the effects of $^{64}Zn_e$-asp on phagocytic activity of nonsensitized rat peripheral blood neutrophils.

No statistically significant effect of the drug on the phagocytic activity of neutrophils was observed (FIG. 45).

It should be noted that the indices of phagocytic activity of neutrophils were low. A specific feature of rat blood is a low number of its circulating neutrophils in comparison with other laboratory rodents. No literary data on specific features of the intensity of endocytosis by neutrophils in these animals have been found.

Figure 46:
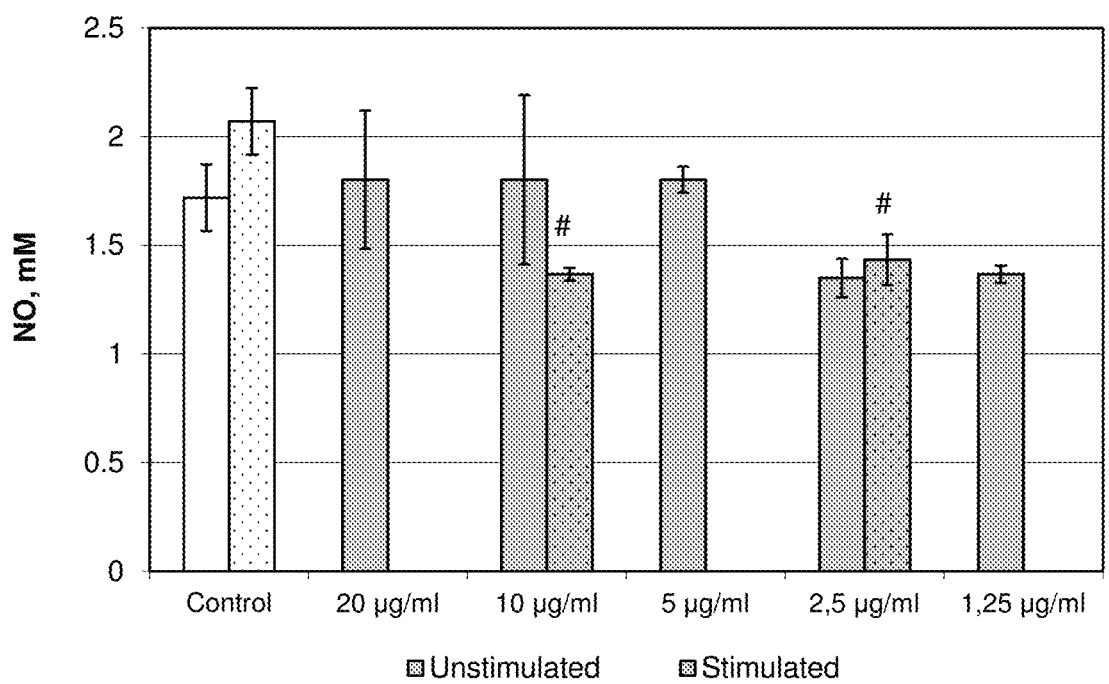
FIG. 46 shows the effects of $^{64}Zn_e$-asp on NO production by nonsensitized rat peripheral blood neutrophils. Key: #—$p \leq 0.05$ versus bacterial lipopolysaccharide-stimulated cells.

$^{64}Zn_e$-asp had no significant effect on the synthesis of reactive nitrogen species by resting neutrophils and produced a moderately negative effect on this metabolic reaction after treatment of cells with LPS (FIG. 46).

Figure 47:
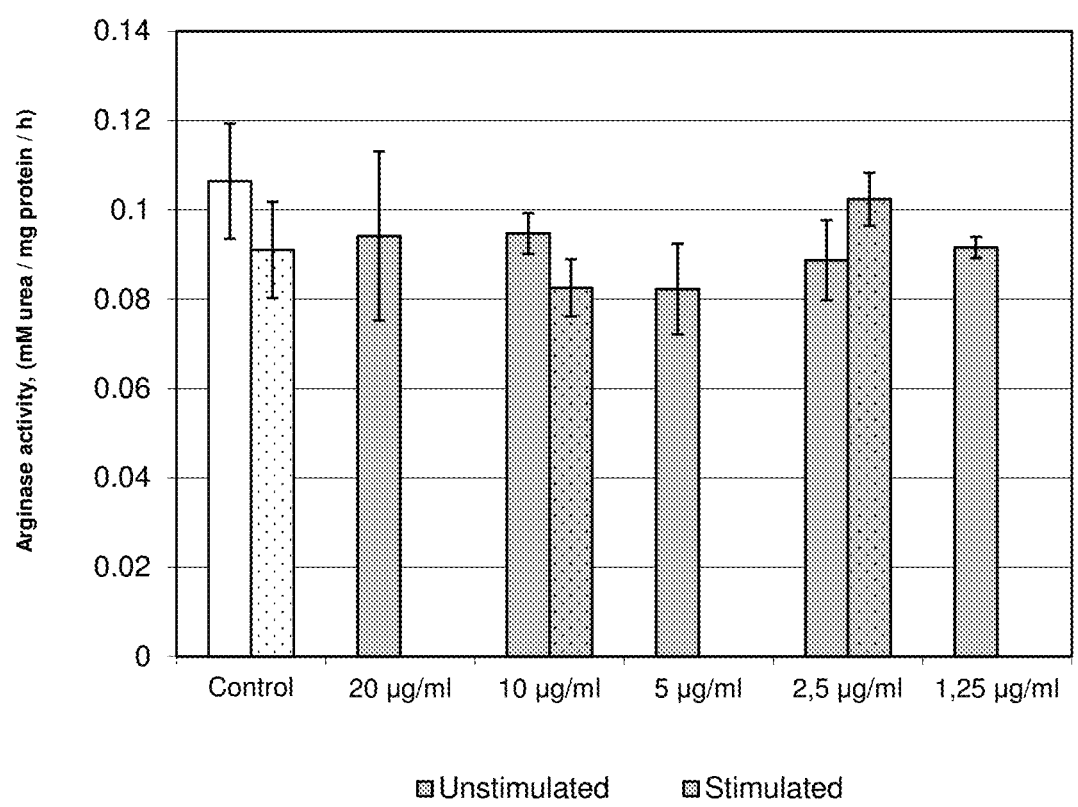
FIG. 47 shows the effects of $^{64}Zn_e$-asp on arginase activity of nonsensitized rat peripheral blood neutrophils.

Arginase activity of both resting and bacterial LPS-treated neutrophils remained practically unchanged under the action of the drug (FIG. 47).

FIG. 47 shows the effects of $^{64}Zn_e$-asp on arginase activity of nonsensitized rat peripheral blood neutrophils.

All these data put together indicate that the drug has only moderate effect on the pathway of arginine metabolism in circulating neutrophils.

Findings of Example 3:
1. Comparative analysis of the effects of $^{64}Zn_e$-asp on the metabolic profile of four populations of phagocytes revealed that the most sensitive to the action of the drug were microglial cells (treatment with the drug caused changes in almost all the functions studied). Peritoneal macrophages were the least sensitive.
2. Of all metabolic reactions studied, the drug has the greatest effect on the oxidative metabolism of cells of all the populations studied; it has no effect on arginase activity and virtually has no effect on endocytosis activity of cells.
3. The drug inhibits induced oxidative metabolism in the cells of all the studied populations of phagocytes and it inhibits induced production of reactive nitrogen species virtually in all cells, which indicates an anti-inflammatory character of its immunomodulatory effect. The greatest antioxidant effect was recorded in the case of neutrophils.

The response of microglial resident phagocytes to the drug is largely similar to that of tissue phagocytes of peripheral localization (peritoneal macrophages).

Example 4. Effects of $^{64}Zn_e$-Asp and E2+$^{85}Rb_e$ Preparations on Spontaneous and Phytohemagglutinin-Induced Proliferative Activity of Human Peripheral Blood Mononuclear Cells Introduction: It is known from the relevant literature that mitogen-stimulated T-lymphocytes activate the expression of transferrin receptors that promote zinc influx into the cell (Mathe G, et al., *Med Oncol Tumor Pharmacother.* 1985; 2(3):203-10; F Flynn A. *Nutrition Research.* 1985; 5(5):487-495.). Zinc-transferrin complexes stimulate synthesis of DNA in activated T-lymphocytes and virtually have no effect on this process in resting lymphocytes (Rosenkranz E, et al. *Eur J Nutr.* 2017 March; 56(2):557-567. doi: 10.1007/s00394-015-1100-1; Barnett J B, et al., *Am J Clin Nutr.* 2016 March; 103(3):942-51. doi: 10.3945/ajcn.115.115188). According to the published data, rubidium salts (chlorides) stimulate the processes of differentiation of lymphoid and myeloid lineages of blood cells in the bone marrow and, therefore, have a negative effect on their proliferation (Hammarstrom L, Smith C I. *Exp Cell Res.* 1979 Mar. 15; 119(2):343-8; Petrini M, et al., *Haematologica.* 1990 January-February; 75(1):27-31). There are no data on the effects of rubidium salts on the proliferative activity of differentiated T-lymphocytes in the literature.

Materials and Methods: Peripheral blood mononuclear cells were isolated from a healthy donor by density gradient centrifugation over Histopaque-1077 (Sigma, USA). Phytohemagglutinin (PHA) (Sigma, USA) was used to activate the proliferative activity of T-lymphocytes. The cells were exposed to the action of both preparations for 48 hours. A stimulatory (with the addition of the drugs as single components) and costimulatory (with the addition of the drugs in combination with PHA) effects were assessed. CD3 phenotypic marker was used to selectively measure proliferative activity of T-lymphocytes. The T-cell proliferative activity was assessed by analyzing the DNA status of CD3+ cells using a flow cytometry technique. The results are presented in the form of a proliferative index, calculated by the following formula:

$$PI=((S+G_2M)/(G_0G_1+G_2M))\times 100$$

(Peng X, et al., *Biol Trace Elem Res.* 2011 December; 144(1-3):688-94. doi: 10.1007/s12011-011-9077-y).

Figure 48:
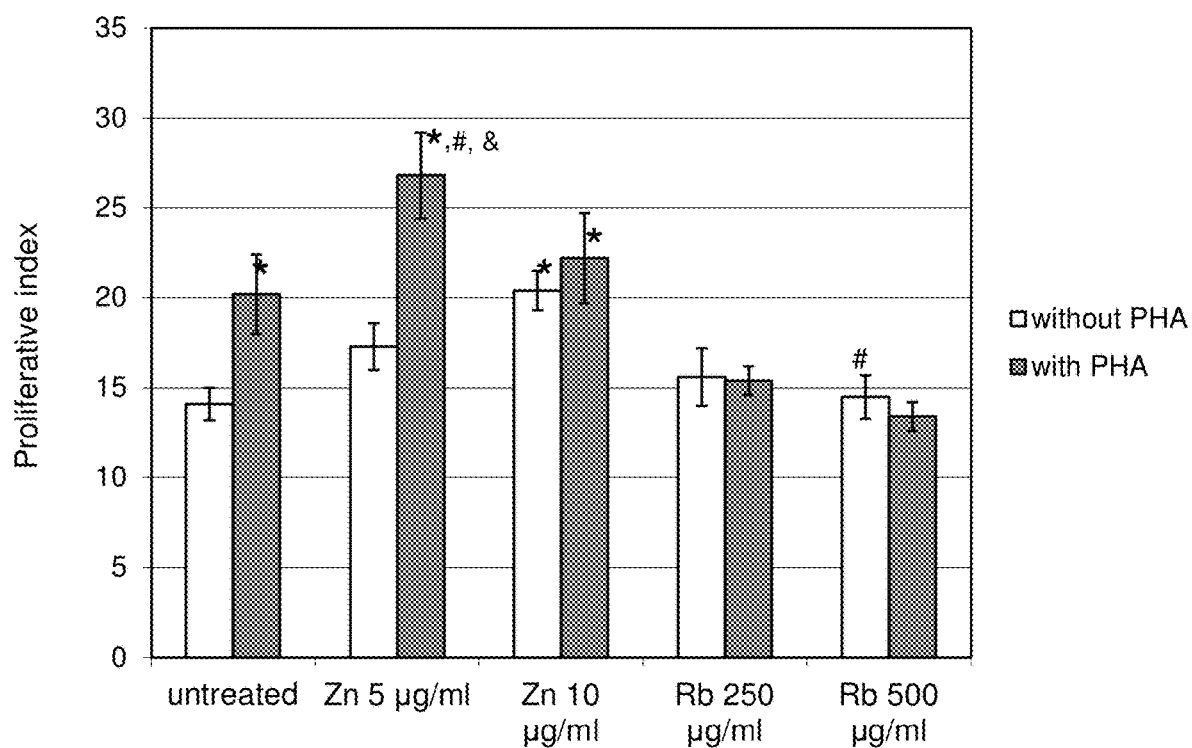
FIG. 48 shows in vitro effects of $^{64}Zn_e$-asp and E2+$^{85}$Rb$_e$ preparations on spontaneous and PHA-stimulated proliferative activity of human T-lymphocytes. Key: *—$p \leq 0.05$ versus untreated cells; #—$p \leq 0.05$ versus PHA-stimulated cells.

Results:

When used in vitro separately from PHA, $^{64}Zn_e$-asp had a dose-dependent weak stimulatory effect on CD3+ T-lymphocytes, in contrast to zinc chloride, which, according to the published data, has no effect on proliferation of unstimulated T-cells (FIG. 48).

When used in combination with PHA, a classical mitogen of T-lymphocytes, the preparations increased proliferative activity of cells as compared to the samples treated with the mitogen alone and untreated samples. No dose-response relationship was traced. The data obtained coincide with the published data on the costimulatory effects of zinc chloride on T-cell proliferation.

E2+$^{85}$Rb$_e$ did not produce any in vitro effect on the spontaneous proliferative activity of T-lymphocytes and significantly inhibited mitogen-induced proliferation of the cells. Consequently, the effects of the drug differ from that of rubidium chloride, which, according to the published data, has an inhibitory effect on the proliferation of both resting and activated lymphocytes.

Figure 49:
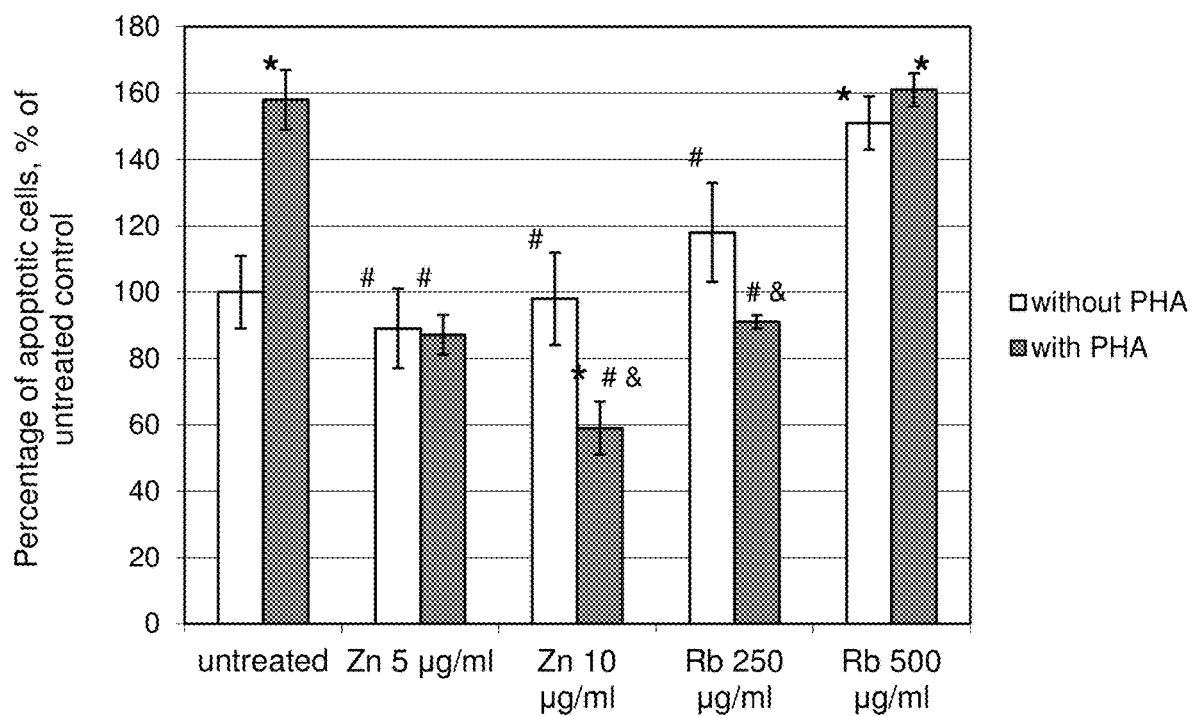
FIG. 49 shows in vitro effects of $^{64}Zn_e$-asp and E2+$^{85}$Rb$_e$ preparations on activation-induced apoptosis of human T-lymphocytes. Key: *—$p \leq 0.05$ versus untreated cells; #—$p \leq 0.05$ versus PHA-stimulated cells.

T-cell apoptosis (activation-induced apoptosis) (Brenner D, et al., *Crit Rev Oncol Hematol.* 2008 April; 66(1):52-64. doi: 10.1016/j.critrevonc.2008.01.002) is an additional criterion for T-cell activation. In this connection, the levels of activation-induced apoptosis of T-lymphocytes treated with the test drugs separately and in combination with PHA were measured. As can be seen from FIG. 49, $^{64}$Zn$_e$-asp used alone did not have any effect on the activation-induced T-cell apoptosis. But when this drug was used in combination with the mitogen (10 g/ml), the levels of activation-induced T-cell apoptosis significantly decreased, which indicates its ability to inhibit apoptosis of actively proliferating cells. It is necessary to pay attention to this effect when investigating the antitumor properties of the said drug.

E2+$^{85}$Rb$_e$ preparation at a concentration of 500 µg/ml had a pronounced pro-apoptotic effect when used both separately and in combination with the mitogen. This suggests that the drug has antineoplastic properties, at least in relation to malignant T-lymphocytes. In addition, a positive effect of the drug on inflammatory pathological processes accompanied by activation of T-cell proliferation (autoimmune diseases, allergic pathology) is possible.

Findings of Example 4:
1. $^{64}$Zn$_e$-asp has stimulatory and costimulatory effects on T-lymphocyte proliferation as well as inhibits apoptosis of actively proliferating T-cells.
2. E2+$^{85}$Rb$_e$ has no effect on spontaneous proliferative activity of T-lymphocytes; it inhibits mitogen-induced cell proliferation along with stimulation of apoptosis of actively proliferating T-cells.

Overall Conclusions

Thus, the results of the in vitro study into the effects of $^{64}$Zn$_e$-asp and E2+$^{85}$Rb$_e$ on the metabolic profile of phagocytes of different localization demonstrated the following. Microglial cells, circulating phagocytes (monocytes and neutrophils) as well as peritoneal macrophages are sensitive to both drugs. Microglial cells showed the greatest sensitivity to the zinc-based preparation. Phagocytic activity of microglia intensified under its action, which is a sign of its activation. $^{64}$Zn$_e$-asp enhanced ROS production by resting (unstimulated) microglial cells, which indicates the ability of the drug to activate a reparative activity of brain phagocytes. At the same time, ROS production by activated microglial cells (situation that simulated an inflammatory process) decreased under the action of the drug. The arginine metabolic pathway in microglial cells shifted towards enhancing arginase activity under the action of the drug, which once again confirms the anti-inflammatory nature of its immunomodulatory action (arginine metabolism via arginase leads to the formation of molecules which are precursor of extracellular matrix components necessary for reparative processes, whereas arginine metabolism via NO synthase leads to the formation of reactive nitrogen species—NO—with a cytotoxic function). The nature of changes in metabolism of circulating phagocytes under the action of $^{64}$Zn$_e$-asp differed from that of microglia. The drug caused a decrease in ROS production by both resting and stimulated monocytes and neutrophils and had a weak effect on phagocytosis and arginine metabolism in these cells. The response of peritoneal macrophages to $^{64}$Zn$_e$-asp was similar to that of microglial cells, which is completely logical given the fact that both cell populations represent resident tissue mature phagocytes of ontogenetic origin, in contrast to circulating phagocytes having a bone marrow origin. In other words, peritoneal phagocytes intensified ROS production under the action of $^{64}$Zn$_e$-asp and at the same time they sharply reduced the synthesis of reactive nitrogen species, which indicates an anti-inflammatory (reparative) shift in their metabolism.

Combined treatment of phagocytes of different localization with $^{64}$Zn$_e$-asp and E2+$^{85}$Rb$_e$ preparations caused slightly different changes in their metabolism. The phagocytic activity of microglia decreased with such treatment, the ROS synthesis both by resting and stimulated cells also decreased along with a decrease in production of reactive nitrogen species, which all together indicates an anti-inflammatory modulation of functions of these cells by a combination of the preparations comprising microelements. The nature of the effects of combined treatment of circulating phagocytes with $^{64}$Zn$_e$-asp and E2+$^{85}$Rb$_e$ did not differ in principle from that with the use of the zinc-based drug as monotherapy. The drugs reduced ROS production both by monocytes and neutrophils and, in addition, they reduced the production of reactive nitrogen species by circulating phagocytes, which indicates their anti-inflammatory effect.

Treatment of peritoneal macrophages with E2+$^{85}$Rb$_e$ led to a more pronounced anti-inflammatory shift in metabolism in these cells than their treatment with the zinc-based drug when used as monotherapy.

The results of these in vitro study suggest expediency of prophylactic anti-inflammatory modulation of phagocytic functions of different localization preceding the initiation of PD in in vivo studies. In our opinion, such advance preparation of phagocytes in the brain, peripheral blood and peritoneal cavity could inhibit their inflammatory activation which accompanies the development of the disease and weaken/reduce the degree of destruction of dopaminergic neurons in the black substance in animals.

This assumption was confirmed by the results on prophylactic administration of the drugs before inducing PD in rats. The zinc-based drug, used both as monotherapy and in combination with the preparation containing rubidium, caused a decrease in the degree of destruction of dopaminergic neurons in the animals during the development of PD. Such decrease in the degree of destruction of dopaminergic neurons was accompanied by positive changes in phagocytes of different localization in the animals that received the drugs under study as preventive medication, in contrast to the control animal models of PD characterized by pro-inflammatory activation of phagocytes of different localization which was largely leveled by prophylactic administration of the preparations comprising microelements.

Microglia in the control animal models of PD differed from those in intact animals by decreased ROS production and at the same time enhanced synthesis of reactive nitrogen species having a great destructive effect on neurons in the black substance. Prophylactic administration of the drugs was accompanied by increased ROS production by microglial cells simultaneously with a decrease in synthesis of reactive nitrogen species. As it was mentioned above, enhanced ROS synthesis is a necessary condition for the activation of reparative processes. Therefore, the enhancement of oxidative metabolism in microglial cells in combination with their anti-inflammatory polarization (increased scavenger receptor expression and reduced synthesis of reactive nitrogen forms) indicates the ability of the microelement-based preparations to activate reparative processes in the brain of animal models of PD subject to their systemic intraperitoneal administration. Circulating phagocytes in rat models of Parkinsonism were characterized by pronounced pro-inflammatory polarization, which confirms the literature data on the involvement of these cells in the systemic inflammation accompanying the development of PD. Prophylactic administration of the microelement-based preparations prevented inflammatory activation of these cells. The same is true for the changes in metabolism of peritoneal macrophages in rat models of PD after prophylactic administration of the microelement-based preparations.

The prophylactic effect of the drug comprising zinc was more pronounced, but less stable in time, whereas the effect of combined use of zinc- and rubidium-based drugs was less expressive, but stable over time.

Example 5 Reduced Toxicity of Disclosed Compounds

In vitro assessment of the effects of E2+$^{85}$Rb$_e$ on metabolic activity of normal human fibroblasts (MTT assay).

Concentration of compounds of E2 series E2+Rb reference drug E2+$^{85}$Rb$_e$

Metabolic Activity of Cells, %*

* in comparison with the control group—100% of living cells

150 µg/ml 99.3±3.2 72.8 2.1
75 µg/ml 97.7±7.5 67.4±4.7
38 µg/ml 98.8±7.1 68.5±1.8
20 µg/ml 96.8±9.8 74±1.3
10 µg/ml 104.6±14.2 82.5±1.3
5 µg/ml 103.4±9.3 82.3±3
2.5 µg/ml 128.2±8.3 84.4±4.6
1.25 µg/ml—105.1±2.3

Proliferative and metabolic activity of cells was determined by the colorimetric method.

The metabolic activity of the cells (i.e., the number of living cells) was assessed by MTT staining.

24 hours after the last reagent, the cells were seeded at a concentration of 1×104 cells/well in wells of a 96-well plate in complete DMEM nutrient medium with 10% FBS and g/ml gentamicin. The cells were cultured in a humidified atmosphere at 5% $CO_2$ and 37° C. for 24 hours. After 24 hours, various doses of experimental substances were added to the respective wells. The cells were incubated at 37° C. and 5% $CO_2$ for an additional 72 hours.

Upon completion of the incubation with the preparations, the proliferative and metabolic activity of the cells in the experiment was evaluated by the colorimetric method by staining MTT cells:

10 µl of the MTT solution (5 mg/ml of the dye in phosphate-buffered saline) was added to each well of the plate; the plate was incubated in a CO2 incubator at 37° C. for 3 hours. After that, the medium was removed from the wells, and the formed tetraformazan crystals were dissolved in 100 µl of dimethylsulfoxide.

When MTT was used, the results were evaluated using a multi-well spectrophotometer at an excitation wavelength of 540 nm. The percentage of viable cells was calculated by the formula:

$$IR=(A540 \text{ (experiment)}/A540 \text{ (control)})\times 100\%.$$

Example 6

Compound 7 was prepared as follows. The same procedure can be used to prepare the other compounds of Formula 1, with use of $^{85}$Rb$_e$Cl as appropriate and with starting materials and intermediates comprising the appropriate substituents to obtain the desired product. An alternative synthesis is provided below for when $R_9$ is $OCH_3$.

Phase 1

10.8 g of o-phenylenediamine base were dissolved in 100 ml of isopropyl alcohol and, while maintaining the mixture at room temperature, 200 ml of an alcohol solution of benzenesulfonyl chloride (17.65 g) were added. The resulting mixture was stirred up for 1 hour at room temperature and 0.5 hours at 65-70° C. After cooling, the resulting light-colored precipitate was filtered by thorough washing with cold water to remove the residue of unreacted o-phenylenediamine. The precipitate from the filter was boiled in 10% hydrochloric acid and filtered while hot to remove by-produced bis-dibenzenesulfonyl-o-phenylenediamine. The filtrate was clarified with activated carbon and, after cooling, N-benzenesulfonyl-o-phenylenediamine hydrochloride in the form of fine needle crystals was filtered off (weight per dry matter 7.11 g. Yield 25%).

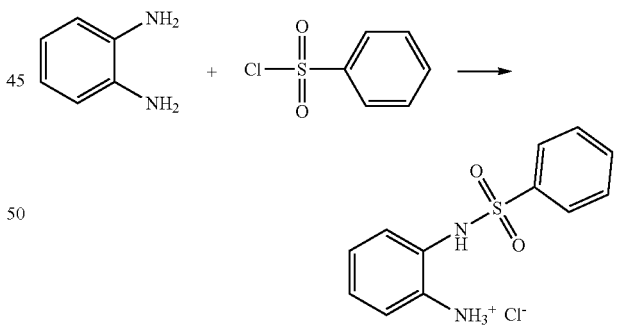

Phase 2

N-benzenesulfonyl-o-phenylenediamine hydrochloride obtained in the first phase (7.11 g) was suspended in 50 ml of toluene and 5.1 g of o-nitrobenzoyl chloride and 5.32 g (7.1 ml) of triethylamine were added. The reaction mixture was boiled under reflux in an oil bath for 3 hours and, after cooling, the precipitate formed was filtered off. The resulting substance was recrystallized from isopropyl alcohol and purified with activated carbon. The yield of dry N-benzenesulfonyl-N'-2-nitrobenzoyl-o-phenylenediamine was 6.45 g (65%).

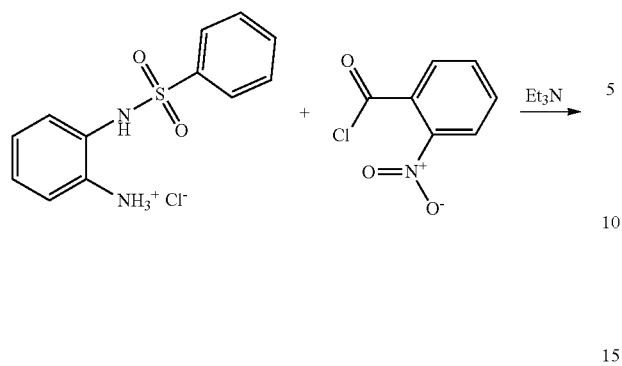 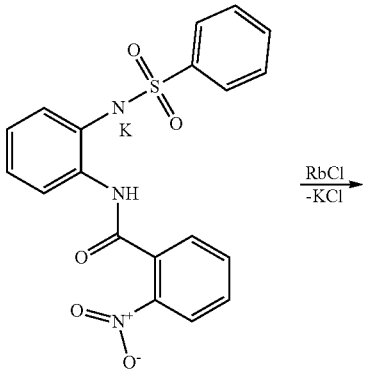

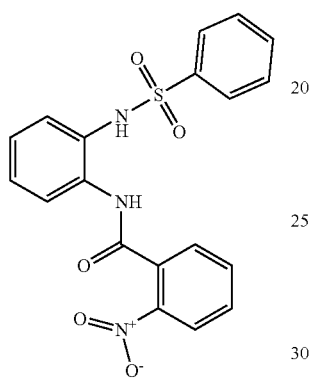

Phase 3

Preparation of aqueous solution of rubidium salt of N-benzenesulfonyl-N'-2-nitrobenzoyl-o-phenylenediamine with a concentration of 0.001 g/ml with $^{85}Rb_e$: 0.073 g of KOH and 0.467 g of N-benzenesulfonyl-N'-2-nitrobenzoyl-o-phenylenediamine were dissolved in 90 ml of deionized water. The solution was stirred up while heating to dissolve the precipitate completely. After being cooled to room temperature, the solution was filtered and 0.1417 g of $^{85}Rb_eCl$ ($^{85}Rb_e$ was 99% $^{85}Rb$) was added, which quickly dissolved. The reaction mixture was stirred up at room temperature for 30 minutes and filtered again. The filtrate was made up to 100 ml with deionized water and used for further studies.

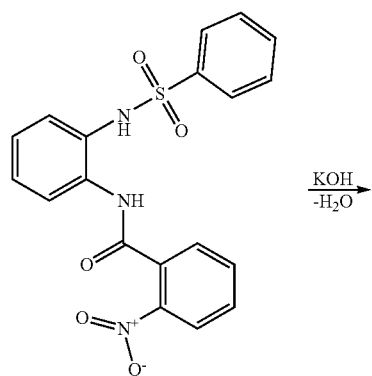

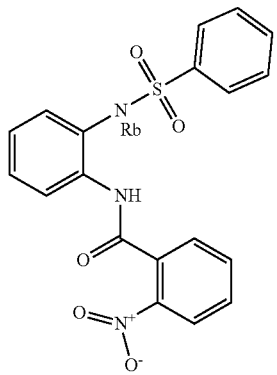

The following methods, among others, can be used to identify the newly synthesized compounds: measurement of the PMR spectra on a Varian VXR 200 spectrometer with respect to TMS in DMSO-$d_6$; measurement of IR spectra (4000-600 cm$^{-1}$) on a Bruker ALPHA FT-IR spectrometer using the ATR accessory; TLC on Silicagel 60 $F_{254}$ plates (eluent: chloroform); determination of mass spectra using a Kratos MS 890 mass spectrometer, with direct injection of the sample into the ion source at an ionization chamber temperature of 180-250° C. and ionizing electron energy of 70 eV.

When $R_9$ is $OCH_3$, the following alternative synthesis may be used. In the last step, $^{85}Rb_eCl$ can be used instead of RbCl in order to prepare an $^{85}Rb$-enriched product.

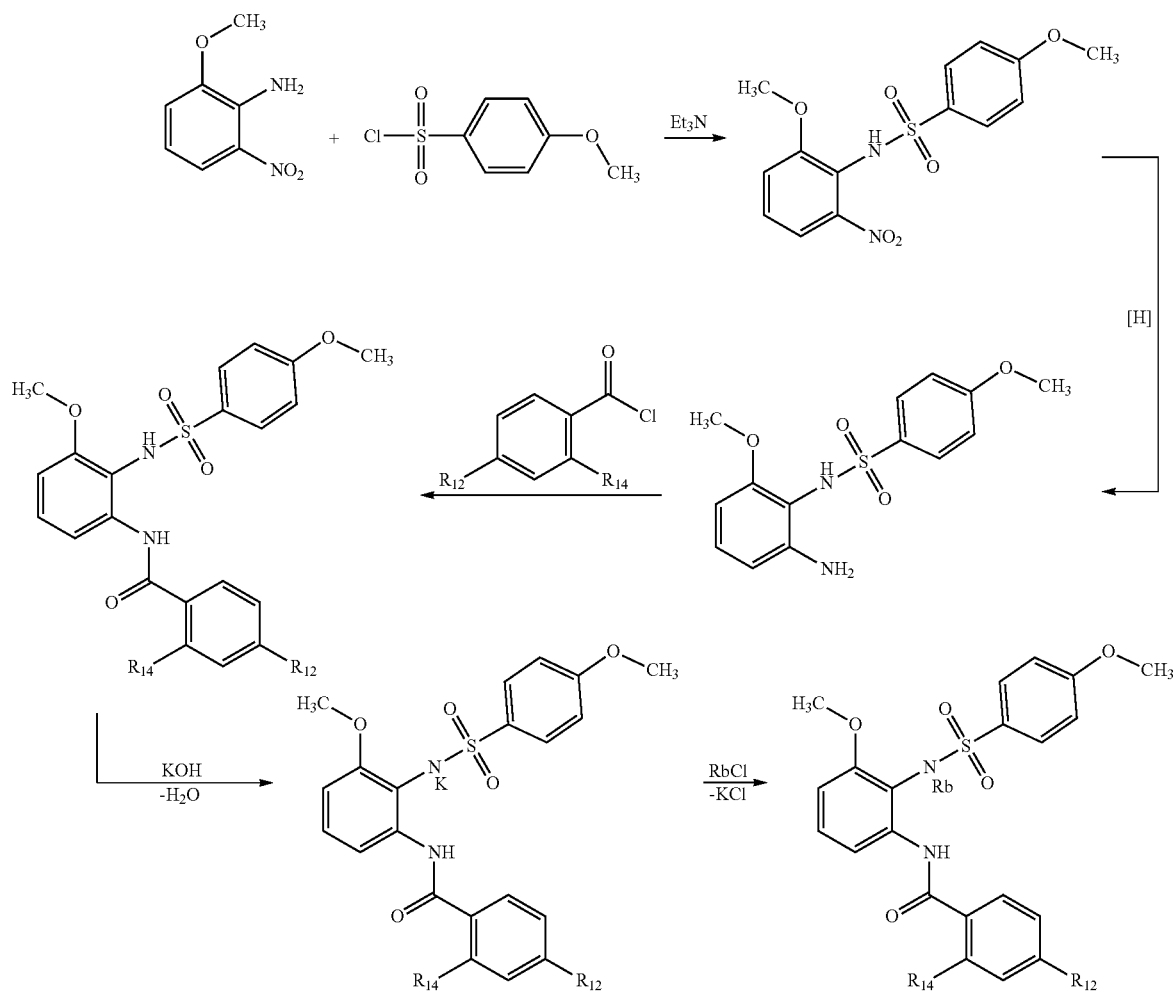

Example 7: Effects of $^{64}$Zn-Asp on Local and Systemic Immune Reactivity, Behavioural and Motor Functions in Rats with LPS-Induced Experimental Parkinsonism Zinc is recognized as an essential trace metal required for human health; its deficiency is strongly associated with neuronal and immune system defects. Zn also acts as a powerful modulator of the immune response.

Bacterial endotoxin (lipopolysaccharide, LPS) is a TLR4 agonist and a powerful pro-inflammatory activator of cells of innate immunity, including microglia that are resident mononuclear phagocytes of the brain. Subramanian Vignesh K, Deepe G S Jr. *Arch Biochem Biophys.* 2016; 611:66-78. doi: 10.1016/j.abb.2016.02.020; Liu M, fling G. *Parkinsons Dis.* 2011; 2011:327089. doi: 10.4061/2011/327089.

TLR4 is expressed by all cells of innate and adaptive immunity, as well as adipocytes, epithelial cells, and many other cells. Interaction of TLR4 and LPS activates NFκB-dependent signaling pathways, resulting in, first of all, activation of synthesis of pro-inflammatory mediators, including cytokines, chemokines, eicosanoids, etc. Hersoug L G, et al. *Obes Rev.* 2016; 17(4):297-312. doi: 10.1111/obr.12370; Vergadi E, et al. *Front Immunol.* 2018; 9:2705. doi: 10.3389/fimmu.2018.02705. An increased number of circulating LPS molecules is considered one of the most important factors in the activation of neurodegenerative processes and an essential component of the etiology of Parkinson's disease (PD), Alzheimer's disease (AD), etc. Sfera A, et al., Front Neurol. 2018; 9:1062. doi: 10.3389/fneur.2018.01062; Perez-Pardo P, et al., Gut. 2018. pii: gutjnl-2018-316844. doi: 10.1136/gutjnl-2018-316844.

Based on the above, LPS models of PD are of particular interest in the study of α-synucleinopathies, since they allow assessment of an inflammatory component in the development of the disease, as well as the most adequate assessment of the therapeutic efficacy of anti-inflammatory drugs proposed for treatment of this pathological condition.

Conditions for generation of LPS-induced models of experimental parkinsonism were optimized: out of two stereotaxic coordinates for the injection of endotoxin described in the literature, coordinates that ensured maximum neuroinflammation followed by a high degree of damage to the neurons of the substantia nigra were chosen.

Materials and Methods

Experimental Animals

Male Wistar rats (220-250 g) were used. The animals were maintained under standard conditions in the vivarium with unrestricted access to food and water.

Modelling Hemi-Parkinsonism in Rats

Chronic dopamine deficiency of the left hemisphere was modeled by unilateral destruction of dopaminergic neurons in the substantia nigra pars compacta portion of the brain. It was induced by stereotactic microinjections of 10 μg endotoxin (lipopolysaccharide) (Lipopolysaccharides from *Escherichia coli* O111:B4, cat. L2630 Sigma) dissolved in 2 μl sterile 0.9% NaCl (Infuzia CJSC, Ukraine). The solution was prepared on the day of a surgical procedure. A flask containing the resulting solution was sealed with a drop of silicone oil (STEP-ELECTRONICA LLC, Ukraine) and placed in a refrigerator.

An animal, anesthetized using a mixture of ketamine (75 mg/kg, diluted in sterile water for injection, Sigma, USA) and 2% xylazine (100 l/rat, Alfasan International B.V., Netherlands) administered intraperitoneally in a total volume of 1 ml, was placed in a stereotaxic apparatus (SEZH-4) modified for rats. The animal was then scalped and a trephine opening was made with an injection needle, directly into the substantia nigra (AP=−5.3; ML=+2.0; DV=−7.2). Dissolved LPS was collected into a home-made microinjector and its tip was dropped into the trephine opening.

Endotoxin at a dose of 10 μg in a volume of 2 μl was injected in the brain tissue at a rate of 1 μl/min (every 15 seconds). After endotoxin was administered, the tip of the microinjector remained in the brain tissue for 5 minutes. The microinjector was then removed and stitches were put on the scalp soft tissues of the animal. Control animals were administered 2 μl sterile 0.9% NaCl, instead of LPS (sham operated animals).

Apomorphine Test

The percentage of destroyed dopaminergic neurons was calculated using an apomorphine test. The intensity of rotational motions of an animal to the contralateral side of the hemisphere into which endotoxin was injected was assessed. A similar motor activity was induced by systemic intraperitoneal administration of apomorphine, a dopamine receptor agonist (0.5 mg/kg, Sigma, USA). The intensity of such rotational motions for 30 minutes indicated the degree of degradation of the nigrostriatal dopamine system (S A Talanov et al., *Neurophysiology* 38 (2), 128-133). The number of animals in which the number of rotations increased, decreased or remained unchanged within 30 minutes between apomorphine test I and II was quantified.

Immunohistochemical Identification of Dopamine Neurons

LPS-induced degeneration was evaluated using immunohistochemical tyrosine hydroxylase (TH) antibody staining [Walsh, S., Finn, D. P., Dowd, E., 2011. *Neuroscience* 175, 251-261]. Immunohistochemical staining of 5 μm paraffin-embedded midbrain sections was carried out using primary TH antibodies in 1: 200 dilution (Millipore, AB152). Endogenous peroxidase activity was quenched using a solution blocking endogenous peroxidase (Dako, EnVision Flex, DM821). Non-specific binding of antibodies was blocked with a 4% solution of dry milk in Tris-buffered saline (TBS) containing 0.2% Triton X-100.

The primary antibody was diluted in TBS containing 0.2% Triton X-100, applied on sections and incubated overnight (+4° C.). Secondary antibodies (biotinized anti-rabbit, 1: 200) were incubated for 60 min. The immunoreaction was developed diaminobenzidine (Dako, EnVision) applied for 5 min. Evaluation of TH staining was done at the light-optical level using a Primo Star microscope, Zeizz. The intensity of a peroxidase mark (in the area with maximum expression) was evaluated. Expression of receptors was evaluated using a scoring system.

Staining intensity was scored from 0 to 3, where:
0—no stain;
1—weak staining;
2—moderate staining;
3—strong staining intensity.

Measuring Water Content of Feces

Feces were collected on the $8^{th}$, $21^{st}$ and $28^{th}$ days of the experiment. They were weighed (wet weight $m_{ww}$) and dried in a thermostat at t=60° C. for 24 hours and then weighed again (dry weight $m_{dw}$). The water content of feces (M) was calculated as the percentage difference between wet and dry weight of feces according to the following formula: $M=100-(m_{dw} \times 100\%/m_{ww})$.

Behavioral Tests

Open Field Test

Method. The open field test is a technique commonly used to measure locomotor activity of rodents and their level of exploratory activity in an unfamiliar environment, as well as assess the levels of fear of novelty, anxiety or an increase in orientation response in rodents (Denenberg V H, et al., Physiology and Behavior, 1969; 4:403-406.; Pellow S et al., J Neurosci Methods. 1985; 14(3):149-67). Behavioral patterns measured in the open field test include: distance travelled in the outer and inner perimeter, duration of time spent in the outer and inner perimeter, the total distance travelled and a percentage of the number of internal squares crossed compared to the total number of squares.

The open field was a square chamber 100×100 cm in size and with walls 60 cm high. The chamber was illuminated by two LED bulbs, 60 watts each, hanging at a height of 2 m. An IP camera was used to record the rodent movement. The MATLAB-based software was used to analyze the parameters. The statistical analysis was performed using GraphPad Prism. Significance was set at <0.005. The data collected from the open field were analyzed using One-way ANOVA (Tukey test or Dunnett test) and Unpaired t-test or Mann-Whitney.

Figures 50A, 50B:
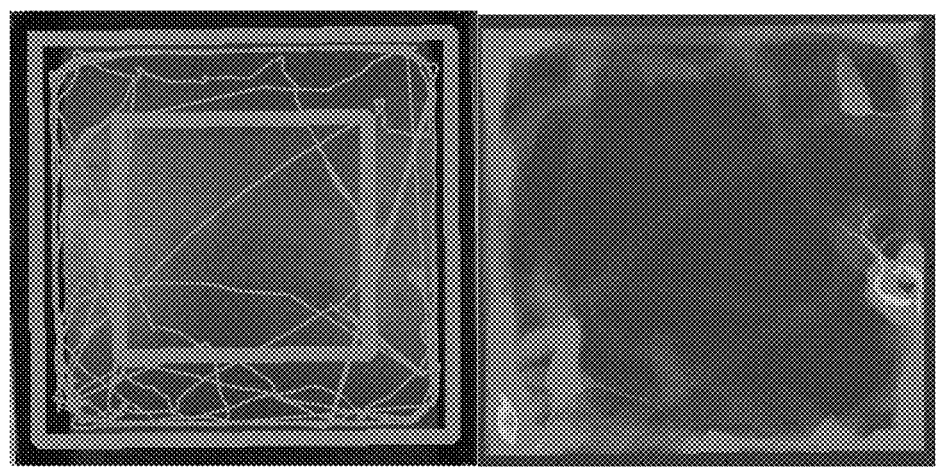
FIG. 50A displays a trajectory map and FIG. 50B displays a map of cumulative time spent by an animal in a given location in the open field for 5 minutes.

Data analysis and interpretation. A novel environment in which an animal finds itself evokes conflict between fear and a desire to explore this environment. These two behavioral tendencies are characterized by different temporal variations and different spatial advantages. In the analysis, an arena is divided into two zones: inner and outer. The total locomotor activity and time spent in the inner and outer zones are the most significant parameters for assessing the levels of anxiety in rats. It is considered normal if during a 5-minute test, animals spend most of their time near the walls, in the outer perimeter, and almost do not go out into the inner "open" zone. An increase in attendance of the inner zone is interpreted as a decreased anxiety in the animal. The emotional and exploratory behavior of an animal can be affected by various disorders in such brain regions as the hippocampus and the amygdala. In addition, various substances that have anxiolytic, stimulating and muscle relaxant effects can influence the results of the experiment. FIG. 50A and FIG. 50B show an example of analysis of a rat trajectory in the experimental arena.

Elevated Plus Maze

Method. The elevated plus maze is a widely used behavioral assay for rodents that makes it possible to assess sedative or anxiogenic effects of agents and to define mechanisms underlying anxiety-related behavior, as well as to evaluate the motor activity of rats and levels of their exploratory activity that may correlate with the data collected in the open field test. Campos A C, et al., *Braz J Psychiatry*. 2013; 35 Suppl 2:S101-11. doi: 10.1590/1516-4446-2013-1139; Braun A A, et al., *Neurobiol Learn Mem*. 2012; 97(4):402-8. doi: 10.1016/j.nlm.2012.03.004). Behavior was assessed according to the following main parameters: the total distance travelled, the number of entries into each arm, the time spent in each arm, the total number of entries and percent of entries. Each animal was placed at the junction of the four arms of the maze and the above parameters were observed for five minutes. Throughout the experiment, animals had free access to food and water. Before starting measurements, animals were given time to adapt to new an environment to reduce stress.

An apparatus used in the elevated plus maze had a cross-shaped structure that comprised two open arms (50×10 cm) across from each other and perpendicular to two closed arms (50×10×30 cm). The entire apparatus was elevated 50 cm above the floor. The central part of the junction was a 10 cm square center region where an animal was started facing an open arm. The apparatus was illuminated by two LED bulbs, 60 watts each, hanging at a height of 2 m. An IP camera was used to record the location of rats and scoring was completed later using the MATLAB-based software. The statistical analysis was performed using GraphPad Prism. Significance was set at <0.005. The data collected from the open field were analyzed using One-way ANOVA (Tukey test or Dunnett test) and Unpaired t-test or Mann-Whitney.

Data analysis and interpretation. The test is based on the natural aversion of rats for open areas and their preference for closed areas of the apparatus. The levels of anxiety in animals are assessed as the total time spent in the open and closed arms. Animals that spend more time in the open arms have lower levels of anxiety compared to animals that prefer closed arms. In addition, like in an open field test, a novel environment in which an animal finds itself evokes conflict between fear and a desire to explore this environment. Therefore, the data collected from these two tests may correlate in the distance travelled and the time spent in the outer and inner perimeter. It is considered normal if during a 5-minute test, animals spend most of their time in the closed arms but also make a few entries to the open arms to explore. Accordingly, an increase in open arm entries is interpreted as a decreased anxiety in the animal. FIG. 51A and FIG. 51B show an example of analysis of a rat trajectory in the experimental arena.

Pick-Up Test

The pick-up test is a test for increased irritability. The animal is picked up by grasping around the body. Responses were scored as 1, very easy; 2, easy with vocalizations; 3, some difficulty, the rat rears and faces the hand; 4, the rat freezes (with or without vocalization); 5, difficult, the rat avoids the hand by moving away; and 6, very difficult, the rat behaves defensively, and may attack the hand. (Brandt C et al., Neuropharmacology. 2006 September; 51(4):789-804).

Scheme of the Experiment

Animals were allocated into 7 groups: I (n=12)—intact animals that were maintained under standard vivarium conditions and did not receive any manipulations; II (n=12)—rats that were daily administered 0.1 ml of deuterium-depleted water intravenously (i.v.) for 10 days after the operation, the rats were sham operated; III—(n=12)—rats that were daily administered a solution of $^{64}$Zn-asp (1.5 mg/kg, i.v., for 10 days) after the operation, the rats were sham operated; IV (n=15)—rats that were daily administered 0.1 ml of deuterium-depleted water (i.v., for 10 days) after the operation, after which LPS-induced parkinsonian models were produced; V (n=15)—rats that were daily administered a solution of $^{64}$Zn-asp (1.5 mg/kg, i.v., for 10 days) after the operation, after which LPS-induced parkinsonian models were produced; VI (n=15)—rats that were daily administered a solution of $^{64}$Zn-asp+10% E2+$^{85}$Rb (1.5 mg/kg, i.v., for 10 days) after the operation, the rats were sham operated; VII (n=15)—rats that were daily administered a solution of $^{64}$Zn-asp+10% E2+$^{85}$Rb (1.5 mg/kg, i.v., for 10 days) after the operation, after which LPS-induced parkinsonian models were produced (FIG. 52).

1. On the $1^{st}$ day of the experiment, rats were either operated to model hemi-parkinsonism or sham operated. From the $9^{th}$ to the $18^{th}$ day of the experiment, the animals were injected either deuterium-depleted water or the test substance, according to their allocation into groups, for 10 days. On the $8^{th}$ day of the experiment (before initiation of treatment—apomorphine test I) and on the $21^{st}$ day of the experiment (after the end of administering the test substance—apomorphine test II) the animals underwent an apomorphine test to analyze the development of hemi-parkinsonism which correlates with the number of destroyed dopaminergic neurons. In addition, a follow-up analysis of fecal water content was carried out, i.e., before the start of treatment on the $8^{th}$ day after the operation, as well as on the $21^{st}$ (after the end of treatment) and the $28^{th}$ day (before autopsy). On the $24^{th}$ day of the experiment, behavioral tests were carried out in all groups. All animals were weighed before autopsy. During autopsy, ⅔ of animals from each group were sacrificed by cervical dislocation and brain and blood samples were collected for further biochemical and immunological tests. ⅓ of the animals were used for further immunohistochemical studies of the brain; for this purpose, under anesthesia, a procedure of fast, controlled and uniform fixation of the whole body of the animal was performed using 4% paraformaldehyde perfused through the heart of the rat to obtain the best preservation of the brain architecture for immunohistochemistry. Gage G J, et al., J Vis Exp. 2012 Jul. 30; (65).

Hematologic Assessment

The blood count values were analyzed at the completion of the experiment (day 28). The absolute number of leukocytes, as well as the absolute and relative numbers of lymphocytes, monocytes and neutrophilic granulocytes were calculated.

Isolation of Phagocytes of Various Localization

To assess the anti-inflammatory and immunomodulating effects of the test substance, microglia and peritoneal macrophages were isolated. Phenotypic and functional features of peripheral blood phagocytes were evaluated without their fractioning (using whole blood). To isolate microglia, brain tissue homogenate was obtained by manual homogenization followed by removal of undissociated conglomerates using cell strainers (No 70). Microglia cells were isolated from the obtained homogenate by centrifugation in a two-step Percoll gradient. Peritoneal macrophages were isolated without prior sensitization by perfusing ice-cold growth medium into the peritoneal cavity of a rat. An adhesive fraction of peritoneal exudate cells was used in the experiments.

Assessment of Phagocytic Activity of Phagocytes of Various Localization

Phagocytic activity of microglia, peritoneal macrophages and peripheral blood phagocytes was analyzed on a flow cytometer using FITC-labeled S. aureus Wood 46 cells as an object of phagocytosis. The S. aureus cells were obtained from the collection of microorganisms of the Department of Microbiology and Immunology of the ERC Institute of Biology and Medicine of the National Taras Shevchenko University.

Oxidative Metabolism of Phagocytes of Various Localization

Oxidative metabolism of phagocytes of various localization was analyzed by flow cytometry using the cell-permeant 2'7'-dichlorodihydrofluorescein-diacetate (DHP) (carboxy-H$_2$DCFDA, Invitrogen, USA) which is converted by intracellular esterases to the nonfluorescent membrane-impermeable carboxy-H$_2$DCF form.

Assessment of Phenotypic Profile of Phagocytes of Various Localization

The phenotypic profile of phagocytes of various localization was characterized by the expression of markers of functional maturity and metabolic polarization (CD206, CD80 and CD86), which was determined by flow cytometry and the use of monoclonal antibodies of appropriate specificity marked with fluorescent dyes (Abcam, Becton Dickinson).

Statistical Data Analysis Methods

The numerical results, except data collected from behavioral tests, were processed using statistical data analysis methods using Statistica 8.0 software package. To determine statistical significance of the reliable difference between the results shown by each group, the Student's t-test was used. Significance was set ta p≤0.05.

Statistical data processing of behavioral tests was performed using the GraphPad Prism 7 statistical software package. Non-parametric tests were used for static data processing. The median value for each group is shown by a horizontal line. The Kruskel-Wallis single-factor test and the post-hoc Dunn's test were used to determine significant differences between the groups. Significance was set ta p≤0.05.

Results

Therapeutic Effects of $^{64}$Zn-Asp on Apomorphine-Induced Rotational Behavior in Rat Models of Parkinson's Disease In a preliminary study, LPS animal models of Parkinson's disease was observed to have significantly less pronounced rotational behavior in comparison with the 6OHDA-induced PD models, which fact was confirmed in this study on a greater number of animals (groups IV, V, VII). In this Example, 38 rats (86%) out of 44 LPS models of Parkinson's disease (1 rat did not emerge from anesthesia) made fewer than 100 rotations per 30 min.

A physiological decrease in the number of rotational movements between the $1^{st}$ and $2^{nd}$ apomorphine tests was observed in 33.3% of rats (5 animals out of 15) of the control group (group IV) which had LPS-induced parkinsonism and were injected H$_2$O, while an increase in the number of rotations was observed in 66.6% of rats (10 animals out of 15) of this group, however the average number of rotations did not differ significantly between the $_1$St (35.3±25.5 rot./30 min) and $2^{nd}$ (43.4±36.1 rot./30 min) apomorphine tests (FIG. 53A and FIG. 53B).

Effects of $^{64}$Zn-Asp

Considering the fact that administration of $^{64}$Zn-asp was started the following day after the $1^{st}$ apomorphine test and the $2^{nd}$ apomorphine test was performed on the $3^{rd}$ day after the last injection of the test substance, the number of animals that in the $2^{nd}$ apomorphine test produced a smaller number of rotations than in the $1^{st}$ apomorphine test is a relevant marker of the test substance efficacy in preventing the destruction of dopaminergic neurons. There was no significant difference in the mean number of rotations between the $1^{st}$ (91.2±107.7 rot./30 min) and $2^{nd}$ (86.7±106.3 rot./min) apomorphine tests (FIG. 53A). However, in contrast to rats injected with deuterium-depleted water, 85.7% of rats treated with $^{64}$Zn-asp (12 out of 14 animals) made a fewer number of rotations between the $1^{st}$ and $2^{nd}$ apomorphine tests between the $1^{st}$ and $2^{nd}$ apomorphine tests and 14.3% of rats (2 out of 14 animals) increased the number of rotations (FIG. 53B), which indicates a significant efficacy of $^{64}$Zn-asp in preventing the intensity of the process of degeneration of dopaminergic neurons in the black substance of the left hemisphere.

Therapeutic Effects of $^{64}$Zn-Asp on the Number of TH-Positive Neurons in the Midbrain in Rat Models of Parkinson's Disease To further confirm positive therapeutic effects of the test substance in preventing degeneration of dopamine neurons, we conducted an immunohistochemical study of the number of TH-positive neurons in the midbrain. Tyrosine hydroxylase (TH) is an enzyme that limits the synthesis of dopamine and is a classic marker of dopamine neurons. The result of the study showed that the color of the substantia nigra of animals from the intact group (group I) and the sham-operated group (group II) was pronounced and corresponded to score 3. At the same time, administration of LPS to produce PD models led to a significant decrease in the number of TH-positive neurons (score 1) in the midbrain compared with the intact group and the sham-operated group (FIG. 54A-FIG. 54O, Table 2).

Figure 55:
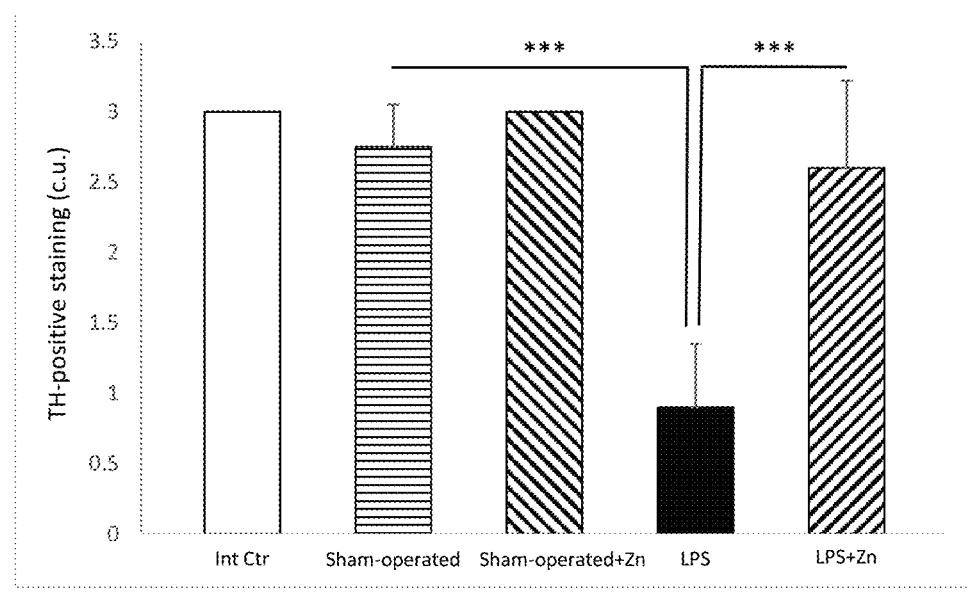
FIG. 55 is a graph of the therapeutic effect of $^{64}$Zn-asp on the number of TH-positive neurons in the midbrain in experimental parkinsonism. M±SD, P<0.001.

Administration of $^{64}$Zn-asp to sham operated animals did not cause any changes in the intensity of TH-positive staining in comparison with intact animals and sham-operated animals injected with water. At the same time, LPS rat models treated with $^{64}$Zn-asp (group VI) showed an increase in the number of TH-positive neurons in the midbrain compared to LPS animal models which were administered water (group V) (FIG. 54A-FIG. 54O, FIG. 55). These data correlate with the apomorphine test data (FIG. 53A and FIG. 53B) and confirm significant effectiveness of $^{64}$Zn-asp in preventing the intensity of degeneration of dopamine neurons in the black substance of the left hemisphere.

Therapeutic Effects of $^{64}$Zn-Asp on Body Weight Changes in LPS Rat Models of Parkinsonism Body weight of an animal is a classic clinical indicator that allows evaluation of its physiological status. A wealth of studies report weight loss may precede the diagnosis of Parkinson's disease by years and is also associated with the disease severity and duration [26]. In addition, PD-related motor and no-motor symptoms may influence the patient's body mass index. Weight loss is not an independent pathological factor but is associated with the pathogenesis of Parkinson's disease, as well as of Alzheimer's disease [Joly-Amado A et al., (2016). *Neurobiol. Aging* 44, 62-73]. In Alzheimer's disease, weight loss is one of the criteria for the clinical diagnosis of dementia. Similarly, in the context of Parkinson's disease, weight loss may precede motor symptoms and be considered as an indicator of the development of the disease. Kai Ma, et al., *Current Knowledge and Future Prospects Front Aging Neurosci.* 2018; 10: 1.

In these experiments, intact animals gained about 39% of the body mass in the period between the $1^{st}$ and $28^{th}$ days of the experiment (within 4 weeks). Sham operated rats also gained weight by an average of 30%.

Figure 57:
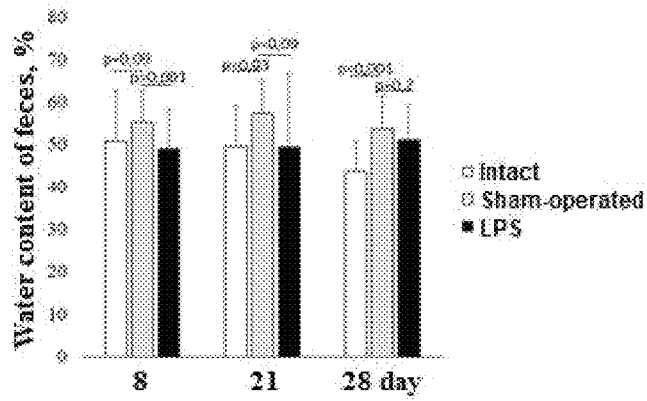
FIG. 57 displays water content of feces in LPS rat models of Parkinson's disease, M+SD.

However, it should be noted that LPS rat models of parkinsonism gained weight between the $1^{st}$ (day of operation) and the $28^{th}$ (day of autopsy) days of the experiment by only 2%, which indicates the relevance of the body weight of animals for the assessment of their general clinical condition and the effects of the test substances on their state in Parkinson's disease (FIG. 57).

Figure 56A:
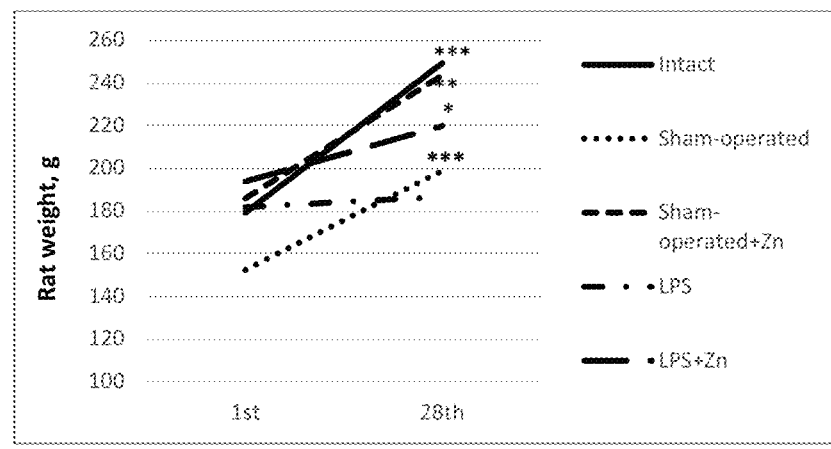
FIG. 56A is a graph of the therapeutic effects of 64Zn-asp on body weight in LPS rat models of parkinsonism, *$p \leq 0.05$, $p \leq 0.01$, *$p \leq 0.001$ versus values on the 1st day of the experiment.
Figure 56B:
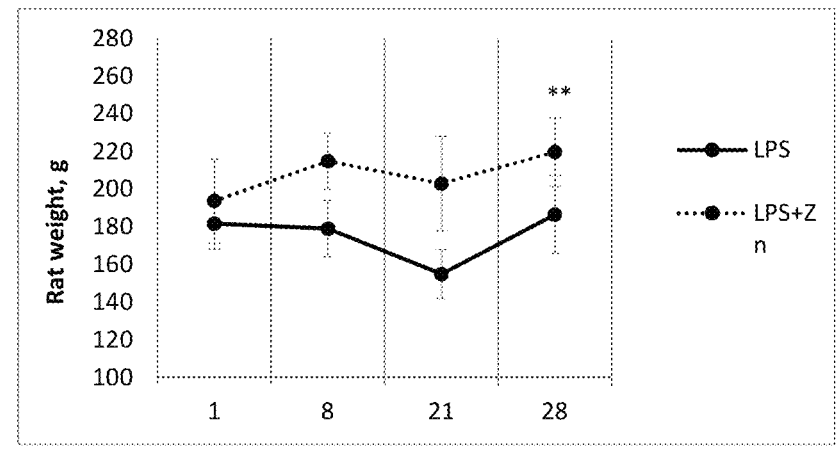
FIG. 56B shows graphically changes in body weight of LPS rat models and in the course of treatment with 64Zn-asp, M±SD, *$p \leq 0.05$, $p \leq 0.01$, *$p \leq 0.001$ versus values in the LPS group.

Administration of $^{64}$Zn-asp to LPS rat models of Parkinson's disease caused a significant increase in their body weight (the difference in values in this group on the $1^{st}$ and $28^{th}$ day of the experiment (FIG. 56A) and in relation to values in the group of LPS rat models which received deuterium-depleted water, on the $28^{th}$ day of the experiment (FIG. 56B).

TABLE 2

Therapeutic effects of $^{64}$Zn-asp on body weight in LPS rat models of parkinsonism, M ± SD

| | Deuterium-depleted water | | | $^{64}$Zn-asp | |
|---|---|---|---|---|---|
| Day | Intact | Sham-operated | LPS | Sham-operated | LPS |
| $1^{st}$ | 179.25 ± 14.62 | 152.41 ± 8.86 | 181.8 ± 13.71 | 185.91 ± 19.90 | 193.78 ± 22.21 |
| $28^{th}$ | 249.25 ± 19.36 | 198.75 ± 13.07 | 186.6 ± 20.66 | 243.50 ± 27.52 | 219.8 ± 18.31 |
| Changes, % | 39*** | 30*** | 2 | 30** | 13* |

Note:
*p < 0.05,
**p < 0.01,
***p < 0.001 vs values in the group between the $1^{st}$ and $28^{th}$ days of the experiment Therapeutic Effects of $^{64}$Zn-Asp on Fecal Water Content in LPS Rat Models of Parkinsonism Despite the main clinical signs of Parkinson's disease, such as tremor, hypokinesia, muscle rigidity, postural instability, it is the early non-motor symptoms of Parkinson's disease that clearly affect the patient's quality of life. Karaban I. N. Non-motor symptoms in the clinical picture of Parkinson's disease/I. N. Karaban., O. V. Shalenko, S. A. Krizhanovsky//*International Neurological Journal.*—2017.—No 1(87).—P.—58-63. The major discomfort among non-motor symptoms is caused by gastrointestinal (GI) dysfunction, including gastric dysmotility, constipation and anorectal dysfunction. Delayed gastric emptying, progressing to gastroparesis, is reported in up to 100% of patients with PD, and it occurs at all stages of the disease with severe consequences to the patient's quality of life [Gastric motor dysfunctions in Parkinson's disease: Current pre-clinical evidence/C. Pellegrini [et al.].//*Parkinsonism Relat Disord.*—2015.—Vol. 21(12).—P. 1407-14]. The water content of feces depends not on dietary intake, but on digestive function, of which it is an accurate reflection. Intestinal peristalsis and the degree of water absorption are related, as well as water absorption and intestinal blood circulation. In every case, fecal hyperhydration is one of the first signs of irritation of the colonic mucosa Jensen R, et al. *Clin Chem.* 1976; 22(8):135.

In this study, an increase in the water content of feces in rats of the sham-operated (SO) group was recorded compared with intact animals, and these disorders were stable over time and were significant even 28 days after the surgery (FIG. 57). In LPS rat models of parkinsonism, significantly smaller fecal water content was observed 8 days after the surgery compared with sham-operated animals. It should, however, be noted that by the $28^{th}$ day of the experiment, a tendency to an increase in the water content of feces in LPS rat models was observed (FIG. 57). This fact confirms the relevance of this model to the clinical picture, namely GI dysfunction in Parkinson's disease.

Figure 58:
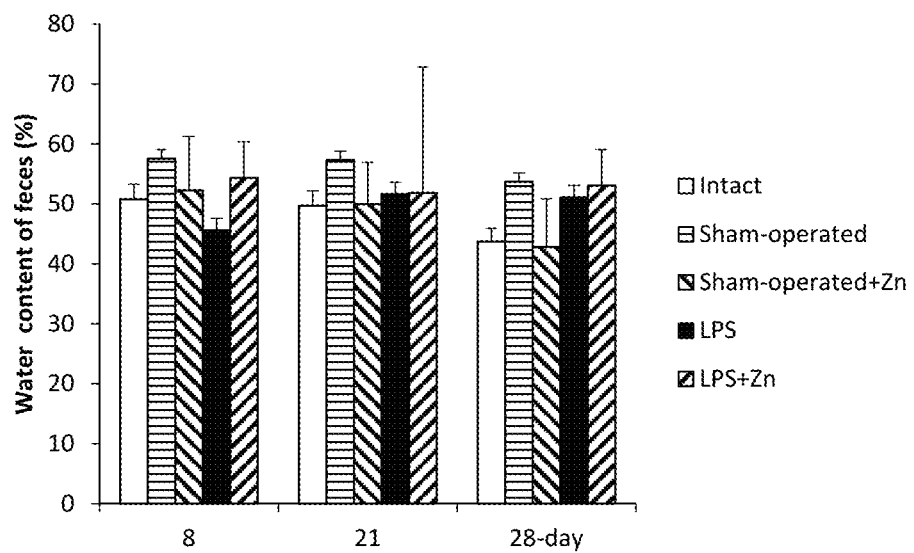
FIG. 58 display the therapeutic effects of 64Zn-asp on fecal water content in LPS rat models of Parkinson's disease, M±SD.
Figure 59A:
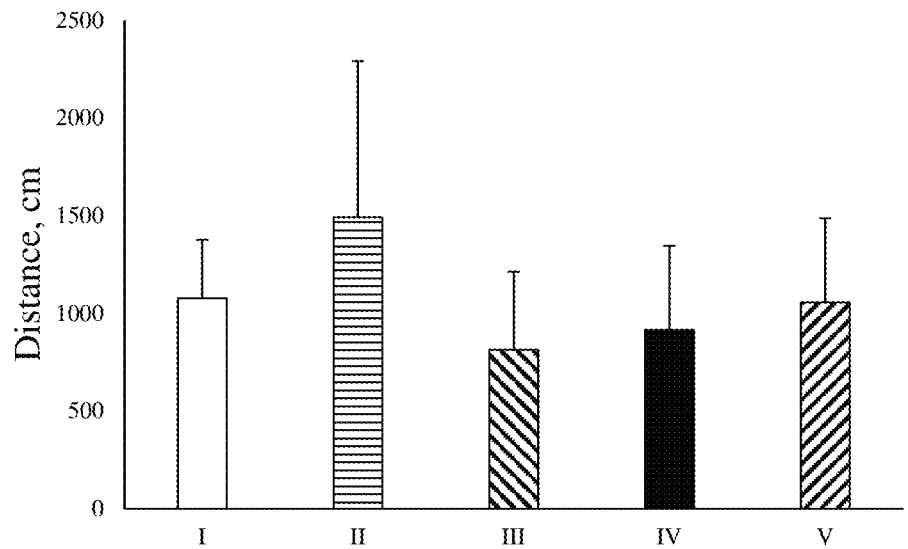
FIG. 59A-FIG. 59E show the effects of 64Zn-asp on behavioral response parameters measured in the open field test.
Figure 59B:
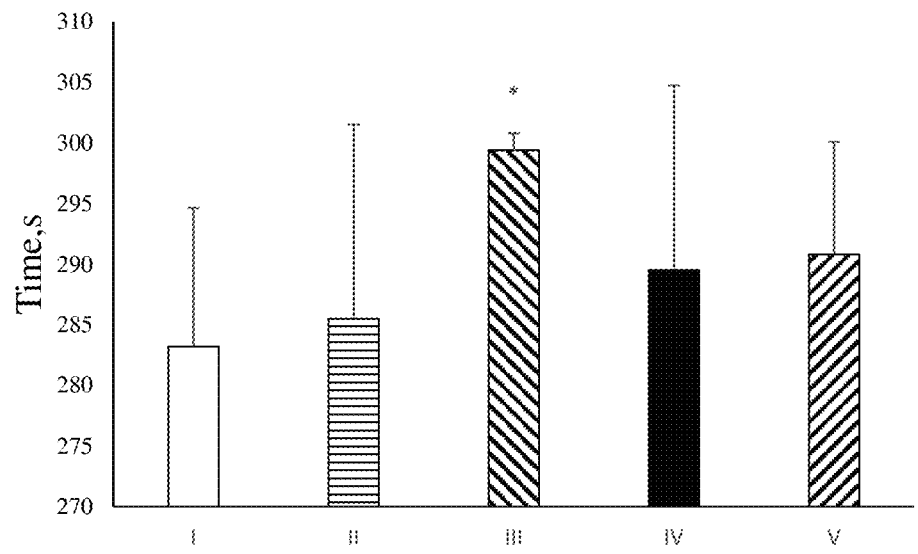
Figure 59C:
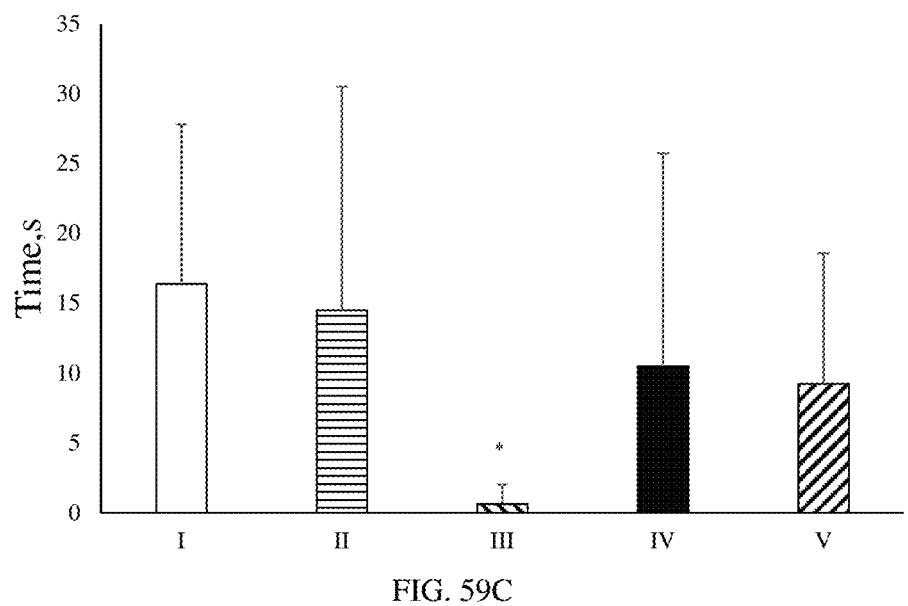
Figure 59D:
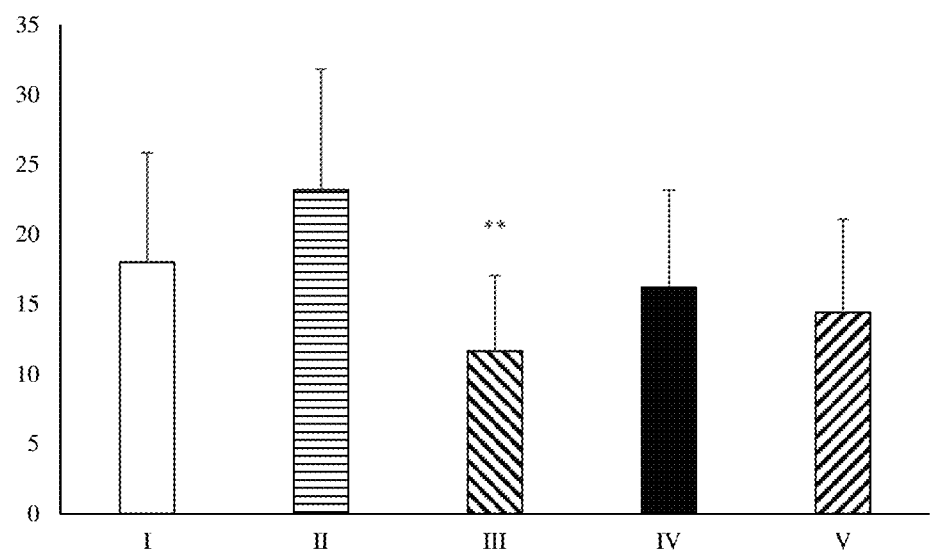
Figure 59E:
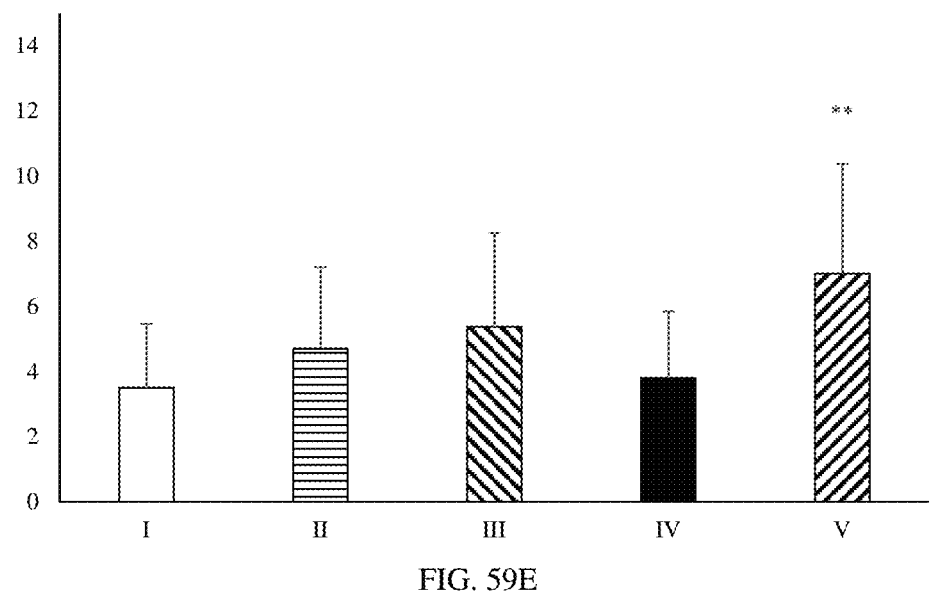
Figure 60A:
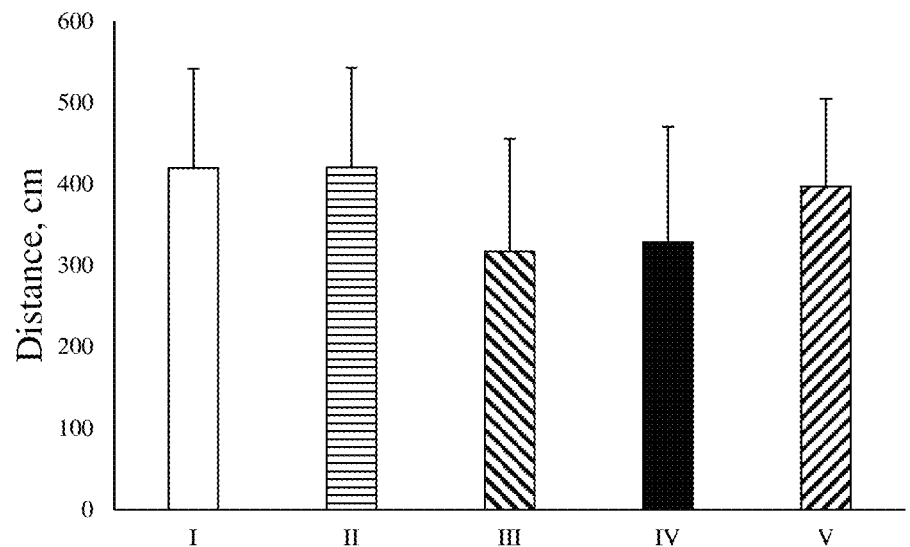
FIG. 60A-FIG. 60D show the effects of 64Zn-asp on behavioral response parameters measured in the elevated plus maze.
Figure 60B:
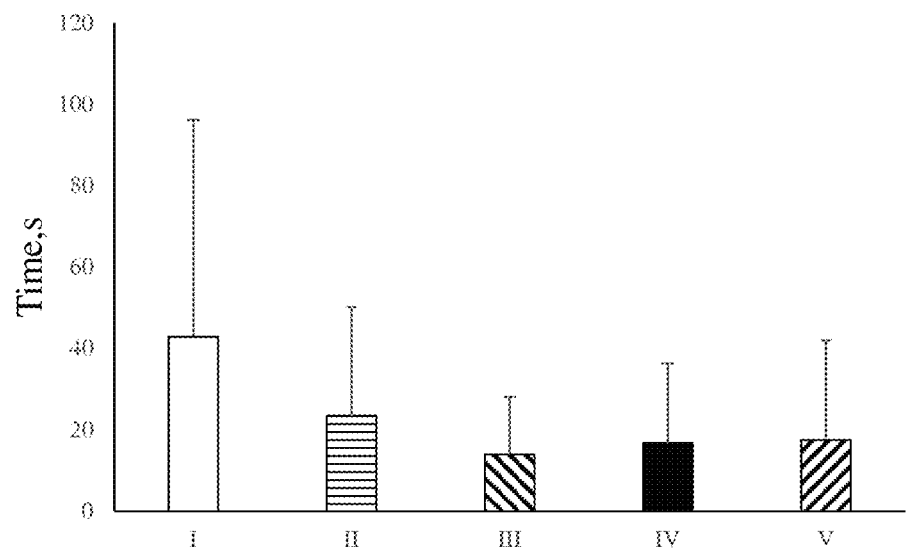
Figure 60C:
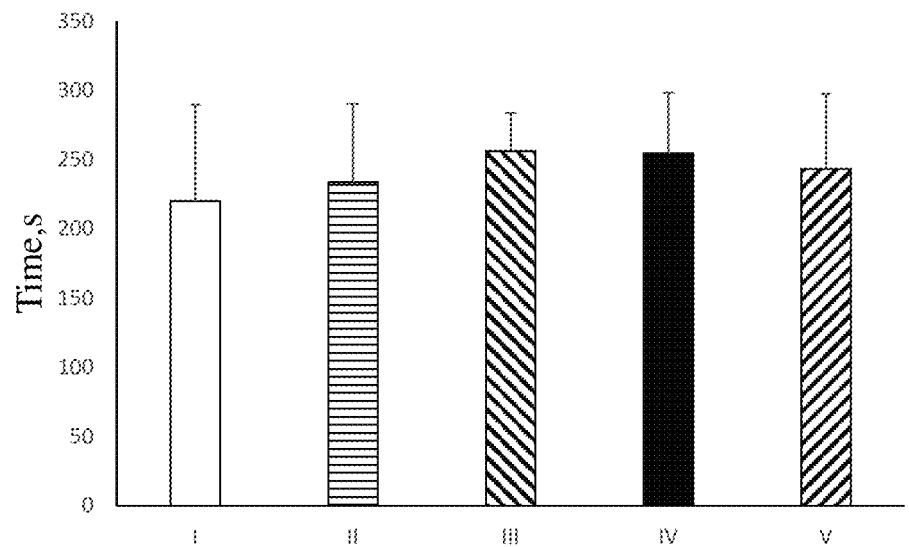
Figure 60D:
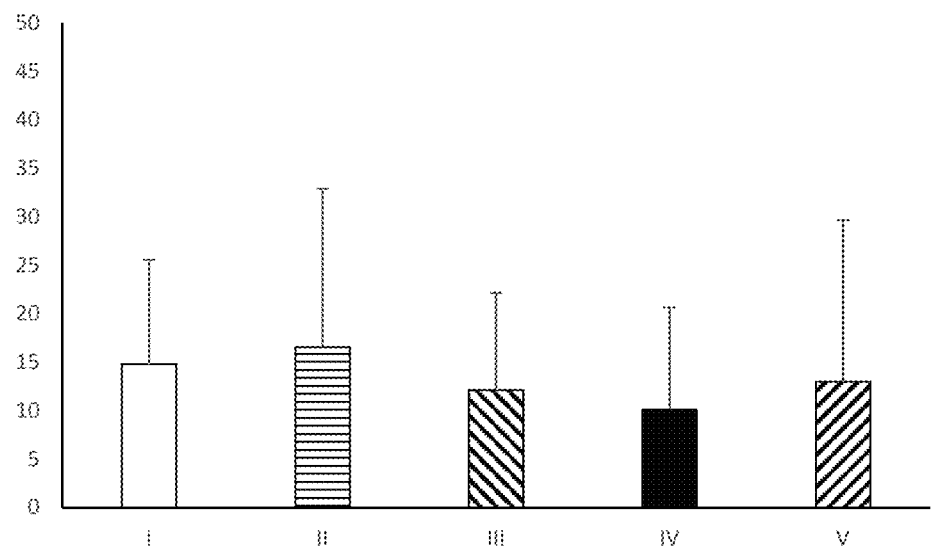

In this study, administration of $^{64}$Zn-asp (FIG. 58) during 10 days after animals were injected LPS to induce parkinsonism did not cause any significant changes in their water content of feces.

Effects of $^{64}$Zn-Asp on Behavioral Responses in LPS Rat Models of Parkinson's Disease in the Open Field Test To assess the effects of $^{64}$Zn-asp on the functions of CNS, a commonly accepted open field test was used. Observance of rat behavioral reactions in this test makes it possible to determine the degree of influence of the test substance on the motor and exploratory activity, orientation response and emotional reactivity of animals. The test results are shown in Table 3 and in FIG. 59A-FIG. 59E.

TABLE 3

Effects of $^{64}$Zn-asp on behavioral response parameters measured in the open field test

| Parameters | Intact rats Gr. I (n = 10) | SO rats Gr. II (n = 10) | SO + $^{64}$Zn-asp Gr. III (n = 10) | LPS Gr. IV (n = 10) | LPS + $^{64}$Zn-asp Gr. V (n = 10) |
|---|---|---|---|---|---|
| Total distance travelled, cm | 1077 ± 259.4 | 1491 ± 718.4 | 812.8 ± 352.4 | 915.2 ± 125.8 | 1056 ± 423 |
| Time spent in the outer perimeter, s | 283.2 ± 11.43 | 285.5 ± 16.03 | 299.4 ± 1.408 | 289.5 ± 15.24 | 290.8 ± 9.333 |
| Time spent in the inner perimeter, s | 16.8 ± 11.43 | 14.5 ± 16.03 | 0.625 ± 1.408 | 10.5 ± 15.24 | 9.235 ± 9.344 |
| Number of rearings | 18 ± 7.846 | 23.2 ± 8.638 | 11.63 ± 5.423 | 16.2 ± 6.973 | 14.4 ± 6.687 |
| Number of defecations | 3.5 ± 1.958 | 4.7 ± 2.497 | 5.375 ± 2.875 | 3.8 ± 2.044 | 7 ± 2.582 |
| Number of groomings | 4 ± 2.055 | 3.9 ± 1.287 | 5.75 ± 2.121 | 4.3 ± 1.418 | 3.5 ± 1.354 |

The results of the open field test showed that none of the behavioral parameters in animals from SO group (group II) differed significantly from those in animals from the intact control (group I).

The Kruskal-Wallis test used to make a comparison between significant groups, namely group II (SO) and groups III (SO+$^{64}$Zn-asp) and IV (LPS) revealed the following:
- a slight decrease in the total distance covered by animals (P=0.0505);
- an increase in the time spent in the outer perimeter and a decrease in the time spent in the inner perimeter (P=0.0020), with a significant difference between groups II (SO) and III (SO+$^{64}$Zn-asp) (Dunn's multiple comparisons test P=0.0193);
- reduction of the total number of rearings by groups (P=0.0160), with a significant difference between groups II (SO) and III (SO+$^{64}$Zn-asp) (Dunn's multiple comparisons test P=0.0053).

Further, to analyze the effects of $^{64}$Zn-asp on the behavioral parameters in the open field test, a comparison was made between the significant groups, namely group IV (LPS) and group V (LPS+$^{64}$Zn-asp), which showed the following: administration of the test substance did not have any effect on the total distance travelled (Kruskal-Wallis test—P value=0.7031), time spent in the outer perimeter (left chart) and the inner perimeter (right chart) (Kruskal-Wallis test—P value=0.2319), the total number of rearings (Kruskal-Wallis test—P value=0.7001); the number of groomings (Kruskal-Wallis test—P value=0.3022).

It should be noted that the frequency of defecations in $^{64}$Zn-asp-treated LPS rat models of PD increased in comparison with LPS rat models of PD injected with deuterium-depleted water (Dunn's multiple comparisons P=0.0030).

Effects of $^{64}$Zn-Asp on Behavioral Responses in LPS Rat Models of Parkinson's Disease in the Elevated Plus Maze The elevated plus maze was used to analyze the effects of $^{64}$Zn-asp on the functions of CNS in experimental animals. This test made it possible to assess the degree of influence of the test substance on the levels of anxiety in rats by observing their behavioral responses. The test results are presented in Table 4 and in FIG. 60A-FIG. 60D.

TABLE 4

Effects of $^{64}$Zn-asp on behavioral response parameters measured in the elevated plus maze

| Parameters | Intact rats Gr. I (n = 10) | SO Gr. II (n = 10) | SO + $^{64}$Zn-asp Group III (n = 10) | LPS Gr. IV (n = 10) | LPS + $^{64}$Zn-asp Gr. V (n = 10) |
|---|---|---|---|---|---|
| Total distance travelled, cm | 419.4 ± 122 | 420.4 ± 122.4 | 317.1 ± 138.4 | 328.5 ± 141.6 | 396.8 ± 107.7 |
| Time spent in open arms, s | 42.9 ± 53.28 | 23.54 ± 26.72 | 14 ± 14.12 | 16.8 ± 19.57 | 17.55 ± 24.48 |
| Time spent in closed arms, s | 220.1 ± 69.68 | 233.7 ± 56.78 | 256.1 ± 27.69 | 254.7 ± 43.66 | 243.3 ± 54.2 |
| Number of entries into closed arms | 7 ± 5.477 | 8 ± 8.292 | 5.875 ± 5.139 | 4.8 ± 5.827 | 6.1 ± 8.279 |
| Number of entries into open arms | 7 ± 5.477 | 8 ± 8.292 | 5.375 ± 5.317 | 4.8 ± 5.827 | 6.1 ± 8.279 |
| Total number of entries | 14.8 ± 10.76 | 16.56 ± 16.33 | 12.13+ 10.02 | 10.1 ± 11.55 | 13 ± 16.66 |

The results of the elevated plus maze showed that none of the behavioral parameters in animals from SO group (group II) differed significantly from those in animals from the intact control (group I).

The Kruskal-Wallis and ANOVA tests used for comparing between significant groups, namely group II (SO) and groups III (SO+$^{64}$Zn-asp) and IV (LPS), revealed no significant changes in any of the parameters analyzed. However, quantitative data (Table 4) show a reduction in the total distance travelled, the time spent in the open arms and the number of entries in group IV (LPS) by 1.3, 1.4 and 1.6 times, respectively, when compared with group II (SO).

To further analyze the effects of $^{64}$Zn-asp on the behavioral parameters of rats in the elevated plus maze a comparison was made between significant groups, namely group IV (LPS) and group V (LPS+$^{64}$Zn-asp), which revealed that administration of the test substance had not produced any effects on the behavioral parameters of the experimental animals. The quantitative data (Table 4) show that $^{64}$Zn-asp increased the total distance travelled and the number of entries in group V by 1.2 and 1.3 times, respectively, when compared with group IV (LPS).

Effects of $^{64}$Zn-Asp on Behavioral Responses in LPS Rat Models of Parkinson's Disease in the Pick-Up Test The pick-up test is a test for increased irritability. The animals were picked up by grasping around the body. Responses were scored from 1 to 6. The test results are presented in FIG. 61.

The results of the pick-up test showed that none of the behavioral parameters in animals from SO group (group II) differed significantly from those in animals from the intact control (group I).

Figure 61:
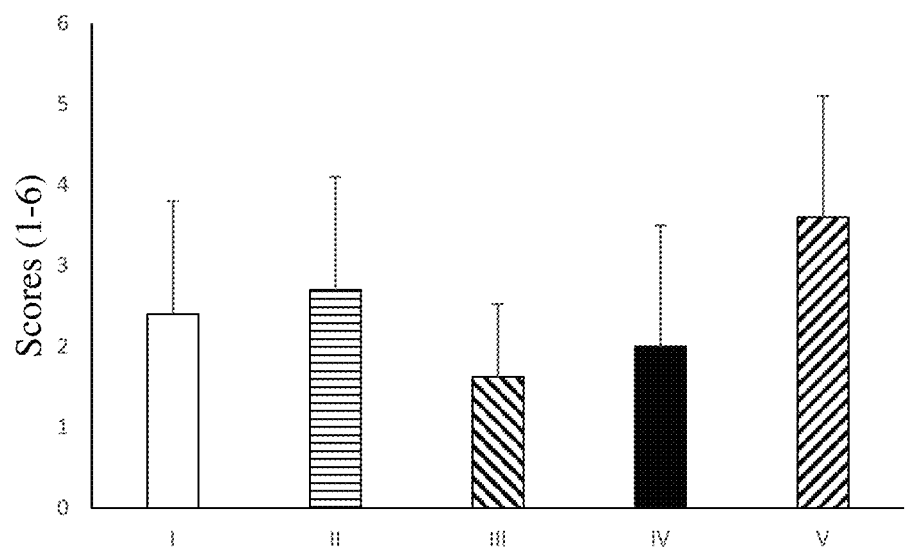
FIG. 61 displays the effects of 64Zn-asp on behavioral response parameters measured in the pick-up test.

The Kruskal-Wallis and ANOVA tests used for comparing between significant groups, namely group II (SO) and groups III (SO+$^{64}$Zn-asp) and IV (LPS), revealed no significant changes in the behavioral response of animals. FIG. 61.

To further analyze the effects of $^{64}$Zn-asp on the behavioral parameter observed in the pick-up test a comparison was made between significant groups, namely group IV (LPS) and group V (LPS+$^{64}$Zn-asp), which revealed a statistically significant elevation of irritation in group V (LPS+$^{64}$Zn-asp) compared with group IV (LPS) (Dunn's multiple comparisons test P=0.0136).

Therapeutic Effects of $^{64}$Zn-Asp on Blood Count Values in LPS Rat Models of Parkinsonism Parkinson's disease is currently regarded as a disease accompanied by systemic meta-inflammation. The causes of systemic inflammation include violation of the blood-brain barrier with an export of proinflammatory brain mediators to the periphery, transport of inflammatory mediators through the glymphatic system, as well as peripheral disorders associated with neurodegeneration, including gastrointestinal dysfunction (peptic ulcer, impaired intestinal motility, etc.) and dysbiosis. Grozdanov V, et al. Acta Neuropathol. 2014 November; 128(5):651-63. doi: 10.1007/s00401-014-1345-4; Akil E, et al., Neurol Sci. 2015 March; 36(3):423-8. doi: 10.1007/s10072-014-1976-1. It should be noted that the analysis of blood counts was carried out upon completion of the experiment, i.e., 10 days after the end of treatment with the test substance.

Figure 62:
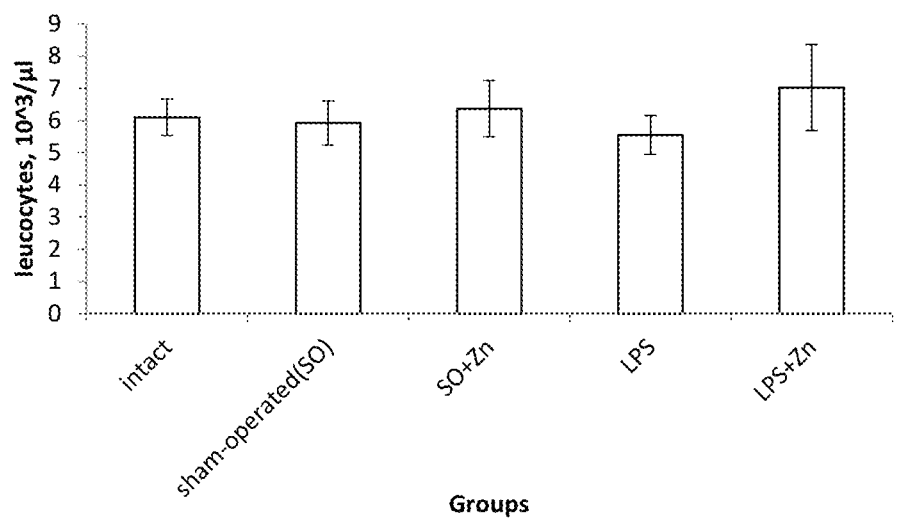
FIG. 62 displays the effects of 64Zn-asp on the levels of circulating leukocytes in LPS rat models of parkinsonism, M±SD. Note: #$p \leq 0.05$ vs. intact animals, $ $p \leq 0.05$ vs. sham-operated animals.

Analysis of blood samples from LPS animal models of Parkinson's disease showed no statistically significant changes in the absolute number of circulating leukocytes in these rats compared with intact and sham-operated animals (FIG. 62).

Figure 63:
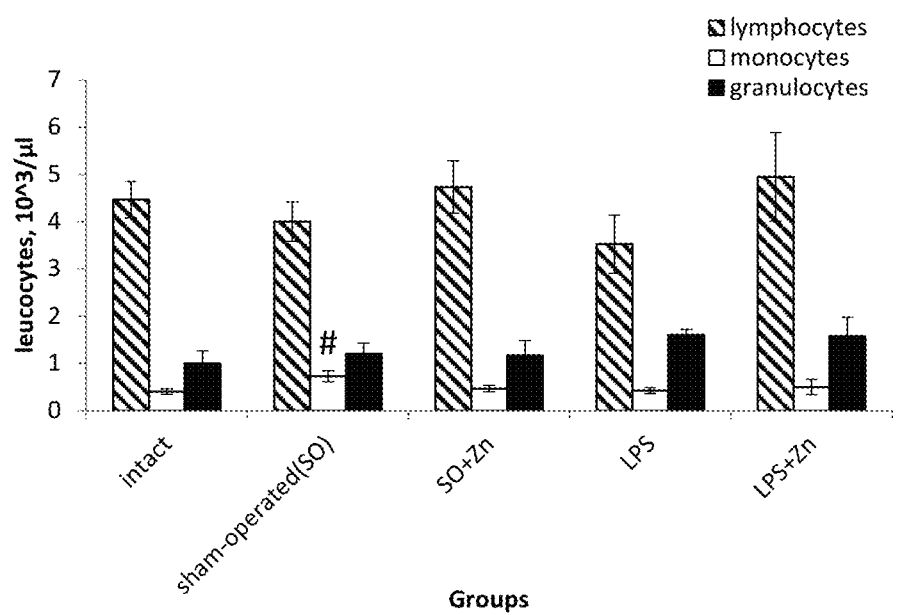
FIG. 63 shows the effects of $^{64}$Zn-asp on the absolute number of circulating leukocytes of various populations in LPS rat models of parkinsonism, M±SD. Note: #$p \leq 0.05$ vs. intact animals, $ $p \leq 0.05$ vs. sham-operated animals, * $p \leq 0.05$ vs. animal models of Parkinson's disease.
Figure 64:
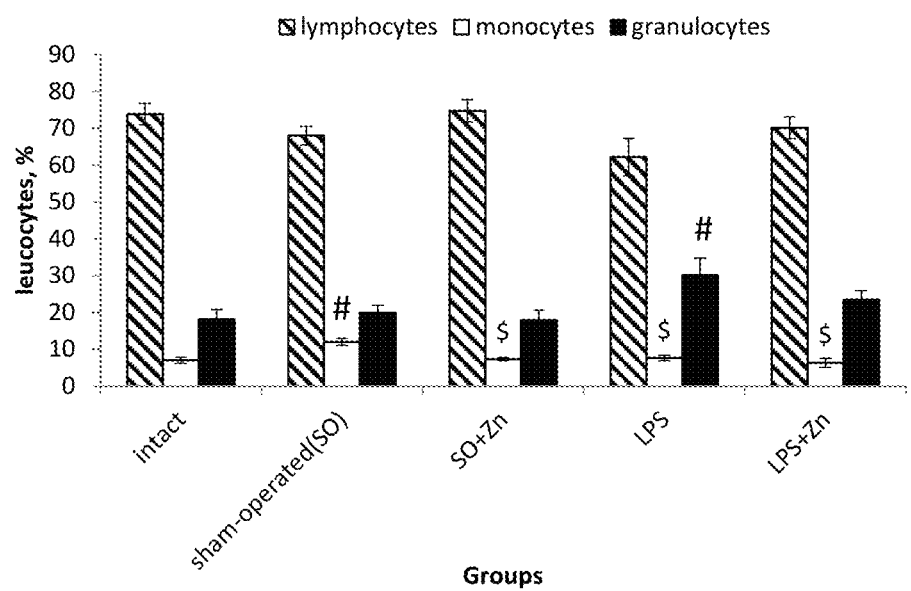
FIG. 64 shows the effects of 64Zn-asp on the relative number of circulating leukocytes of various populations in LPS rat models of parkinsonism, M±SD.

Therapeutic administration of the test substance did not influence this hemogram parameter. Analysis of the absolute number of leukocytes in the main populations showed a slightly different picture (FIG. 63). Sham operation was accompanied by mild monocytosis.

Administration of the zinc preparation levelled this inflammatory phenomenon.

Induction of parkinsonism was accompanied by neutrophilia with an increase in the neutrophil-to-lymphocyte ratio, which is a typical characteristic of blood count results in idiopathic parkinsonism, one of the early markers of the disease progression and an important prognostic criterion for its severity. Wijeyekoon R S, et al., Front Neurol. 2018; 9:870. doi: 10.3389/fneur.2018.00870. Therapeutic administration of the zinc preparation was associated with normalization of the neutrophil-to-lymphocyte ratio, primarily due to an increase in lymphocyte levels, which is a criterion for resolution of inflammation involving regulatory cells.

A somewhat different picture was obtained in the analysis of a relative number of leukocytes of various populations (FIG. 66).

A sham operation caused an increase in the relative number of monocytes, which confirms the presence of systemic inflammation in response to surgery. The use of the test substance levelled monocytosis. In addition to an increase in the neutrophil-to-lymphocyte ratio, the development of parkinsonism was also accompanied by monocytosis, which fact is demonstrated by the results of analysis of the relative number of leukocytes of the main populations. Therapeutic administration of the test substance reduced peripheral inflammation.

Therapeutic Effects of $^{64}$Zn-Asp on Functional and Phenotypic Properties of Microglia in LPS Rat Models of Parkinsonism Phagocytic activity of microglia is an indicator of their activated state, any changes in which should be viewed in the context of changes in other functional and phenotypic characteristics. The results of this study show that the number of phagocytic microglia cells and their endocytic activity in sham-operated animals was significantly higher than in intact animals, which, given satisfactory physiological condition of the animals in this group, should be considered as a sign of activation of reparative inflammatory processes after the surgical intervention (FIG. 65A and FIG. 65B). Administration of the zinc preparation to sham-operated animals was accompanied by a decrease in the relative number of phagocytic microglia and a decrease in their endocytic (phagocytic) activity, which indicates that they have an anti-inflammatory effect. The progression of PD was accompanied by a decrease in the phagocytic activity of microglia, which, given a symptomatic manifestation of the disease, can be considered as a sign of suppression of the scavenger or patrolling function of homeostasis of tissue-resident macrophages in the brain. Therapeutic administration of the zinc preparation had different effects on this functional indicator of microglia in LPS animal models of PD. We observed a sharp increase in the phagocytic activity of microglia in animals that received zinc, which, given physiological condition of the animals in this group, can be considered as a sign of activation of reparative processes in the brain.

The results of this study of the oxidative metabolism of microglia are supported by the data on the phagocytic activity of these cells (FIG. 66). Microglia in intact animals were characterized by the absence of a pronounced response to in vitro stimulation, which indicates a resting state of metabolically conservative phagocytes, i.e. resident mononuclear phagocytes.

Oxidative metabolism in sham-operated animals was enhanced at the time of the experiment, which confirms our assumption about a persistent reparative inflammatory process. An additional criterion for such a process is the presence of a functional reserve in microglia in animals of this group, as evidenced by a statistically significant positive response to in vitro PMA treatment. The presence of a functional reserve can be considered as a sign of the presence of recruited circulating mononuclear phagocytes in the analyzed population.

Administration of the zinc preparation to sham-operated animals was accompanied by a decrease in the oxidative metabolism of microglia, which confirms our conclusion about their anti-inflammatory action. The oxidative metabolism in animal models of PD was sharply reduced compared with that in sham-operated animals. Considering physiological condition of the animals and the fact that the rats of this group also underwent surgery, a lack of activated generation of reactive oxygen species can be considered as a sign of functional depletion of microglia. Administration of the test substance slightly but statistically significantly increased the oxidative metabolism of microglia, which supports our earlier suggestion that this preparation activates reparative processes.

Results of the analysis of phenotypic profile of microglia are presented in FIG. 67A and FIG. 67B.

To characterize the phenotypic profile, the following markers were selected: CD206 (scavenger receptor, a marker of alternative polarization of phagocytes of extra-cerebral localization and also a marker of activated resident microglia (see the report on the previous project) and CD80/86 (costimulatory molecules involved in the process of antigen presentation, which are markers of pro-inflammatory activation of phagocytes of extra-cerebral localization and which are also overexpressed by myeloid-derived suppressor cells, negative regulators of proinflammatory reactions of innate and adaptive immunity). According to the results of this study, the expression of all analyzed markers was increased in sham operated animals, which indicates an activated state of microglia. Administration of the zinc preparation was accompanied by a decrease in the expression of all phenotypic markers under study. However, the number of CD206+ and CD80+ cells in animals of this group sharply increased. Apparently this is also a marker of enhanced reparative processes. Microglia originate from the yolk sac, and the microglial pool colonizes the brain in the early period of embryogenesis. This unique population of resident phagocytes maintains their number by self-healing (proliferation and differentiation of stem tissue elements) and without recruiting immature bone-marrow precursors from the circulation. Increased expression of any phenotypic markers is a sign of the cell differentiation process, which allows a conclusion that an increase in the CD206+ and CD80+ fraction occurred as a result of differentiation of immature resident tissue elements.

The phenotypic profile of LPS rat models of PD was different from that in rats with 6-OHDA-induced disease. Microglia in LPS animal models of PD was characterized by a significantly reduced—compared with sham-operated animals—expression level of all the studied markers, which confirms our assumption about functional depletion of these cells caused by a prolonged inflammatory process. However, a fraction of CD206+ cells was quite large, which may indicate an arbitrary healing, a reparative inflammation (it should be noted that the analysis of all phagocytic immune reactivity indicators was carried out at the end of the experiment, that is, 28 days after induction of the disease). Administration of the zinc preparation was accompanied by increased expression of the marker of alternative (anti-inflammatory, reparative) activation of phagocytosis by microglia—CD206, as well as a significant increase in the expression of CD86, a marker inherent in myeloid-derived suppressor cells. It can be assumed that the zinc preparation promotes differentiation and/or recruitment of regulatory inflammatory cells. However, the suggested assumption requires additional experimental confirmation, since, according the study protocol, we were not allowed to differentiate myeloid-derived suppressor cells phenotypically.

Thus, the development of LPS-induced Parkinson's disease is accompanied by functional depletion of microglia caused, in all likelihood, by a prolonged local inflammatory process. The use of the zinc preparation, accompanied by a positive therapeutic effect, was associated with an increase in the metabolic activity of microglia with a significant activation of their phagocytic function involved in reparative processes, which may be indicative of the restorative homeostatic effect of the test substance.

Therapeutic Effects of $^{64}$Zn-Asp on Functional and Phenotypic Properties of Circulating Phagocytes in LPS Rat Models of Parkinsonism As described above, the development of PD is accompanied by the formation of systemic inflammation which increases and maintains the persistence of neuro-inflammatory processes. This circumstance makes effector cells of the systemic inflammatory process no less attractive targets of anti-inflammatory therapy for PD than resident intracerebral inflammatory effectors. This was one of the reasons for analyzing functional and phenotypic properties of circulating phagocytes. Another reason for the analysis was the fact that the zinc preparation was administered intravenously, which made circulating phagocytes the first line of respondent cells. As described above, the results of blood counts showed the presence of a systemic inflammatory process in LPS animal models of PD with significant neutrophilia and an increase in the neutrophil-lymphocyte ratio, a validated indicator of systemic inflammatory response. Analysis of the functional and phenotypic properties of circulating phagocytes confirmed these observations (FIG. 68A and FIG. 68B). The number of phagocytic cells in the peripheral blood of sham-operated animals exceeded that of intact animals, which indicates activation of hematopoiesis, probably associated with an inflammatory reparative process. Zinc did not have any effect on this parameter.

Phagocytic activity of monocytes and granulocytes in the peripheral blood of sham-operated animals was not significantly different from that in intact rats. Administration of the test substance did not have any effect on this parameter. Oxidative metabolism of circulating phagocytes in sham-operated animals significantly reduced compared with that in intact animals (FIG. 69A and FIG. 69B).

The zinc preparation did not have any significant effect on this parameter. In general, it can be concluded that the metabolic profile of circulating phagocytes of this group of animals had an anti-inflammatory character (which may be evidence of persistent reparative processes after surgical intervention) and was not significantly affected by the test substance administration.

The levels of phagocytic cells in the blood of animal models of PD were lower than those in sham-operated rats. Considering surgical manipulations that require activation of reparation, the result obtained from these animals may indicate depletion/inhibition of hemato(myelo)poiesis caused by progression of the disease. The zinc therapy was accompanied by a slight decrease in the relative number of circulating monocytes and did not produce any effect on the aforementioned granulocyte index.

Phagocytic activity of circulating monocytes and granulocytes in rat models of PD was significantly lower compared with that in sham-operated and intact rats. At the same time, the values of oxidative metabolism of these cells significantly exceeded those in the control groups. This is evidence of a pro-inflammatory metabolic shift of cells and a marker of a systemic inflammatory process. Circulating phagocytes of both populations in animal models of PD treated with the zinc preparation were characterized by a sharply reduced oxidative metabolism, which indicates an anti-inflammatory character of the systemic modulating effect exhibited by the test substance. It should be noted that the zinc preparation has an ability to restore a functional reserve of oxidative metabolism of circulating phagocytes.

Analysis of expression of phenotypic markers by circulating phagocytes in all groups of animals revealed the following (FIG. 70A and FIG. 70B). The expression of CD206 (a marker of alternative, anti-inflammatory polarization of extra-cerebral phagocytes) was significantly higher in sham-operated animals compared with intact rats. The number of positive cells did not differ from that in healthy animals. The identified phenomenon supports the above-stated assumption about a reparative nature of the inflammatory process in these animals after surgical intervention. The expression levels of costimulatory molecules CD80/86 (which is a marker of the classic pro-inflammatory polarization of extra-cerebral phagocytes) were also increased in sham-operated animals. Taking into account physiological condition of animals of this group and the fact that a marker of the population of myeloid-derived suppressor cells (found in the circulating blood of animals showing systemic inflammatory processes) described in the recent literature and mentioned above [Wang W, et al. *Eur J Immunol.* 2015; 45(2):464-73. doi: 10.1002/eji.201444799], it can be assumed that an increase in the expression of these markers and the number of positive cells in the populations of circulating phagocytes may be attributed to an increase in the number of myeloid-derived suppressor phagocytes caused by activation of reparative processes in these animals. Sham-operated animals treated with the zinc preparation showed a decrease in expression of these markers to the levels (and even below the levels) showed by intact animals, which may indicate a homeostatic restoration of the phenotypic profile of blood phagocytes under the action of the test substance. The levels of expression of all three analyzed phenotypic markers in animal models of PD were significantly lower than those in sham-operated animals, which, given physiological condition of animals of this group indicates, first of all, functional depletion of these cells. Administration of the zinc preparation promoted an increase in the expression levels of all three markers, which suggests an anti-inflammatory functional shift of circulating phagocytes of animal models of PD.

Therapeutic Effects of $^{64}$Zn-Asp on Functional and Phenotypic Properties of Peritoneal Phagocytes in LPS Rat Models of Parkinsonism Analysis of the phenotypic and functional profile of peritoneal phagocytes, which are part of MALT (Mucosal-Associated Lymphoid Tissue) immunocytes, revealed their fluctuations in animals of all experimental groups, which indicates involvement of this immune system compartment in the development of neurodegenerative pathology and generalized nature of the underlying inflammatory process.

Phagocytic activity of peritoneal macrophages and the relative number of phagocytic cells in the peritoneal exudate of sham-operated animals were higher than those in intact rats, which should be considered as involvement of the mucosal immune system in the generalized inflammatory process (FIG. 71A and FIG. 71B). Administration of the zinc preparation reduced the aforementioned values to the levels of intact animals, which indicates a homeostatic nature of its immunomodulating effect. Values of phagocytic activity of peritoneal macrophages in animal models of PD were at the levels of intact rats and significantly lower than those of sham-operated animals. Given physiological condition of animals in this group, we can assume that a systemic inflammatory process of a reparative character is absent. Administration of the test substance contributed to the activation of phagocytic activity of the peritoneal exudate cells, which can be attributed to the initiation of the systemic inflammatory reparative process.

Oxidative metabolism of peritoneal macrophages in sham-operated rats was significantly higher than that in intact animals, which confirms the hypothesis that mucous phagocytes are involved in generalized reparative inflammatory process (FIG. 72). Administration of the zinc preparation reduced the production of reactive oxygen species by peritoneal phagocytes, which indicates an anti-inflammatory character of their immunomodulating effect.

Oxidative metabolism of peritoneal phagocytes in animal models of PD was significantly lower than that in sham-operated animals. Administration of the zinc preparation was accompanied by a decrease in the oxidative metabolism of the peritoneal exudate cells, which indicates an anti-inflammatory nature of the action produced by the test substance.

Analysis of the phenotypic profile of peritoneal phagocytes revealed diverse changes in the expression of the studied markers in the groups of experimental animals, partly different from those registered for circulating cells. This could probably be due to different origins of phagocytes of the peritoneal cavity (embryonic origin) and peripheral blood phagocytes (bone marrow origin). The expression levels of all three studied markers in peritoneal macrophages in sham-operated animals only slightly differed from those in intact rats (FIG. 73A and FIG. 73B). Administration of the zinc preparation caused a sharp increase in the expression of all phenotypic marker.

A similar situation was observed in a comparative analysis of the phenotypic profile of peritoneal macrophages in animal models of PD. The expression levels of all the studied phenotypic markers in parkinsonian rats only slightly differed from those in the control animals. Administration of the zinc preparation caused a significant increase in the expression of all markers. In the context of clinical scores of animals treated with the test substance having compared phenotypic parameters of phagocytes of other localizations, we can claim the activation of metabolism of an anti-inflammatory character in MALT phagocytes involved in the systemic inflammatory response.

Therapeutic Effects of $^{64}$Zn-Asp on Neuronal Nitric Oxide Synthase Expression in Astrocytes in LPS Rat Models of Parkinsonism The highest activity of this enzyme is found in the cerebellar neurons and in astrocytes. Lower levels of its activity are observed in the hypothalamus, midbrain, striatum, cortex, hippocampus and medulla. In the nervous tissue, this enzyme performs primarily the functions of a neurotransmitter that controls oscillatory activity of neurons, nociception, etc. Its role in controlling the vascular tone of the brain and trophic mechanisms in the nervous tissue is extremely important. The results of our study show that conducting a sham operation and the development of LPS-induced PD were accompanied by a slight decrease in the expression levels of nitric oxide synthase enzyme in astrocytes (FIG. 74). Administration of the zinc preparation caused an increase in its expression, which indicates a positive effect of the test substance on neuronal signaling, disorders of which are characteristic of neurodegenerative processes.

Findings

In LPS rat models of parkinsonism, the mean number of rotations between the $1^{st}$ and $2^{nd}$ apomorphine tests does not change significantly. However, an increase in the absolute number of rotations was observed in 66.6% of rats and a decrease in the number of rotations was observed in 33.3% of rats. Immunohistochemical study showed a 3-fold decrease in the number of TH-positive neurons in the midbrain of LPS rat models compared with sham-operated animals.

Administration of $^{64}$Zn-asp starting from the $9^{th}$ day after the animals were given LPS to induce parkinsonism did not cause a significant change in the mean number of rotations per 30 min between the $1^{st}$ and $2^{nd}$ apomorphine tests but increased the number of animals that produced a smaller absolute number of rotations between the $1^{st}$ and $2^{nd}$ apomorphine tests by 85.7%. This indicates a significant efficacy of $^{64}$Zn-asp in preventing the intensity of the process of degeneration of dopaminergic neurons in the black substance, which is confirmed by immunohistochemical data showing a significant increase in the number of TH-positive neurons in the midbrain.

Progression of LPS-induced parkinsonism is associated with a significant—up to 30%—loss of body weight in LPS animal models compared with intact and sham-operated animals. Administration of $^{64}$Zn-asp resulted in a statistically significant increase in the body weight in LPS animal models.

Administration of $^{64}$Zn-asp during 10 days after the animals were given LPS to induce parkinsonism did not cause any significant changes in the water content of feces in the LPS rat models.

The behavioral tests conducted as part of the study showed that the test substance had no significant effects on the levels of locomotor activity, anxiety or irritability in the experimental animals.

Progression of LPS-induced Parkinson's disease is accompanied by functional depletion of phagocytosis of microglia caused by a prolonged local inflammatory process. The use of the zinc preparation, accompanied by a positive therapeutic effect, was associated with an increase in the metabolic activity of microglia with a significant activation of their phagocytic function involved in reparative processes, which may be indicative of the restorative homeostatic effect of the test substance.

Progression of LPS-induced parkinsonism is accompanied by pronounced peripheral inflammation, as evidenced by monocytosis in combination with an increase in the neutrophil-lymphocyte ratio. Therapeutic administration of the zinc preparation reduces systemic inflammatory responses.

Phenotypic and metabolic characteristics of circulating phagocytes indicate their functional depletion caused by prolonged systemic inflammatory process, simultaneously with a proinflammatory shift in their functional activity. Administration of the zinc preparation is accompanied by a functional restoration of circulating phagocytes with an anti-inflammatory shift in their metabolism.

Progression of LPS-induced parkinsonism is accompanied by involvement of MALT immunocytes in the generalized inflammatory process with their proinflammatory activation. Administration of the zinc preparation induces homeostatic changes in metabolism in these cells with their proinflammatory metabolic shift.

Progression of LPS-induced parkinsonism is accompanied by reduction in the levels of neuronal nitric oxide synthase expression. A course of treatment with the zinc preparation restores homeostasis of this neurotransmitter.

CONCLUSION

The results of this study show that PD progression may be caused by activation of an inflammatory process in microglia accompanied by a threefold decrease in the number of viable (expressing tyrosine hydroxylase) dopamine neurons in the substantia nigra. This inflammatory process spreads systemically and covers such extracerebral compartments of the immune system as blood and MALT. Considering the fact that the study of immune reactivity parameters was carried out at the end of the treatment course with the test substance, we evaluated them in animals after a prolonged inflammatory process. Therapeutic administration of the zinc preparation (after the fact of registration of PD progression, which is quite substantial) resulted in a statistically significant increase in the number of viable dopamine neurons in the substantia nigra, which is the most validated indicator of therapeutic efficacy of drugs studied using experimental PD models. Pronounced therapeutic effects of the zinc preparation were accompanied by positive (anti-inflammatory) changes in immunocytes of various localization, which indicates a positive effect of the test substance, administered systemically, on the local (in the brain) and systemic inflammatory process accompanying the PD progression. Considering the effects of the test substance on mucosal immunocytes, we cannot exclude its effects on the gut microbiota as well, both direct (by influencing metabolism in the microbiota, which largely depends on the homeostasis of microelements) and mediated (by influencing the ratio of aerobic and anaerobic conditions). The ability of the test substance to influence the gut microbiota can be an important mechanism for its efficacy in the treatment of neurodegenerative diseases, which are closely related to gut-brain axis disorders. In addition, we cannot exclude the efficacy of this preparation in the treatment of inflammatory bowel diseases, the increasing prevalence of which actualizes a search for effective multi-target therapeutic agents.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

We claim:

1. A method of treating, preventing, or slowing the progression of a neurodegenerative disease comprising administering to a subject in need thereof a therapeutically effective amount a composition comprising: an $^{85}Rb_e$ compound of the following formula:

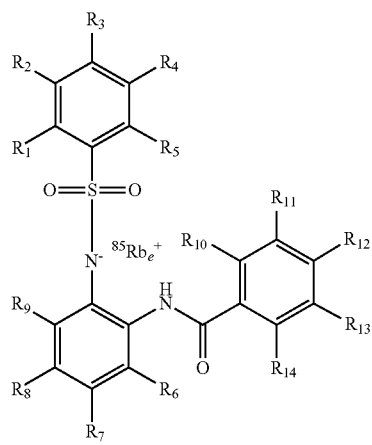

Formula 1 wherein each of $R_1$ through $R_{14}$ is independently selected from H, OH, F, Cl, Br, I, $C_1$-$C_6$ alkyl, $C_1$-$C_6$ alkoxy, and $NO_2$ and the $^{85}Rb_e$ is at least 75% $^{85}Rb$, and a salt, and/or a compound or complex of $^{64}Zn_e$.

2. The method of claim 1, wherein the $^{85}Rb_e$ is at least 90% $^{85}Rb$ and/or the $^{64}Zn_e$ is at least 90% $^{64}Zn$.

3. The method of claim 1 wherein $R_1$, $R_2$, $R_4$-$R_6$, $R_8$, $R_{10}$, $R_{11}$, and $R_{13}$ are all H.

4. The method of claim 1, wherein $R_3$ is selected from H, $CH_3$, $OCH_3$, and $NO_2$, $R_7$ and $R_9$ are each independently selected from H and $OCH_3$, and $R_{12}$ and $R_{14}$ are each independently selected from H, Br, I, and $NO_2$.

5. The method of claim 1, wherein
 a) $R_3$ is $CH_3$ and $R_7$, $R_9$, $R_{12}$, and $R_{14}$ are all H,
 b) $R_3$, $R_7$, $R_9$, $R_{12}$, and $R_{14}$ are all H,
 c) $R_3$ is $CH_3$, $R_{14}$ is Cl, and $R_7$, $R_9$, and $R_{12}$ are all H,
 d) $R_3$ is $CH_3$, $R_{14}$ is OH and $R_7$, $R_9$, and $R_{12}$ are all H,
 e) $R_{14}$ is OH and $R_3$, $R_7$, $R_9$, and $R_{12}$ are all H,
 f) $R_3$ is OH and $R_7$, $R_9$, $R_{12}$, and $R_{14}$ are all H,
 g) $R_{14}$ is $NO_2$ and $R_3$, $R_7$, $R_9$, and $R_{12}$ are all H,
 h) $R_{12}$ is Br, $R_{14}$ is $NO_2$ and $R_3$, $R_7$, and $R_9$ are all H,
 i) $R_3$ and $R_9$ are both $OCH_3$, $R_{12}$ is Br, $R_{14}$ is $NO_2$ and $R_7$ is H, or
 j) $R_3$ and $R_9$ are both $OCH_3$, $R_{14}$ is $NO_2$ and $R_7$ and $R_{12}$ are both H.

6. The method of claim 1, wherein the composition further comprises at least one excipient.

7. The method of claim 1, wherein $R_3$ is $CH_3$ and $R_7$, $R_9$, $R_{12}$, and $R_{14}$ are all H.

8. The method of claim 1, wherein the neurodegenerative disorder is Parkinson's disease.

9. The method of claim 1, wherein the composition is administered intravenously to the subject.

10. The method of claim 1, wherein the composition is administered intraperitoneally to the subject.

11. The method of claim 1, wherein the composition is administered orally to the subject.

12. The method of claim 1 further comprising administering before, simultaneously with, or after the administration of said composition a formulation comprising one or more other therapeutic agent for treating a neurodegenerative disorder.

13. The method of claim 8, further comprising administering before, simultaneously with, or after the administration of said composition a formulation comprising one or more other anti-Parkinson's disease agent.

14. The method of claim 1, wherein the compound or complex of $^{64}Zn_e$ is part of a zinc finger peptide.

15. The method of claim 1, wherein the subject is a human subject.

16. The method of claim 1, wherein the $^{85}Rb_e$ compound is present in an amount equivalent to between 40 mg $^{85}Rb_e$ and 2400 mg $^{85}Rb_e$.

17. The method of claim 1, wherein the compound or complex of $^{64}Zn_e$ is present in an amount equivalent to between doses of $^{64}Zn_e$ (by metal) ranges from 0.1 to 1.5 mg of pure $^{64}Zn_e$ per 1 kg of human body weight.

18. The method of claim 1, wherein the compound or complex of $^{64}Zn_e$ (by metal) ranges from 1 to 15 mg of pure $^{64}Zn_e$ per 1 kg of human body weight.

* * * * *